(12) United States Patent
Giritch et al.

(10) Patent No.: US 10,201,168 B2
(45) Date of Patent: Feb. 12, 2019

(54) COLICINS FOR THE CONTROL OF EHEC

(71) Applicant: Nomad Bioscience GmbH, Munich (DE)

(72) Inventors: Anatoli Giritch, Halle (DE); Simone Hahn, Halle (DE); Steve Schulz, Halle (DE); Anett Stephan, Halle (DE); Yuri Gleba, Berlin (DE); Franziska Jarczowski, Seegebiet ML (DE)

(73) Assignee: Nomad Bioscience GmbH, Munich (DE)

( * ) Notice: Subject to any disclaimer, the term of this patent is extended or adjusted under 35 U.S.C. 154(b) by 0 days.

(21) Appl. No.: 15/144,271

(22) Filed: May 2, 2016

(65) Prior Publication Data

US 2016/0345599 A1  Dec. 1, 2016

Related U.S. Application Data

(60) Provisional application No. 62/166,379, filed on May 26, 2015.

(30) Foreign Application Priority Data

Aug. 14, 2015  (EP) .................................. 15181133

(51) Int. Cl.
| | | |
|---|---|---|
| *A23B 4/10* | (2006.01) | |
| *A01N 63/02* | (2006.01) | |
| *A23B 4/20* | (2006.01) | |
| *A23B 7/154* | (2006.01) | |
| *A23B 7/16* | (2006.01) | |

(52) U.S. Cl.
CPC ................ *A23B 4/10* (2013.01); *A01N 63/02* (2013.01); *A23B 4/20* (2013.01); *A23B 7/154* (2013.01); *A23B 7/16* (2013.01); *A23V 2002/00* (2013.01)

(58) Field of Classification Search
CPC .... A23B 4/22; A23B 4/10; A23B 4/20; A23B 7/154; A23B 7/16; A23L 3/3463; A23L 3/3571; C07K 14/245; A23V 2002/00; A01N 63/02
See application file for complete search history.

(56) References Cited

U.S. PATENT DOCUMENTS

| | | | |
|---|---|---|---|
| 7,592,159 B2 | 9/2009 | Stahl | |
| 2015/0050253 A1 | 2/2015 | Gabant | |

FOREIGN PATENT DOCUMENTS

| WO | 9426132 | 11/1994 | |
|---|---|---|---|
| WO | WO 94/26132 | * 11/1994 | ............... A23L 3/34 |
| WO | 2005089812 | 9/2005 | |
| WO | WO 2014/009744 | * 1/2014 | ............. A61K 38/16 |
| WO | 2015121443 A1 | 8/2015 | |

OTHER PUBLICATIONS

Touze et al., (Biochemical Society Transactions. 2012. vol. 40, part 6. pp. 1522-1527.*

(Continued)

*Primary Examiner* — Jana A Hines
(74) *Attorney, Agent, or Firm* — David M. Saravitz; Williams Mullen, P.C.

(57) ABSTRACT

The invention provides a method of preventing or reducing contamination of an object such as food with enterohaemorrhagic *E. coli* (EHEC), comprising contacting said object with colicin M or a derivative thereof.

14 Claims, 25 Drawing Sheets

Specification includes a Sequence Listing.

(56) References Cited

OTHER PUBLICATIONS

Kamensek et al., (BMC Microbiol. 2013. vol. 1:42).*
Budic et al., (PLoS One. 2011; 6(12): e28769).*
American Type Culture Collection, Printed Jun. 10, 2016. "'Big Six'Non-0157 Shiga Toxin-Producing *Escherichia coli* (STEC) Research Materials." https://www.atcc.org/~/media/PDFs/Big%20Six.ashx. 4 pages.
Paul N. Goldwater and Karl A. Bettelheim, "Treatment of enterohemorrhagic *Escherichia coli* (EHEC) infection and hemolytic uremic syndrome (HUS)", BMC Medicine 2012, 10:12, http://www.biomedcentral.com/1741-7015/10/12.
Kornelious Zeth et al., "Crystal Structure of Colicin M, a Novel Phosphatase Specifically Imported by *Escherichia coli*", The Journal of Biological Chemistry, vol. 283, No. 37, pp. 253124-25331, Sep. 12, 2008.
Maruska Budic et al., "*Escherichia coli* Bacteriocins: Antimicrobial Efficacy and Prevalence among Isolates from Patients with Bacteraemia", PLoS ONE, vol. 6, Issue 12, Dec. 2011.
Helene Barreteau et al., "Characterization of Colicin M and its Orthologs Targeting Bacterial Cell Wall Peptidoglycan Biosynthesis", Microbial Drug Resistance, vol. 18, No. 3, 2012.
Helene Barreteau et al., "Human- and Plant-Pathogenic *Pseudomonas* Species Produce Bateriocins Exhibiting Colicin M-Like Hydrolase Activity towards Peptidoglycan Precursors", Journal of Bacteriology, Jun. 2009, pp. 3657-3664.
Volkmar Bruan et al., "Import of periplasmic bacteriocins targeting the murein", Biochemical Society Trans, 40, pp. 1449-1455, 2012.
Simone Hahn et al., "T8-02 Cocktails of Plant-Produced Colicins for Efficient Control of Pathogenic Strains of *Escherichia coli*", International Association for Food Protection, Jul. 27, 2015, https://iafp.confec.com/iafp/2015/webporgram/Paper8893.html.
Volkmar Braun et al., "Isolation, Characterization, and Action of Colicin M, Antimicrobial Agents and Chemotherapy", vol. 5, No. 5, pp. 520-533, May 1974.
Simona Kamensek and Darja Zgur-Bertok, "Global transcriptional responses to the bacteriocin colicin M in *Escherichia coli*", BMC Microbiology 2013, 13:42, http://www.biomedcentral.com/1471-2180/13/42, 10 pages.
Rhys Grinter and Daniel Walker, "Lipid II-degrading M-Class bacteriocins", Encyclopedia of Inorganic and Bioinorganic Chemistry, 2014.
Stephanie Helbig and Volkmar Bruan, "Mapping Functional Domains of Colicin M", Journal of Bacteriology, Feb. 2011, pp. 815-821.
V. Bruan et al., "Penetration of colicin M into cells of *Escherichia coli*, Journal of Bacteriology", 142(1):162-168, 1980.
J. Köck et al., "Primary structure of colicin M, an inhibitor of murein biosynthesis", Journal of Bacteriology, 169(7):3358-3361, 1987.
Shelton E. Murinda et al., "Evaluation of Colicins for Inhibitory Activity against Diarrheagenic *Escherichia coli* Strains, Including Serotype O157:H7", Applied and Environmental Microbiology, Sep. 1996, pp. 3196-3202.
Jennifer Lynne Jacobs, "Colicinogenic Maize: Transgenic Analysis and Effectiveness Against Pathogenic *Escherichia coli* O157:H7", UMI Microform 3252494, 2007.
48th Annual Maize Genetics Conference, Program and Abstract, Mar. 9-12, 2006, Asilomar Conference Grounds Pacific Grove, California, 205 pages.
European Search Report for EP 15181133.8, EPO, dated Nov. 23, 2015.
L. Sarada Nandiwada et al., "Characterization of an E2-type colicin and its application to treat alfalfa seeds to reduce *Escherichia coli* 0157:H7", International Journal of Food Microbiology, vol. 9, No. 3, Jun. 1, 2004 pp. 367-279.
H. Toshima et al., "Enhancement of Shiga Toxin Production in Enterohemorrhagic *Escherichia coli* Serotype 0157:h7 by DNase Colicins" Applied and Environmental Microbiology, vol. 73, No. 23, Dec. 1, 2007, pp. 7582-7588.
Etcheverria, A. et al. "Reduction of Adherence of *E. coli* 0157:H7 to HEp-2 Cells and to Bovine Large Intestinal Mucosal Explants by Colicinogenic *E. coli*." Database Medline, US National Library of Medicine, database accession No. NLM23724308, ISRN Microbiology, vol. 2011 p. 697020, 2011.
Schambergert, Gerry et al., "Characterization of colicinogenic *Escherichia coli* strains inhibitory to enterohomorrhagic *Escherichia coli*." Database Medline, US National Library of Medicine, database accession No. NLM15035362, Journal of Food Protection, vol. 67, No. 3, Mar. 2004, pp. 486-492.
M. El Ghachi et al., "Colicin M. Exerts Its Bacteriolytic Effect via Enzymatic Degradation of Undecaprenyl Phosphate-linked Peptidoglycan Precursors" Journal of Biological Chemistry, vol. 281, No. 32, Aug. 11, 2006, pp. 22761-22772.
Volkmar Braun et al., "Ton-dependent colicins and mircocins: modular design and evolution" Biochimie vol. 84, No. 5-6, May 1, 2002, pp. 365-380.

* cited by examiner

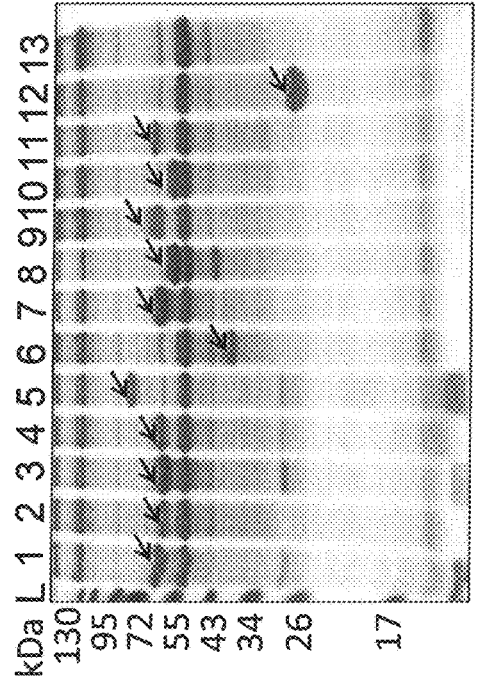
FIG. 4A
FIG. 4B

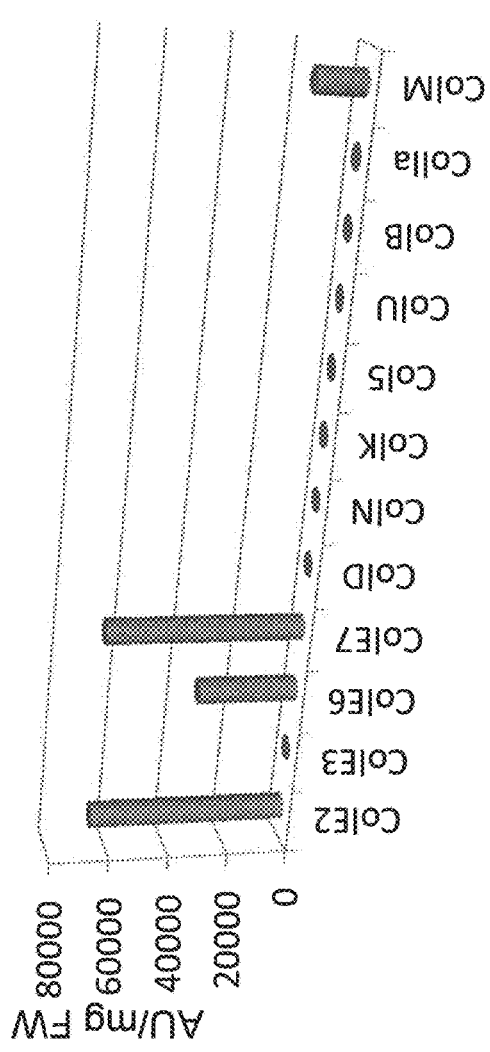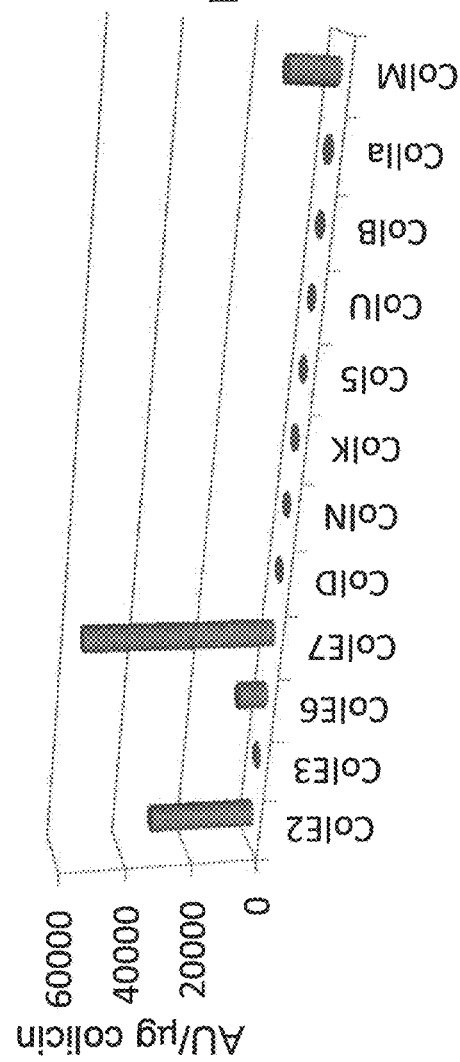

Effect of colicin treatment on bacterial populations of *E. coli* O157:H7 (DSM19206) on fresh-cut pieces of melon □ no treatment
■ spray carrier
▨ spray colM+ColE7

Storage time: 1 h 4°C, 1 d 4°C, 3 d 4°C

Effect of colicin treatment on bacterial populations of *E. coli* O157:H7 (DSM19206) on fresh-cut pieces of apple ☐ spray carrier
■ spray colM+colE7
☒ spray colM+colE7+colK+colB+col5

| | |
|---|---|
| 1a | Vector or ethanol inducer |
| 1b | |
| 2 | Host plant propagation |
| 3a | Application of vector or ethanol inducer |
| 3b | |
| 4 | Incubation (colicin expression) |
| 5 | Harvest |
| 6 | Homogenization of plant tissue |
| 7 | Acidic extraction |
| 8 | Clarification (centrifugation/filtration) |
| 9 | Alkaline treatment/neutralization |
| 10 | Clarification (centrifugation/filtration) |
| 11 | Ultrafiltration |
| 12 | Diafiltration |
| 13 | Column chromatography |
| 14 | Formulation |
| 15 | Filtration |
| 16 | Freeze drying |
| 17 | COLICIN Concentrate / COLICIN Isolate |

Performed under: GACP, GMP

Fig. 17

| Nr | Colicin | Plasmid construct | Intron position |
|---|---|---|---|
| 1 | colE5 | pNMD25880 | G468 |
| 2 | colE8 | pNMD25891 | G513 |
| 3 | colE9 | pNMD25901 | V546 |
| 4 | cloacin DF13 | pNMD15351 | G528 |
| 5 | colA | pNMD25831 | no intron |
| 6 | colS4 | pNMD25856 | no intron |
| 7 | col10 | pNMD25848 | no intron |
| 8 | colR | pNMD25813 | no intron |
| 9 | col28b | pNMD25871 | no intron |
| 10 | colY | pNMD26490 | V451 |
| 11 | colIb | pNMD25861 | no intron |

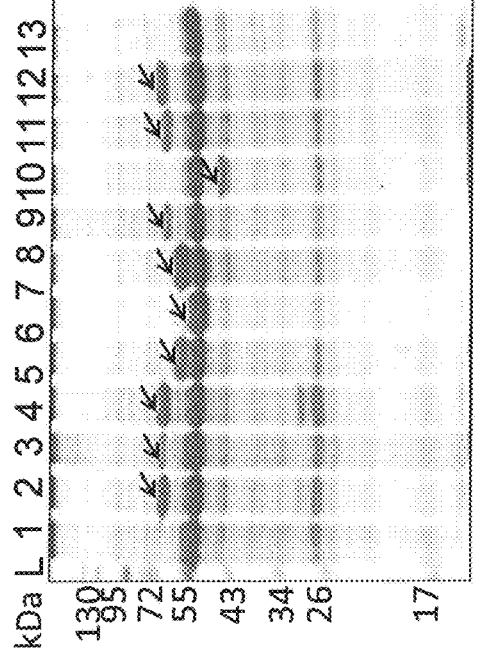
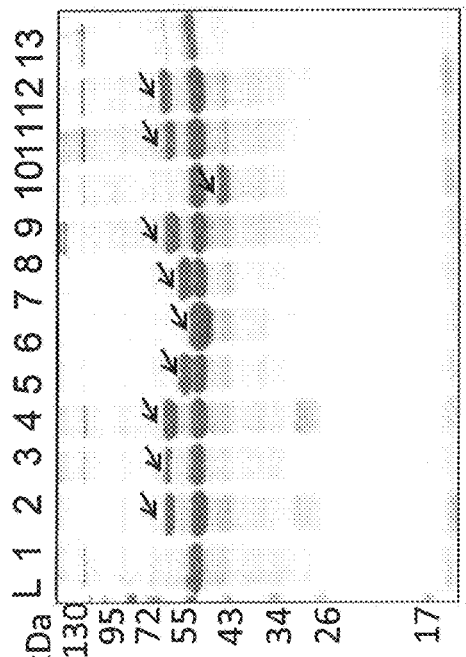
FIG. 20A
FIG. 20B

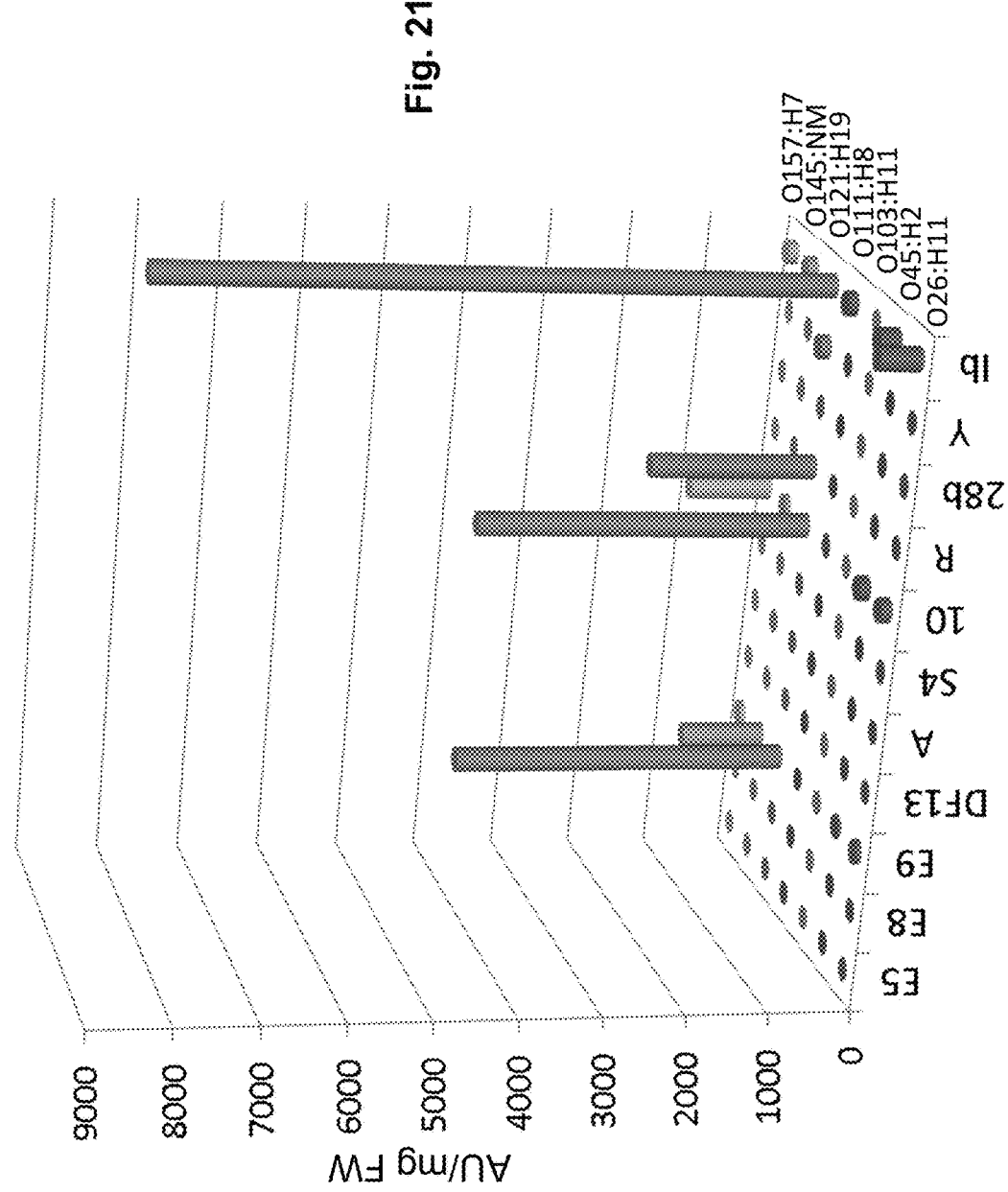

SEQUENCE LISTING

<160> NUMBER OF SEQ ID NOS: 8

<210> SEQ ID NO 1
<211> LENGTH: 271
<212> TYPE: PRT
<213> ORGANISM: Escherichia coli

<400> SEQUENCE: 1

Met Glu Thr Leu Thr Val His Ala Pro Ser Pro Ser Thr Asn Leu Pro
1               5                   10                  15

Ser Tyr Gly Asn Gly Ala Phe Ser Leu Ser Ala Pro His Val Pro Gly
            20                  25                  30

Ala Gly Pro Leu Leu Val Gln Val Val Tyr Ser Phe Phe Gln Ser Pro
        35                  40                  45

Asn Met Cys Leu Gln Ala Leu Thr Gln Leu Glu Asp Tyr Ile Lys Lys
    50                  55                  60

His Gly Ala Ser Asn Pro Leu Thr Leu Gln Ile Ile Ser Thr Asn Ile
65                  70                  75                  80

Gly Tyr Phe Cys Asn Ala Asp Arg Asn Leu Val Leu His Pro Gly Ile
                85                  90                  95

Ser Val Tyr Asp Ala Tyr His Phe Ala Lys Pro Ala Pro Ser Gln Tyr
            100                 105                 110

Asp Tyr Arg Ser Met Asn Met Lys Gln Met Ser Gly Asn Val Thr Thr
        115                 120                 125

```
Pro Ile Val Ala Leu Ala His Tyr Leu Trp Gly Asn Gly Ala Glu Arg
    130                 135                 140

Ser Val Asn Ile Ala Asn Ile Gly Leu Lys Ile Ser Pro Met Lys Ile
145                 150                 155                 160

Asn Gln Ile Lys Asp Ile Ile Lys Ser Gly Val Val Gly Thr Phe Pro
                165                 170                 175

Val Ser Thr Lys Phe Thr His Ala Thr Gly Asp Tyr Asn Val Ile Thr
            180                 185                 190

Gly Ala Tyr Leu Gly Asn Ile Thr Leu Lys Thr Glu Gly Thr Leu Thr
        195                 200                 205

Ile Ser Ala Asn Gly Ser Trp Thr Tyr Asn Gly Val Val Arg Ser Tyr
    210                 215                 220

Asp Asp Lys Tyr Asp Phe Asn Ala Ser Thr His Arg Gly Ile Ile Gly
225                 230                 235                 240

Glu Ser Leu Thr Arg Leu Gly Ala Met Phe Ser Gly Lys Glu Tyr Gln
                245                 250                 255

Ile Leu Leu Pro Gly Glu Ile His Ile Lys Glu Ser Gly Lys Arg
                260                 265                 270
```

<210> SEQ ID NO 2
<211> LENGTH: 9656
<212> TYPE: DNA
<213> ORGANISM: Artificial Sequence
<220> FEATURE:
<223> OTHER INFORMATION: pNMD035

<400> SEQUENCE: 2

```
cctgtggttg gcacatacaa atggacgaac ggataaacct tttcacgccc ttttaaatat      60
ccgattattc taataaacgc tcttttctct taggtttacc cgccaatata tcctgtcaaa     120
cactgatagt ttaaactgaa ggcgggaaac gacaatctga tctaagctag cttggaattg     180
gtaccacgcg tttcgacaaa atttagaacg aacttaatta tgatctcaaa tacattgata     240
catatctcat ctagatctag gttatcatta tgtaagaaag ttttgacgaa tatggcacga     300
caaaatggct agactcgatg taattggtat ctcaactcaa cattatactt ataccaaaca     360
ttagttagac aaaatttaaa caactatttt ttatgtatgc aagagtcagc atatgtataa     420
ttgattcaga atcgttttga cgagttcgga tgtagtagta gccattattt aatgtacata     480
ctaatcgtga atagtgaata tgatgaaaca ttgtatctta ttgtataaat atccataaac     540
acatcatgaa agacactttc tttcacggtc tgaattaatt atgatacaat tctaatagaa     600
aacgaattaa attacgttga attgtatgaa atctaattga acaagccaac cacgacgacg     660
actaacgttg cctggattga ctcggtttaa gttaaccact aaaaaaacgg agctgtcatg     720
taacacgcgg atcgagcagg tcacagtcat gaagccatca agcaaaaga actaatccaa     780
gggctgagat gattaattag tttaaaaatt agttaacacg agggaaaagg ctgtctgaca     840
gccaggtcac gttatcttta cctgtggtcg aaatgattcg tgtctgtcga ttttaattat     900
ttttttgaaa ggccgaaaat aaagttgtaa gagataaacc cgcctatata aattcatata     960
ttttcctctc cgctttgaag ttttagtttt attgcaacaa caacaacaaa ttacaataac    1020
aacaaacaaa atacaaacaa caacaacatg gcacaatttc aacaaacaat tgacatgcaa    1080
actctccaag ccgctgcggg acgcaacagc ttggtgaatg atttggcatc tcgtcgcgtt    1140
tacgataatg cagtcgagga gctgaatgct cgttccagac gtcccaaggt aataggaact    1200
ttctggatct actttatttg ctggatctcg atcttgtttt ctcaatttcc ttgagatctg    1260
```

```
gaattcgttt aatttggatc tgtgaacctc cactaaatct tttggtttta ctagaatcga    1320
tctaagttga ccgatcagtt agctcgatta tagctaccag aatttggctt gaccttgatg    1380
gagagatcca tgttcatgtt acctgggaaa tgatttgtat atgtgaattg aaatctgaac    1440
tgttgaagtt agattgaatc tgaacactgt caatgttaga ttgaatctga acactgttta    1500
aggttagatg aagtttgtgt atagattctt cgaaacttta ggatttgtag tgtcgtacgt    1560
tgaacagaaa gctatttctg attcaatcag ggtttatttg actgtattga actcttttg    1620 tgtgtttgca ggtccacttc tccaaggcag tgtctacgga acagaccctg attgcaacaa    1680
acgcatatcc ggagttcgag atttcctta ctcatacgca atccgctgtg cactccttgg    1740
ccggaggcct tcggtcactt gagttggagt atctcatgat gcaagttccg ttcggttctc    1800
tgacgtacga catcggcggt aacttttccg cgcacctttt caaagggcgc gattacgttc    1860
actgctgcat gcctaatctg gatgtacgtg acattgctcg ccatgaagga cacaaggaag    1920
ctatttacag ttatgtgaat cgtttgaaaa ggcagcagcg tcctgtgcct gaataccaga    1980
gggcagcttt caacaactac gctgagaacc cgcacttcgt ccattgcgac aaacctttcc    2040
aacagtgtga attgacgaca gcgtatggca ctgacaccta cgctgtagct ctccatagca    2100
tttatgatat ccctgttgag gagttcggtt ctgcgctact caggaagaat gtgaaaactt    2160
gtttcgcggc cttcattc catgagaata tgcttctaga ttgtgataca gtcacactcg    2220
atgagattgg agctacgttc cagaaatcag gtaacattcc ttagttacct ttcttttctt    2280
tttccatcat aagtttatag attgtacatg ctttgagatt tttctttgca acaatctca    2340 ggtgataacc tgagcttctt cttccataat gagagcactc tcaattacac ccacagcttc    2400
agcaacatca tcaagtacgt gtgcaagacg ttcttccctg ctagtcaacg cttcgtgtac    2460
cacaaggagt tcctggtcac tagagtcaac acttggtact gcaagttcac gagagtggat    2520
acgttcactc tgttccgtgg tgtgtaccac aacaatgtgg attgcgaaga gttttacaag    2580
gctatggacg atgcgtggca ctacaaaaag acgttagcaa tgcttaatgc cgagaggacc    2640
atcttcaagg ataacgctgc gttaaacttc tggttcccga aggtgctctt gaaattggaa    2700
gtcttctttt gttgtctaaa cctatcaatt tctttgcgga aatttatttg aagctgtaga    2760
gttaaaattg agtcttttaa acttttgtag gtgagagaca tggttatcgt ccctctcttt    2820
gacgcttcta tcacaactgg taggatgtct aggagagagg ttatggtgaa caaggacttc    2880
gtctacacgg tcctaaatca catcaagacc tatcaagcta aggcactgac gtacgcaaac    2940
gtgctgagct tcgtggagtc tattaggtct agagtgataa ttaacggtgt cactgccagg    3000
taagttgtta cttatgattg ttttcctctc tgctacatgt attttgttgt tcatttctgt    3060
aagatataag aattgagttt tcctctgatg atattattag gtctgaatgg gacacagaca    3120
aggcaattct aggtccatta gcaatgacat tcttcctgat cacgaagctg ggtcatgtgc    3180
aagatgaaat aatcctgaaa aagttccaga agttcgacag aaccaccaat gagctgattt    3240
ggacaagtct ctgcgatgcc ctgatggggg ttattccctc ggtcaaggag acgcttgtgc    3300
gcggtggttt tgtgaaagta gcagaacaag ccttagagat caaggttagt atcatatgaa    3360
gaaataccta gtttcagttg atgaatgcta ttttctgacc tcagttgttc tcttttgaga    3420
attatttctt ttctaatttg cctgattttt ctattaattc attaggttcc cgagctatac    3480
tgtaccttcg ccgaccgatt ggtactacag tacaagaagg cggaggagtt ccaatcgtgt    3540
gatctttcca aacctctaga agagtcagag aagtactaca acgcattatc cgagctatca    3600
gtgcttgaga atctcgactc ttttgactta gaggcgttta agactttatg tcagcagaag    3660
```

```
aatgtggacc cggatatggc agcaaaggta aatcctggtc cacacttttta cgataaaaac    3720 acaagatttt aaactatgaa ctgatcaata atcattccta aaagaccaca cttttgtttt    3780
gtttctaaag taattttttac tgttataaca ggtggtcgta gcaatcatga agtcagaatt    3840
gacgttgcct ttcaagaaac ctacagaaga ggaaatctcg gagtcgctaa aaccaggaga    3900
ggggtcgtgt gcagagcata aggaagtgtt gagcttacaa aatgatgctc cgttcccgtg    3960
tgtgaaaaat ctagttgaag gttccgtgcc ggcgtatgga atgtgtccta agggtggtgg    4020
tttcgacaaa ttggatgtgg acattgctga tttccatctc aagagtgtag atgcagttaa    4080
aaagggaact atgatgtctg cggtgtacac agggtctatc aaagttcaac aaatgaagaa    4140
ctacatagat tacttaagtg cgtcgctggc agctacagtc tcaaacctct gcaaggtaag    4200
aggtcaaaag gtttccgcaa tgatccctct ttttttgttt ctctagtttc aagaatttgg    4260
gtatatgact aacttctgag tgttccttga tgcatatttg tgatgagaca aatgtttgtt    4320
ctatgtttta ggtgcttaga gatgttcacg gcgttgaccc agagtcacag gagaaatctg    4380
gagtgtggga tgttaggaga ggacgttggt tacttaaacc taatgcgaaa agtcacgcgt    4440
ggggtgtggc agaagacgcc aaccacaagt tggttattgt gttactcaac tgggatgacg    4500
gaaagccggt ttgtgatgag acatggttca gggtggcggt gtcaagcgat tccttgatat    4560
attcggatat gggaaaactt aagacgctca cgtcttgcag tccaaatggt gagccaccgg    4620
agcctaacgc caaagtaatt ttggtcgatg tgttcccgg ttgtggaaaa acgaaggaga    4680
ttatcgaaaa ggtaagttct gcatttggtt atgctccttg cattttaggt gttcgtcgct    4740
cttccatttc catgaatagc taagattttt tttctctgca ttcattcttc ttgcctcagt    4800
tctaactgtt tgtggtattt ttgttttaat tattgctaca ggtaaacttc tctgaagact    4860
tgattttagt ccctgggaag gaagcttcta agatgatcat ccggagggcc aaccaagctg    4920
gtgtgataag agcggataag gacaatgtta gaacggtgga ttccttcttg atgcatcctt    4980
ctagaagggt gtttaagagg ttgttttatcg atgaaggact aatgctgcat acaggttgtg    5040
taaatttcct actgctgcta tctcaatgtg acgtcgcata tgtgtatggg gacacaaagc    5100
aaattccgtt catttgcaga gtcgcgaact ttccgtatcc agcgcatttt gcaaaactcg    5160
tcgctgatga gaaggaagtc agaagagtta cgctcaggta aagcaactgt gtttaatca    5220 atttcttgtc aggatatatg gattataact taattttga gaaatctgta gtatttggcg    5280
tgaaatgagt ttgcttttgg gtttctcccg tgttataggt gcccggctga tgttacgtat    5340
ttccttaaca agaagtatga cggggcggtg atgtgtacca gcgcggtaga gagatccgtg    5400
aaggcagaag tggtgagagg aaagggtgca ttgaacccaa taaccttacc gttggagggt    5460
aaaattttga ccttcacaca agctgacaag ttcgagttac tggagaaggg ttacaaggta    5520
aagtttccaa ctttcctta ccatatcaaa ctaaagttcg aaactttta tttgatcaac    5580 ttcaaggcca cccgatcttt ctattcctga ttaatttgtg atgaatccat attgactttt    5640
gatggttacg caggatgtga acactgtgca cgaggtgcaa ggggagacgt acgagaagac    5700
tgctattgtg cgcttgacat caactccgtt agagatcata tcgagtgcgt cacctcatgt    5760
tttggtggcg ctgacaagac acacaacgtg ttgtaaatat tacaccgttg tgttggaccc    5820
gatggtgaat gtgatttcag aaatggagaa gttgtccaat ttccttcttg acatgtatag    5880
agttgaagca ggtctgtctt tcctatttca tatgtttaat cctaggaatt tgatcaattg    5940
attgtatgta tgtcgatccc aagacttct tgttcactta tatcttaact ctctctttgc    6000
tgtttcttgc aggtgtccaa tagcaattac aaatcgatgc agtattcagg ggacagaact    6060
```

```
tgtttgttca gacgcccaag tcaggagatt ggcgagatat gcaattttac tatgacgctc    6120
ttcttcccgg aaacagtact attctcaatg aatttgatgc tgttacgatg aatttgaggg    6180
atatttcctt aaacgtcaaa gattgcagaa tcgacttctc caaatccgtg caacttccta    6240
aagaacaacc tattttcctc aagcctaaaa taagaactgc ggcagaaatg ccgagaactg    6300
caggtaaaat attggatgcc agacgatatt cttctttg atttgtaact ttttcctgtc    6360
aaggtcgata aatttatt ttttggtaa aaggtcgata attttttttt ggagccatta    6420
tgtaattttc ctaattaact gaaccaaaat tatacaaacc aggtttgctg gaaaatttgg    6480
ttgcaatgat caaagaaac atgaatgcgc cggatttgac agggacaatt gacattgagg    6540
atactgcatc tctggtggtt gaaaagtttt gggattcgta tgttgacaag gaatttagtg    6600
gaacgaacga aatgaccatg acaagggaga gcttctccag gtaaggactt ctcatgaata    6660
ttagtggcag attagtgttg ttaaagtctt tggttagata atcgatgcct cctaattgtc    6720
catgttttac tggttttcta caattaaagg tggcttcga aacaagagtc atctacagtt    6780
ggtcagttag cggactttaa cttgtggat ttgccggcag tagatgagta caagcatatg    6840
atcaagagtc aaccaaagca aaagttagac ttgagtattc aagacgaata tcctgcattg    6900
cagacgatag tctaccattc gaaaagatc aatgcgattt tcggtccaat gtttcagaa    6960 cttacgagga tgttactcga aaggattgac tcttcgaagt ttctgttcta caccagaaag    7020
acacctgcac aaatagagga cttctttct gacctagact caacccaggc gatggaaat    7080 ctggaactcg acatttcgaa gtacgataag tcacaaaacg agttccattg tgctgtagag    7140
tacaagatct gggaaaagtt aggaattgat gagtggctag ctgaggtctg gaaacaaggt    7200
gagttcctaa gttccatttt tttgtaatcc ttcaatgtta ttttaactttt tcagatcaac    7260 atcaaaatta ggttcaattt tcatcaacca aataatattt ttcatgtata tataggtcac    7320
agaaaaacga ccttgaaaga ttatacggcc ggaatcaaaa catgtctttg gtatcaaagg    7380
aaaagtggtg atgtgacaac ctttattggt aataccatca tcattgccgc atgtttgagc    7440
tcaatgatcc ccatggacaa agtgataaag gcagctttt gtggagacga tagcctgatt    7500
tacattccta aaggtttaga cttgcctgat attcaggcgg gcgcgaacct catgtggaac    7560
ttcgaggcca aactcttcag gaagaagtat ggttacttct gtggtcgtta tgttattcac    7620
catgatagag gagccattgt gtattacgat ccgcttaaac taatatctaa gttaggttgt    7680
aaacatatta gagatgttgt tcacttagaa gagttacgcg agtctttgtg tgatgtagct    7740
agtaacttaa ataattgtgc gtattttca cagttagatg aggccgttgc cgaggttcat    7800
aagaccgcgg taggcggttc gtttgctttt tgtagtataa ttaagtattt gtcagataag    7860
agattgttta gagatttgtt ctttgtttga taatgtcgat agtctcgtac gaacctaagg    7920
tgagtgattt cctcaatctt tcgaagaagg aagagatctt gccgaaggct ctaacgaggt    7980
taaaaaccgt gtctattagt actaaagata ttatatctgt caaggagtcg gagactttgt    8040
gtgatataga tttgttaatc aatgtgccat tagataagta tagatatgtg ggtatcctag    8100
gagccgtttt taccggagag tggctagtgc cagacttcgt taaaggtgga gtgacgataa    8160
gtgtgataga taagcgtctg gtgaactcaa aggagtgcgt gattggtacg tacagagccg    8220
cagccaagag taagaggttc cagttcaaat tggttccaaa ttactttgtg tccaccgtgg    8280
acgcaaagag gaagccgtgg caggtaagga tttttatgat atagtatgct tatgtatttt    8340
gtactgaaag catatcctgc ttcattggga tattactgaa agcatttaac tacatgtaaa    8400
ctcacttgat gatcaataaa cttgattttg caggttcatg ttcgtataca agacttgaag    8460
```

```
attgaggcgg gttggcagcc gttagctctg gaagtagttt cagttgctat ggtcaccaat      8520
aacgttgtca tgaagggttt gagggaaaag gtcgtcgcaa taaatgatcc ggacgtcgaa      8580
ggtttcgaag gtaagccatc ttcctgctta tttttataat gaacatagaa ataggaagtt      8640
gtgcagagaa actaattaac ctgactcaaa atctaccctc ataattgttg tttgatattg      8700
gtcttgtatt ttgcaggtgt ggttgacgaa ttcgtcgatt cggttgcagc atttaaagcg      8760
gttgacaact ttaaaagaag gaaaagaag gttgaagaaa agggtgtagt aagtaagtat       8820
aagtacagac cggagaagta cgccggtcct gattcgttta atttgaaaga gaaaacgtc      8880 ttacaacatt acaaacccga atcagtacca gtatttcgat aagaaacaag aaaccatgag      8940
agacctgata tccacaaccg tggtctcgag cttactagag cgtggtgcgc acgatagcgc      9000
atagtgtttt tctctccact tgaatcgaag agatagactt acggtgtaaa tccgtagggg      9060
tggcgtaaac caaattacgc aatgttttgg gttccattta aatcgaaacc ccttatttcc      9120
tggatcacct gttaacgcac gtttgacgtg tattacagtg gaataagta  aaagtgagag      9180 gttcgaatcc tccctaaccc cgggtagggg cccagcggcc gctctagcta gagtcaagca      9240
gatcgttcaa acatttggca ataaagtttc ttaagattga atcctgttgc cggtcttgcg      9300
atgattatca tataatttct gttgaattac gttaagcatg taataattaa catgtaatgc      9360
atgacgttat ttatgagatg gttttttatg attagagtcc cgcaattata catttaatac      9420
gcgatagaaa acaaaatata gcgcgcaaac taggataaat tatcgcgcgc ggtgtcatct      9480
atgttactag atcgacctgc atccacccca gtacattaaa aacgtccgca atgtgttatt      9540
aagttgtcta agcgtcaatt tgtttacacc acaatatatc ctgccaccag ccagccaaca      9600
gctccccgac cggcagctcg gcacaaaatc accactcgat acaggcagcc catcag         9656

<210> SEQ ID NO 3
<211> LENGTH: 10628
<212> TYPE: DNA
<213> ORGANISM: Artificial Sequence
<220> FEATURE:
<223> OTHER INFORMATION: pNMD10221

<400> SEQUENCE: 3
cctgtggttg gcacatacaa atggacgaac ggataaacct tttcacgccc ttttaaatat        60
ccgattattc taataaacgc tcttttctct taggtttacc cgccaatata tcctgtcaaa       120
cactgatagt ttaaactgaa ggcgggaaac gacaatctga tctaagctag cttggaattg       180
gtaccacgcg tttcgacaaa atttagaacg aacttaatta tgatctcaaa tacattgata       240
catatctcat ctagatctag gttatcatta tgtaagaaag ttttgacgaa tatggcacga       300
caaaatggct agactcgatg taattggtat ctcaactcaa cattatactt ataccaaaca       360
ttagttagac aaaatttaaa caactatttt ttatgtatgc aagagtcagc atatgtataa       420
ttgattcaga atcgttttga cgagttcgga tgtagtagta gccattattt aatgtacata       480
ctaatcgtga atagtgaata tgatgaaaca ttgtatctta ttgtataaat atccataaac       540
acatcatgaa agacactttc tttcacggtc tgaattaatt atgatacaat tctaatagaa       600
aacgaattaa attacgttga attgtatgaa atcaattga  acaagccaac cacgacgacg       660
actaacgttg cctggattga ctcggtttaa gttaaccact aaaaaaacgg agctgtcatg       720
taacacgcgg atcgagcagg tcacagtcat gaagccatca aagcaaaaga actaatccaa       780
gggctgagat gattaattag tttaaaaatt agttaacacg agggaaaagg ctgtctgaca       840
gccaggtcac gttatctta cctgtggtcg aaatgattcg tgtctgtcga ttttaattat        900
```

```
tttttttgaaa ggccgaaaat aaagttgtaa gagataaacc cgcctatata aattcatata    960
ttttcctctc cgctttgaag ttttagtttt attgcaacaa caacaacaaa ttacaataac   1020
aacaaacaaa atacaaacaa caacaacatg gcacaatttc aacaaacaat tgacatgcaa   1080
actctccaag ccgctgcggg acgcaacagc ttggtgaatg attttggcatc tcgtcgcgtt  1140
tacgataatg cagtcgagga gctgaatgct cgttccagac gtcccaaggt aataggaact   1200
ttctggatct actttatttg ctggatctcg atcttgtttt ctcaatttcc ttgagatctg   1260
gaattcgttt aatttggatc tgtgaacctc cactaaatct tttggtttta ctagaatcga   1320
tctaagttga ccgatcagtt agctcgatta tagctaccag aatttggctt gaccttgatg   1380
gagagatcca tgttcatgtt acctgggaaa tgatttgtat atgtgaattg aaatctgaac   1440
tgttgaagtt agattgaatc tgaacactgt caatgttaga ttgaatctga acactgttta   1500
aggttagatg aagtttgtgt atagattctt cgaaacttta ggatttgtag tgtcgtacgt   1560
tgaacagaaa gctatttctg attcaatcag ggttttatttg actgtattga actctttttg  1620
tgtgtttgca ggtccacttc tccaaggcag tgtctacgga acagaccctg attgcaacaa   1680
acgcatatcc ggagttcgag atttccttta ctcatacgca atccgctgtg cactccttgg   1740
ccggaggcct tcggtcactt gagttggagt atctcatgat gcaagttccg ttcggttctc   1800
tgacgtacga catcggcggt aacttttccg cgcaccttttt caaagggcgc gattacgttc  1860
actgctgcat gcctaatctg gatgtacgtg acattgctcg ccatgaagga cacaaggaag   1920
ctatttacag ttatgtgaat cgtttgaaaa ggcagcagcg tcctgtgcct gaataccaga   1980
gggcagcttt caacaactac gctgagaacc cgcacttcgt ccattgcgac aaaccttttcc  2040
aacagtgtga attgacgaca gcgtatggca ctgacaccta cgctgtagct ctccatagca   2100
tttatgatat ccctgttgag gagttcggtt ctgcgctact caggaagaat gtgaaaactt   2160
gtttcgcggc ctttcatttc catgagaata tgcttctaga ttgtgataca gtcacactcg   2220
atgagattgg agctacgttc cagaaatcag gtaacattcc ttagttacct ttcttttctt   2280
tttccatcat aagtttatag attgtacatg ctttgagatt tttctttgca aacaatctca   2340
ggtgataacc tgagcttctt cttccataat gagagcactc tcaattacac ccacagcttc   2400
agcaacatca tcaagtacgt gtgcaagacg ttcttccctg ctagtcaacg cttcgtgtac   2460
cacaaggagt tcctggtcac tagagtcaac acttggtact gcaagttcac gagagtggat   2520
acgttcactc tgttccgtgg tgtgtaccac aacaatgtgg attgcgaaga gttttacaag   2580
gctatggacg atgcgtggca ctacaaaaag acgttagcaa tgcttaatgc cgagaggacc   2640
atcttcaagg ataacgctgc gttaaacttc tggttcccga aggtgctctt gaaattggaa   2700
gtcttctttt gttgtctaaa cctatcaatt tctttgcgga aatttatttg aagctgtaga   2760
gttaaaattg agtcttttaa acttttgtag gtgagagaca tggttatcgt ccctctcttt   2820
gacgcttcta tcacaactgg taggatgtct aggagagagg ttatggtgaa caaggacttc   2880
gtctacacgg tcctaaatca catcaagacc tatcaagcta aggcactgac gtacgcaaac   2940
gtgctgagct tcgtggagtc tattaggtct agagtgataa ttaacggtgt cactgccagg   3000
taagttgtta cttatgattg ttttcctctc tgctacatgt attttgttgt tcatttctgt   3060
aagatataag aattgagttt tcctctgatg atattattag gtctgaatgg gacacagaca   3120
aggcaattct aggtccatta gcaatgacat tcttcctgat cacgaagctg ggtcatgtgc   3180
aagatgaaat aatcctgaaa aagttccaga agttcgacag aaccaccaat gagctgattt   3240
ggacaagtct ctgcgatgcc ctgatggggg ttattccctc ggtcaaggag acgcttgtgc   3300
```

```
gcggtggttt tgtgaaagta gcagaacaag ccttagagat caaggttagt atcatatgaa    3360
gaaataccta gtttcagttg atgaatgcta ttttctgacc tcagttgttc tcttttgaga    3420
attatttctt ttctaatttg cctgatttt ctattaattc attaggttcc cgagctatac     3480
tgtaccttcg ccgaccgatt ggtactacag tacaagaagg cggaggagtt ccaatcgtgt    3540
gatctttcca aacctctaga agagtcagag aagtactaca acgcattatc cgagctatca    3600
gtgcttgaga atctcgactc ttttgactta gaggcgttta agactttatg tcagcagaag    3660
aatgtggacc cggatatggc agcaaaggta atcctggtc cacacttta cgataaaaac      3720 acaagatttt aaactatgaa ctgatcaata atcattccta aaagaccaca cttttgtttt    3780
gtttctaaag taattttac tgttataaca ggtggtcgta gcaatcatga agtcagaatt     3840
gacgttgcct ttcaagaaac ctacagaaga ggaaatctcg gagtcgctaa accaggaga    3900 ggggtcgtgt gcagagcata aggaagtgtt gagcttacaa aatgatgctc cgttcccgtg   3960
tgtgaaaaat ctagttgaag gttccgtgcc ggcgtatgga atgtgtccta agggtggtgg   4020
tttcgacaaa ttggatgtgg acattgctga tttccatctc aagagtgtag atgcagttaa   4080
aaagggaact atgatgtctg cggtgtacac agggtctatc aaagttcaac aaatgaagaa   4140
ctacatagat tacttaagtg cgtcgctggc agctacagtc tcaaacctct gcaaggtaag   4200
aggtcaaaag gtttccgcaa tgatccctct tttttgttt ctctagtttc aagaattgg      4260 gtatatgact aacttctgag tgttccttga tgcatatttg tgatgagaca aatgtttgtt   4320
ctatgtttta ggtgcttaga gatgttcacg gcgttgaccc agagtcacag gagaaatctg   4380
gagtgtggga tgttaggaga ggacgttggt tacttaaacc taatgcgaaa agtcacgcgt   4440
ggggtgtggc agaagacgcc aaccacaagt tggttattgt gttactcaac tgggatgacg   4500
gaaagccggt ttgtgatgag acatggttca gggtggcggt gtcaagcgat tccttgatat   4560
attcggatat gggaaaactt aagacgctca cgtcttgcag tccaaatggt gagccaccgg   4620
agcctaacgc caaagtaatt ttggtcgatg gtgttcccgg ttgtgaaaaa acgaaggaga   4680
ttatcgaaaa ggtaagttct gcatttggtt atgctccttg catttaggt gttcgtcgct     4740 cttccatttc catgaatagc taagattttt ttctctgca ttcattcttc ttgcctcagt     4800
tctaactgtt tgtggtattt ttgttttaat tattgctaca ggtaaacttc tctgaagact   4860 tgatttagt ccctgggaag gaagcttcta agatgatcat ccggagggcc aaccaagctg    4920
gtgtgataag agcggataag gacaatgtta gaacggtgga ttccttcttg atgcatcctt   4980
ctagaagggt gtttaagagg ttgttttatcg atgaaggact aatgctgcat acaggttgtg  5040
taaatttcct actgctgcta tctcaatgtg acgtcgcata tgtgtatggg gacacaaagc   5100
aaattccgtt catttgcaga gtcgcgaact ttccgtatcc agcgcatttt gcaaaactcg   5160
tcgctgatga aggaagtc agaagagtta cgctcaggta aagcaactgt gttttaatca    5220
atttcttgtc aggatatatg gattataact taatttttga gaaatctgta gtatttggcg   5280
tgaaatgagt ttgcttttg gtttctcccg tgttataggt gcccggctga tgttacgtat    5340
ttccttaaca agaagtatga cggggcggtg atgtgtacca gcgcggtaga gagatccgtg   5400
aaggcagaag tggtgagagg aaagggtgca ttgaacccaa taaccttacc gttggagggt   5460
aaaattttga ccttcacaca agctgacaag ttcgagttac tggagaaggg ttacaaggta   5520
aagtttccaa ctttccttta ccatatcaaa ctaaagttcg aaactttta tttgatcaac    5580 ttcaaggcca cccgatcttt ctattcctga ttaatttgtg atgaatccat attgactttt   5640
gatggttacg caggatgtga acactgtgca cgaggtgcaa ggggagacgt acgagaagac   5700
```

```
tgctattgtg cgcttgacat caactccgtt agagatcata tcgagtgcgt cacctcatgt    5760
tttggtggcg ctgacaagac acacaacgtg ttgtaaatat tacaccgttg tgttggaccc    5820
gatggtgaat gtgatttcag aaatggagaa gttgtccaat ttccttcttg acatgtatag    5880
agttgaagca ggtctgtctt tcctatttca tatgtttaat cctaggaatt tgatcaattg    5940
attgtatgta tgtcgatccc aagactttct tgttcactta tatcttaact ctctctttgc    6000
tgtttcttgc aggtgtccaa tagcaattac aaatcgatgc agtattcagg ggacagaact    6060
tgtttgttca gacgcccaag tcaggagatt ggcgagatat gcaatttttac tatgacgctc    6120
ttcttcccgg aaacagtact attctcaatg aatttgatgc tgttacgatg aatttgaggg    6180
atatttcctt aaacgtcaaa gattgcagaa tcgacttctc caaatccgtg caacttccta    6240
aagaacaacc tattttcctc aagcctaaaa taagaactgc ggcagaaatg ccgagaactg    6300
caggtaaaat attggatgcc agacgatatt cttctctttg atttgtaact ttttcctgtc    6360
aaggtcgata aattttattt tttttggtaa aaggtcgata attttttttt ggagccatta    6420
tgtaattttc ctaattaact gaaccaaaat tatacaaacc aggtttgctg aaaatttgg     6480
ttgcaatgat caaagaaac atgaatgcgc cggatttgac agggacaatt gacattgagg     6540
atactgcatc tctggtggtt gaaaagtttt gggattcgta tgttgacaag gaatttagtg    6600
gaacgaacga aatgaccatg acaagggaga gcttctccag gtaaggactt ctcatgaata    6660
ttagtggcag attagtgttg ttaaagtctt tggttagata atcgatgcct cctaattgtc    6720
catgttttac tggttttcta caattaaagg tggctttcga acaagagtc atctacagtt     6780
ggtcagttag cggactttaa cttgtggat ttgccggcag tagatgagta caagcatatg     6840
atcaagagtc aaccaaagca aaagttagac ttgagtattc aagacgaata tcctgcattg    6900
cagacgatag tctaccattc gaaaagatc aatgcgattt tcggtccaat gttttcagaa     6960
cttacgagga tgttactcga aaggattgac tcttcgaagt ttctgttcta caccagaaag    7020
acacctgcac aaatagagga cttcttttct gacctagact caacccaggc gatgaaaatt    7080
ctggaactcg acatttcgaa gtacgataag tcacaaaacg agttccattg tgctgtagag    7140
tacaagatct gggaaaagtt aggaattgat gagtggctag ctgaggtctg gaaacaaggt    7200
gagttcctaa gttccatttt tttgtaatcc ttcaatgtta ttttaacttt tcagatcaac    7260
atcaaaatta ggttcaattt tcatcaacca aataatattt ttcatgtata tataggtcac    7320
agaaaaacga ccttgaaaga ttatacggcc ggaatcaaaa catgtctttg gtatcaaagg    7380
aaaagtggtg atgtgacaac ctttattggt aataccatca tcattgccgc atgtttgagc    7440
tcaatgatcc ccatggacaa agtgataaag gcagcttttt gtggagacga tagcctgatt    7500
tacattccta aaggtttaga cttgcctgat attcaggcgg cgcgaaccct catgtggaac    7560
ttcgaggcca aactcttcag gaagaagtat ggttacttct gtggtcgtta tgttattcac    7620
catgatagag gagccattgt gtattacgat ccgcttaaac taatatctaa gttaggttgt    7680
aaacatatta gagatgttgt tcacttagaa gagttacgcg agtctttgtg tgatgtagct    7740
agtaacttaa ataattgtgc gtatttttca cagttagatg aggccgttgc cgaggttcat    7800
aagaccgcgg taggcggttc gtttgctttt tgtagtataa ttaagtatttt gtcagataag    7860
agattgttta gagatttgtt ctttgtttga taatgtcgat agtctcgtac gaacctaagg    7920
tgagtgattt cctcaatctt tcgaagaagg aagagatctt gccgaaggct ctaacgaggt    7980
taaaaccgt gtctattagt actaaagata ttatatctgt caaggagtcg gagactttgt    8040
gtgatataga tttgttaatc aatgtgccat tagataagta tagatatgtg ggtatcctag    8100
```

```
gagccgtttt taccggagag tggctagtgc cagacttcgt taaaggtgga gtgacgataa    8160
gtgtgataga taagcgtctg gtgaactcaa aggagtgcgt gattggtacg tacagagccg    8220
cagccaagag taagaggttc cagttcaaat tggttccaaa ttactttgtg tccaccgtgg    8280
acgcaaagag gaagccgtgg caggtaagga ttttatgat atagtatgct tatgtatttt    8340
gtactgaaag catatcctgc ttcattggga tattactgaa agcatttaac tacatgtaaa    8400
ctcacttgat gatcaataaa cttgattttg caggttcatg ttcgtataca agacttgaag    8460
attgaggcgg gttggcagcc gttagctctg gaagtagttt cagttgctat ggtcaccaat    8520
aacgttgtca tgaagggttt gagggaaaag gtcgtcgcaa taaatgatcc ggacgtcgaa    8580
ggtttcgaag gtaagccatc ttcctgctta tttttataat gaacatagaa ataggaagtt    8640
gtgcagagaa actaattaac ctgactcaaa atctaccctc ataattgttg tttgatattg    8700
gtcttgtatt ttgcaggtgt ggttgacgaa ttcgtcgatt cggttgcagc atttaaagcg    8760
gttgacaact ttaaaagaag gaaaagaag gttgaagaaa agggtgtagt aagtaagtat    8820
aagtacagac cggagaagta cgccggtcct gattcgttta atttgaaaga agaaaacgtc    8880
ttacaacatt acaaacccga atcagtacca gtatttcgat aagaaacaag aaaccatgga    8940
aacccttact gtgcacgctc ctagcccttc tactaacctt ccttcttacg gtaacggtgc    9000
tttcagcctg tctgctcctc atgttcctgg tgctggtcct ttgcttgttc aggtggtgta    9060
cagcttcttc cagagcccta atatgtgcct tcaggctctt acccagcttg aggattacat    9120
caagaaacac ggtgctagca accctctgac cctgcagatt atctctacca atataggtaa    9180
atttctagtt tttctccttc attttcttgg ttaggaccct tttctctttt tattttttg    9240 agctttgatc tttctttaaa ctgatctatt ttttaattga ttggttatgg tgtaaatatt    9300
acatagcttt aactgataat ctgattactt tatttcgtgt gtctatgatg atgatgaaa    9360 ctgcaggtta tttctgcaac gctgatagga accttgtgct gcaccctggt atctctgtgt    9420
acgatgctta ccacttcgct aagcctgctc caagccagta cgattacaga tccatgaaca    9480
tgaagcagat gagcggtaac gtgaccaccc ctattgtggc tcttgctcat tacctttggg    9540
gaaacggtgc tgagagaagc gtgaacattg ctaatatcgg tctgaagatc agccctatga    9600
agatcaacca gatcaaggat atcatcaaga gcggtgtggt gggaaccttc cctgtgtcta    9660
ctaagttcac tcacgctacc ggtgattaca acgtgatcac cggtgcttac ctgggtaaca    9720
tcactcttaa gaccgaggga accctgacca tctctgctaa tggttcttgg acctacaatg    9780
gtgtggtgcg ttcctacgat gataagtacg atttcaacgc tagcacccac aggggtatca    9840
ttggtgagtc tcttactagg ctgggtgcta tgttcagcgg taaagagtac cagattctgc    9900
tgcctggtga gatccacatc aaagagtctg gtaagaggta agcttactag agcgtggtgc    9960
gcacgatagc gcatagtgtt tttctctcca cttgaatcga agagatagac ttacggtgta   10020
aatccgtagg ggtggcgtaa accaaattac gcaatgtttt gggttccatt taaatcgaaa   10080
ccccttattt cctggatcac ctgttaacgc acgtttgacg tgtattacag tgggaataag   10140
taaaagtgag aggttcgaat cctccctaac cccgggtagg ggcccagcgg ccgctctagc   10200
tagagtcaag cagatcgttc aaacatttgg caataaagtt tcttaagatt gaatcctgtt   10260
gccggtcttg cgatgattat catataattt ctgttgaatt acgttaagca tgtaataatt   10320
aacatgtaat gcatgacgtt atttatgaga tgggttttta tgattagagt cccgcaatta   10380
tacatttaat acgcgataga aaacaaaata tagcgcgcaa actaggataa attatcgcgc   10440
gcggtgtcat ctatgttact agatcgacct gcatccaccc cagtacatta aaaacgtccg   10500
```

```
caatgtgtta ttaagttgtc taagcgtcaa tttgtttaca ccacaatata tcctgccacc   10560
agccagccaa cagctccccg accggcagct cggcacaaaa tcaccactcg atacaggcag   10620
cccatcag                                                            10628

<210> SEQ ID NO 4
<211> LENGTH: 7422
<212> TYPE: DNA
<213> ORGANISM: Artificial Sequence
<220> FEATURE:
<223> OTHER INFORMATION: pNMD670

<400> SEQUENCE: 4
cctgtggttg gcacatacaa atggacgaac ggataaacct tttcacgccc ttttaaatat     60
ccgattattc taataaacgc tcttttctct taggtttacc cgccaatata tcctgtcaaa    120
cactgatagt ttaaactgaa ggcgggaaac gacaatctga tctaagctag gcatgcctgc    180
aggtcaacat ggtggagcac gacacgcttg tctactccaa aaatatcaaa gatacagtct    240
cagaagacca agggcaatt gagactttc aacaaagggt aatatccgga aacctcctcg      300
```

```
ttccacccgg tggattttc tttcaaagtg gaaacttggg acttcagatt ccacccttg      1980
caagcgtgga aagccttccg accaagggaa gtgtcggatg tagaggaaat ggaaagtttg    2040
ttctcagatg gggacctgct tgattgcttc acaagaatgc cagcttatgc ggtaaacgca    2100
gaggaagatt tagctgcaat caggaaaacg cccgagatgg atgtcggtca agaagttaaa    2160
gagcctgcag gagacagaaa tcaatactca aaccctgcag aaactttcct caacaagctc    2220
cacaggaaac acagtaggga ggtgaaacac caggccgcaa agaaagctaa acgcctagct    2280
gaaatccagg agtcaatgag agctgaaggt gatgccgaac caatgaaat aagcgggacg     2340
atggggcaa tacccagcaa cgccgaactt cctggcacga atgatgccag acaagaactc     2400
acactcccaa ccactaaacc tgtccctgca aggtgggaag atgcttcatt cacagattct    2460
agtgtggaag aggagcaggt taaactcctt ggaaaagaaa ccgttgaaac agcgacgcaa    2520
caagtcatcg aaggacttcc ttggaaacac tggattcctc aattaaatgc tgttggattc    2580
aaggcgctgg aaattcagag ggataggagt ggaacaatga tcatgcccat cacagaaatg    2640
gtgtccgggc tggaaaaaga ggacttccct gaaggaactc caaagagtt ggcacgagaa     2700
ttgttcgcta tgaacagaag ccctgccacc atcccttgg acctgcttag agccagagac     2760
tacggcagtg atgtaaagaa caagagaatt ggtgccatca caaagacaca ggcaacgagt    2820
tgggggcgaat acttgacagg aaagatagaa agcttaactg agaggaaagt tgcgacttgt    2880
gtcattcatg gagctggagg ttctggaaaa agtcatgcca tccagaaggc attgagagaa    2940
attggcaagg gctcggacat cactgtagtc ctgccgacca atgaactgcg gctagattgg    3000
agtaagaaag tgcctaacac tgagccctat atgttcaaga cctctgaaaa ggcgttaatt    3060
ggggggaacag gcagcatagt catctttgac gattactcaa aacttcctcc cggttacata    3120
gaagccttag tctgtttcta ctctaaaatc aagctaatca ttctaacagg agataagcaga    3180
caaagcgtct accatgaaac tgctgaggac gcctccatca ggcatttggg accagcaaca    3240
gagtacttct caaaatactg ccgatactat ctcaatgcca cacccgcaa caagaaagat     3300
cttgcgaaca tgcttggtgt ctacagtgag agaacgggag tcaccgaaat cagcatgagc    3360
gccgagttct tagaaggaat cccaactttg gtaccctcgg atgagaagag aaagctgtac    3420
atgggcaccg ggaggaatga cacgttcaca tacgctggat gccaggggct aactaagccg    3480
aaggtacaaa tagtgttgga ccacaacacc caagtgtgta gcgcgaatgt gatgtacacg    3540
gcactttcta gagccaccga taggattcac ttcgtgaaca caagtgcaaa ttcctctgcc    3600
ttctgggaaa agttggacag cacccctac ctcaagactt tcctatcagt ggtgagagaa     3660
caagcactca gggagtacga gccggcagag gcagagccaa ttcaagagcc tgagccccag    3720
acacacatgt gtgtcgagaa tgaggagtcc gtgctagaag agtacaaaga ggaactcttg    3780
gaaaagtttg acagagagat ccactctgaa tcccatggtc attcaaactg tgtccaaact    3840
gaagacacaa ccattcagtt gttttcgcat caacaagcaa aagatgagac tctcctctgg    3900
gcgactatag atgcgcggct caagaccagc aatcaagaaa caaacttccg agaattcctg    3960
agcaagaagg acattgggga cgttctgttt ttaaactacc aaaaagctat gggtttaccc    4020
aaagagcgta ttcctttttc caagaggtc tgggaagctt gtgcccacga agtacaaagc     4080
aagtacctca gcaagtcaaa gtgcaacttg atcaatggga ctgtgagaca gagcccagac    4140
ttcgatgaaa ataagattat ggtattcctc aagtcgcagt gggtcacaaa ggtgaaaaa     4200
ctaggtctac ccaagattaa gccaggtcaa accatagcag ccttttacca gcagactgtg    4260
atgctttttg gaactatggc taggtacatg cgatggttca gacaggcttt ccagccaaaa    4320
```

-continued

```
gaagtcttca taaactgtga gacgacgcca gatgacatgt ctgcatgggc cttgaacaac    4380
tggaatttca gcagacctag cttggctaat gactacacag ctttcgacca gtctcaggat    4440
ggagccatgt tgcaatttga ggtgctcaaa gccaaacacc actgcatacc agaggaaatc    4500
attcaggcat acatagatat taagactaat gcacagattt tcctaggcac gttatcaatt    4560
atgcgcctga ctggtgaagg tcccactttt gatgcaaaca ctgagtgcaa catagcttac    4620
acccatacaa agtttgacat cccagccgga actgctcaag tttatgcagg agacgactcc    4680
gcactggact gtgttccaga agtgaagcat agtttccaca ggcttgagga caaattactc    4740
ctaaagtcaa agcctgtaat cacgcagcaa aagaagggca gttggcctga gttttgtggt    4800
tggctgatca caccaaaagg ggtgatgaaa gacccaatta agctccatgt tagcttaaaa    4860
ttggctgaag ctaagggtga actcaagaaa tgtcaagatt cctatgaaat tgatctgagt    4920
tatgcctatg accacaagga ctctctgcat gacttgttcg atgagaaaca gtgtcaggca    4980
cacacactca cttgcagaac actaatcaag tcagggagag gcactgtctc actttcccgc    5040
ctcagaaact ttctttaacc gttaagttac cttagagatt tgaataagat gtcagcacca    5100
gctagtacaa cacagcccat agggtcaact acctcaacta ccacaaaaac tgcaggcgca    5160
actcctgcca cagcttcagg cctgttcact atcccggatg gggatttctt tagtacagcc    5220
cgtgccatag tagccagcaa tgctgtcgca acaaatgagg acctcagcaa gattgaggct    5280
atttggaagg acatgaaggt gcccacagac actatgcac aggctgcttg ggacttagtc    5340
agacactgtg ctgatgtagg atcatccgct caaacagaaa tgatagatac aggtccctat    5400
tccaacggca tcagcagagc tagactggca gcagcaatta agaggtgtg cacacttagg    5460
caattttgca tgaagtatgc cccagtggta tggaactgga tgttaactaa caacagtcca    5520
cctgctaact ggcaagcaca aggtttcaag cctgagcaca aattcgctgc attcgacttc    5580
ttcaatggag tcaccaaccc agctgccatc atgcccaaag aggggctcat ccggccaccg    5640
tctgaagctg aaatgaatgc tgcccaaact gctgcctttg tgaagattac aaaggccagg    5700
gcacaatcca acgactttgc cagcctagat gcagctgtca ctcgaggaag gatcaccgga    5760
acgaccacag cagaggcagt cgttactctg cctcctccat aacagaaact ttctttaacc    5820
gttaagttac cttagagatt tgaataagat ggatattctc atcagtagtt tgaaaagttt    5880
aggttattct aggacttcca aatctttaga ttcaggacct ttggtagtac atgcagtagc    5940
cggagccggt aagtccacag ccctaaggaa gttgatcctc agacacccaa cattcaccgt    6000
gcatacactc ggtgtccctg acaaggtgag tatcagaact agaggcatac agaagccagg    6060
acctattcct gagggcaact tcgcaatcct cgatgagtat actttggaca acaccacaag    6120
gaactcatac caggcacttt tgctgacccc ttatcaggca ccggagttta gcctagagcc    6180
ccacttctac ttggaaacat catttcgagt tccgaggaaa gtggcagatt tgatagctgg    6240
ctgtggcttc gatttcgaga cgaactcacc ggaagaaggg cacttagaga tcactggcat    6300
attcaaaggg cccctactcg gaaaggtgat agccattgat gaggagtctg agacaacact    6360
gtccaggcat ggtgttgagt ttgttaagcc ctgccaagtg acgggacttg agttcaaagt    6420
agtcactatt gtgtctgccg caccaatada ggaaattggc cagtccacag ctttctacaa    6480
cgctatcacc aggtcaaagg gattgacata tgtccgcgca gggccatagg ctgaccgctc    6540
cggtcaattc tgaaaaagtg tacatagtat taggtctatc atttgcttta gtttcaatta    6600
cctttctgct ttctagaaat agcttacccc acgtcggtga caacattcac agcttgccac    6660
acggaggagc ttacagagac ggcaccaaag caatcttgta caactcccca aatctagggt    6720
```

-continued

| | |
|---|---|
| cacgagtgag tctacacaac ggaaagaacg cagcatttgc tgccgttttg ctactgactt | 6780 |
| tgctgatcta tggaagtaaa tacatatctc aacgcaatca tacttgtgct tgtggtaaca | 6840 |
| atcatagcag tcattagcac ttccttagtg aggactgaac cttgtgtcat caagattact | 6900 |
| ggggaatcaa tcacagtgtt ggcttgcaaa ctagatgcag aaaccataag gccattgcc | 6960 |
| gatctcaagc cactctccgt tgaacggtta agtttccatt gatactcgaa agaggtcagc | 7020 |
| accagctagc aacaaacaag aacatgagag acctcgcgat ttaaatcgat ggtctcagat | 7080 |
| cggtcgtatc actggaacaa caaccgctga ggctgttgtc actctaccac caccataact | 7140 |
| acgtctacat aaccgacgcc tacccagtt tcatagtatt ttctggtttg attgtatgaa | 7200 |
| taatataaat aaaaaaaaaa aaaaaaaaaa aaaactagtg agctcttctg tcagcgggcc | 7260 |
| cactgcatcc accccagtac attaaaaacg tccgcaatgt gttattaagt tgtctaagcg | 7320 |
| tcaatttgtt tacaccacaa tatatcctgc caccagccag ccaacagctc cccgaccggc | 7380 |
| agctcggcac aaaatcacca ctcgatacag gcagcccatc ag | 7422 |

<210> SEQ ID NO 5
<211> LENGTH: 8394
<212> TYPE: DNA
<213> ORGANISM: Artificial Sequence
<220> FEATURE:
<223> OTHER INFORMATION: pNMD11740

<400> SEQUENCE: 5

| | |
|---|---|
| cctgtggttg gcacatacaa atggacgaac ggataaacct ttttcacgccc ttttaaatat | 60 |
| ccgattattc taataaacgc tcttttctct taggtttacc cgccaatata tcctgtcaaa | 120 |
| cactgatagt ttaaactgaa ggcgggaaac gacaatctga tctaagctag gcatgcctgc | 180 |
| aggtcaacat ggtggagcac gacacgcttg tctactccaa aaatatcaaa gatacagtct | 240 |
| cagaagacca agggcaatt gagactttc aacaagggt aatatccgga aacctcctcg | 300 |
| gattccattg cccagctatc tgtcacttta ttgtgaagat agtggaaaag gaaggtggct | 360 |
| cctacaaatg ccatcattgc gataaaggaa aggccatcgt tgaagatgcc tctgccgaca | 420 |
| gtggtcccaa agatggaccc ccacccacga ggagcatcgt ggaaaaagaa gacgttccaa | 480 |
| ccacgtcttc aaagcaagtg gattgatgtg atatctccac tgacgtaagg gatgacgcac | 540 |
| aatcccacta tccttcgcaa gacccttcct ctatataagg aagttcattt catttggaga | 600 |
| ggagaaaact aaaccataca ccaccaacac aaccaaaccc accacgccca attgttacac | 660 |
| acccgcttga aaagaaagt ttaacaaatg gccaaggtgc gcgaggttta ccaatctttt | 720 |
| acagactcca ccacaaaac tctcatccaa gatgaggctt atagaaacat cgcccccatc | 780 |
| atggaaaaac acaaactagc taaccccttac gctcaaacgg ttgaagcggc taatgatcta | 840 |
| gagggggttcg gcatagccac caatccctat agcattgaat tgcatacaca tgcagccgct | 900 |
| aagaccatag agaataaact tctagaggtg cttggttcca tcctaccaca gaacctgtt | 960 |
| acatttatgt ttcttaaacc cagaaagcta aactacatga aagaaaccc gcggatcaag | 1020 |
| gacatttttcc aaaatgttgc cattgaacca agagacgtag ccaggtaccc caaggaaaca | 1080 |
| ataattgaca aactcacaga gatcacaacg gaaacagcat acattagtga cactctgcac | 1140 |
| ttcttggatc cgagctacat agtggagaca ttccaaaact gcccaaaatt gcaaacattg | 1200 |
| tatgcgacct tagttctccc cgttgaggca gcctttaaaa tggaaagcac tcacccgaac | 1260 |
| atatacagcc tcaaatactt cggagatggt ttccagtata taccaggcaa ccatggtggc | 1320 |
| ggggcatacc atcatgaatt cgctcatcta caatggctca aagtgggaaa gatcaagtgg | 1380 |

```
agggacccca aggatagctt tctcggacat ctcaattaca cgactgagca ggttgagatg   1440
cacacagtga cagtacagtt gcaggaatcg ttcgcggcaa accacttgta ctgcatcagg   1500
agaggagact tgctcacacc ggaggtgcgc actttcggcc aacctgacag gtacgtgatt   1560
ccaccacaga tcttcctccc aaaagttcac aactgcaaga agccgattct caagaaaact   1620
atgatgcagc tcttcttgta tgttaggaca gtcaaggtcg caaaaaattg tgacattttt   1680
gccaaagtca gacaattaat taaatcatct gacttggaca aatactctgc tgtgaactg    1740 gtttacttag taagctacat ggagttcctt gccgatttac aagctaccac ctgcttctca   1800
gacacacttt ctggtggctt gctaacaaag accccttgcac cggtgagggc ttggatacaa   1860
gagaaaaaga tgcagctgtt tggtcttgag gactacgcga agttagtcaa agcagttgat   1920
ttccacccgg tggattttc tttcaaagtg gaaacttggg acttcagatt ccacccttg    1980 caagcgtgga aagccttccg accaagggaa gtgtcggatg tagaggaaat ggaaagtttg   2040
ttctcagatg gggacctgct tgattgcttc acaagaatgc cagcttatgc ggtaaacgca   2100
gaggaagatt tagctgcaat caggaaaacg cccgagatgg atgtcggtca agaagttaaa   2160
gagcctgcag gagacagaaa tcaatactca aaccctgcag aaactttcct caacaagctc   2220
cacaggaaac acagtaggga ggtgaaacac caggccgcaa agaaagctaa acgcctagct   2280
gaaatccagg agtcaatgag agctgaaggt gatgccgaac caaatgaaat aagcgggacg   2340
atgggggcaa tacccagcaa cgccgaactt cctggcacga atgatgccag acaagaactc   2400
acactcccaa ccactaaacc tgtccctgca aggtgggaag atgcttcatt cacagattct   2460 agtgtgaag aggagcaggt taaactcctt ggaaaagaaa ccgttgaaac agcgacgcaa    2520
caagtcatcg aaggacttcc ttggaaacac tggattcctc aattaaatgc tgttggattc   2580
aaggcgctgg aaattcagag ggataggagt ggaacaatga tcatgcccat cacagaaatg   2640
gtgtccgggc tggaaaaaga ggacttccct gaaggaactc caaaagagtt ggcacgagaa   2700
ttgttcgcta tgaacagaag ccctgccacc atcccctttgg acctgcttag agccagagac   2760
tacggcagtg atgtaaagaa caagagaatt ggtgccatca caagacaca ggcaacgagt    2820 tggggcgaat acttgacagg aaagatagaa agcttaactg agaggaaagt tgcgacttgt   2880
gtcattcatg gagctggagg ttctggaaaa agtcatgcca tccagaaggc attgagagaa   2940
attggcaagg gctcggacat cactgtagtc ctgccgacca atgaactgcg gctagattgg   3000
agtaagaaag tgcctaacac tgagccctat atgttcaaga cctctgaaaa ggcgttaatt   3060 ggggaacag gcagcatagt catctttgac gattactcaa aacttcctcc cggttacata    3120
gaagccttag tctgtttcta ctctaaaatc aagctaatca ttctaacagg agatagcaga   3180
caaagcgtct accatgaaac tgctgaggac gcctccatca ggcatttggg accagcaaca   3240
gagtacttct caaaatactg ccgatactat ctcaatgcca cacaccgcaa caagaaagat   3300
cttgcgaaca tgcttggtgt ctacagtgag agaacgggag tcaccgaaat cagcatgagc   3360
gccgagttct tagaaggaat cccaactttg gtaccctcgg atgagaagag aaagctgtac   3420
atgggcaccg ggaggaatga cacgttcaca tacgctggat gccagggggct aactaagccg   3480 aaggtacaaa tagtgttgga ccacaacacc caagtgtgta gcgcgaatgt gatgtacacg   3540
gcactttcta gagccaccga taggattcac ttcgtgaaca caagtgcaaa ttcctctgcc   3600
ttctgggaaa agttggacag cacccttac ctcaagactt tcctatcagt ggtgagagaa    3660
caagcactca gggagtacga gccggcagag gcagagccaa ttcaagagcc tgagccccag   3720
acacacatgt gtgtcgagaa tgaggagtcc gtgctagaag agtacaaaga ggaactcttg   3780
```

```
gaaaagtttg acagagagat ccactctgaa tcccatggtc attcaaactg tgtccaaact    3840
gaagacacaa ccattcagtt gttttcgcat caacaagcaa aagatgagac tctcctctgg    3900
gcgactatag atgcgcggct caagaccagc aatcaagaaa caaacttccg agaattcctg    3960
agcaagaagg acattgggga cgttctgttt ttaaactacc aaaaagctat gggtttaccc    4020
aaagagcgta ttccttttc ccaagaggtc tgggaagctt gtgcccacga agtacaaagc    4080
aagtacctca gcaagtcaaa gtgcaacttg atcaatggga ctgtgagaca gagcccagac    4140
ttcgatgaaa ataagattat ggtattcctc aagtcgcagt gggtcacaaa ggtggaaaaa    4200
ctaggtctac ccaagattaa gccaggtcaa accatagcag ccttttacca gcagactgtg    4260
atgcttttg gaactatggc taggtacatg cgatggttca gacaggcttt ccagccaaaa    4320
gaagtcttca taaactgtga gacgacgcca gatgacatgt ctgcatgggc cttgaacaac    4380
tggaatttca gcagacctag cttggctaat gactacacag ctttcgacca gtctcaggat    4440
ggagccatgt tgcaatttga ggtgctcaaa gccaaacacc actgcatacc agaggaaatc    4500
attcaggcat acatagatat taagactaat gcacagattt tcctaggcac gttatcaatt    4560
atgcgcctga ctggtgaagg tcccacttt gatgcaaaca ctgagtgcaa catagcttac    4620
acccatacaa agtttgacat cccagccgga actgctcaag tttatgcagg agacgactcc    4680
gcactggact gtgttccaga agtgaagcat agtttccaca ggcttgagga caaattactc    4740
ctaaagtcaa agcctgtaat cacgcagcaa agaagggca gttggcctga gttttgtggt    4800
tggctgatca caccaaaagg ggtgatgaaa gacccaatta agctccatgt tagcttaaaa    4860
ttggctgaag ctaagggtga actcaagaaa tgtcaagatt cctatgaaat tgatctgagt    4920
tatgcctatg accacaagga ctctctgcat gacttgttcg atgagaaaca gtgtcaggca    4980
cacacactca cttgcagaac actaatcaag tcagggagag gcactgtctc actttcccgc    5040
ctcagaaaact ttcttaacc gttaagttac cttagagatt tgaataagat gtcagcacca    5100
gctagtacaa cacagcccat agggtcaact acctcaacta ccacaaaaac tgcaggcgca    5160
actcctgcca cagcttcagg cctgttcact atcccggatg gggattcctt tagtacagcc    5220
cgtgccatag tagccagcaa tgctgtcgca caaatgagg acctcagcaa gattgaggct    5280
atttggaagg acatgaaggt gcccacagac actatggcac aggctgcttg ggacttagtc    5340
agacactgtg ctgatgtagg atcatccgct caaacagaaa tgatagatac aggtccctat    5400
tccaacggca tcagcagagc tagactggca gcagcaatta aagaggtgtg cacacttagg    5460
caattttgca tgaagtatgc cccagtggta tggaactgga tgttaactaa caacagtcca    5520
cctgctaact ggcaagcaca aggtttcaag cctgagcaca aattcgctgc attcgacttc    5580
ttcaatggag tcaccaaccc agctgccatc atgcccaaag aggggctcat ccggccaccg    5640
tctgaagctg aaatgaatgc tgcccaaact gctgcctttg tgaagattac aaaggccagg    5700
gcacaatcca acgactttgc cagcctagat gcagctgtca ctcgaggaag gatcaccgga    5760
acgaccacag cagaggcagt cgttactctg cctcctccat aacagaaact ttctttaacc    5820
gttaagttac cttagagatt tgaataagat ggatattctc atcagtagtt tgaaaagttt    5880
aggttattct aggacttcca aatctttaga ttcaggacct ttggtagtac atgcagtagc    5940
cggagccggt aagtccacag ccctaaggaa gttgatcctc agacacccaa cattcaccgt    6000
gcatacactc ggtgtccctg acaaggtgag tatcagaact agaggcatac agaagccagg    6060
acctattcct gagggcaact tcgcaatcct cgatgagtat actttggaca acaccacaag    6120
gaactcatac caggcacttt ttgctgaccc ttatcaggca ccggagttta gcctagagcc    6180
```

```
ccacttctac ttggaaacat catttcgagt tccgaggaaa gtggcagatt tgatagctgg      6240
ctgtggcttc gatttcgaga cgaactcacc ggaagaaggg cacttagaga tcactggcat      6300
attcaaaggg cccctactcg gaaaggtgat agccattgat gaggagtctg agacaacact      6360
gtccaggcat ggtgttgagt tgttaagcc ctgccaagtg acgggacttg agttcaaagt       6420
agtcactatt gtgtctgccg caccaataga ggaaattggc cagtccacag ctttctacaa      6480
cgctatcacc aggtcaaagg gattgacata tgtccgcgca gggccatagg ctgaccgctc      6540
cggtcaattc tgaaaaagtg tacatagtat taggtctatc atttgcttta gtttcaatta      6600
cctttctgct ttctagaaat agcttacccc acgtcggtga caacattcac agcttgccac      6660
acggaggagc ttacagagac ggcaccaaag caatcttgta caactcccca aatctagggt      6720
cacgagtgag tctacacaac ggaaagaacg cagcatttgc tgccgttttg ctactgactt      6780
tgctgatcta tggaagtaaa tacatatctc aacgcaatca tacttgtgct tgtggtaaca      6840
atcatagcag tcattagcac ttccttagtg aggactgaac cttgtgtcat caagattact      6900
ggggaatcaa tcacagtgtt ggcttgcaaa ctagatgcag aaaccataag ggccattgcc      6960
gatctcaagc cactctccgt tgaacggtta agtttccatt gatactcgaa agaggtcagc      7020
accagctagc aacaaacaag aacatggaaa cccttactgt gcacgctcct agcccttcta      7080
ctaaccttcc ttcttacggt aacggtgctt tcagcctgtc tgctcctcat gttcctggtg      7140
ctggtccttt gcttgttcag gtggtgtaca gcttcttcca gagccctaat atgtgccttc      7200
aggctcttac ccagcttgag gattacatca agaaacacgg tgctagcaac cctctgaccc      7260
tgcagattat ctctaccaat ataggtaaat ttctagtttt tctccttcat tttcttggtt      7320
aggaccctttt tctctttttta tttttttgag ctttgatctt tctttaaact gatctatttt    7380
ttaattgatt ggttatggtg taaatattac atagctttaa ctgataatct gattacttta     7440
tttcgtgtgt ctatgatgat gatgataact gcaggttatt tctgcaacgc tgataggaac     7500
cttgtgctgc accctggtat ctctgtgtac gatgcttacc acttcgctaa gcctgctcca     7560
agccagtacg attacagatc catgaacatg aagcagatga gcggtaacgt gaccaccct      7620
attgtggctc ttgctcatta cctttgggga acggtgctg agagaagcgt gaacattgct      7680
aatatcggtc tgaagatcag ccctatgaag atcaaccaga tcaaggatat catcaagagc      7740
ggtgtggtgg gaaccttccc tgtgtctact aagttcactc acgctaccgg tgattacaac      7800
gtgatcaccg gtgcttacct gggtaacatc actcttaaga ccgagggaac cctgaccatc      7860
tctgctaatg gttcttggac ctacaatggt gtggtgcgtt cctacgatga taagtacgat     7920
ttcaacgcta gcacccacag gggtatcatt ggtgagtctc ttactaggct gggtgctatg      7980
ttcagcggta agagtaccaa gattctgctg cctggtgaga tccacatcaa agagtctggt      8040
aagaggtaag atcggtcgta tcactggaac aacaaccgct gaggctgttg tcactctacc      8100
accaccataa ctacgtctac ataaccgacg cctaccccag tttcatagta ttttctggtt      8160
tgattgtatg aataatataa ataaaaaaaa aaaaaaaaa aaaaactag tgagctcttc        8220
tgtcagcggg cccactgcat ccaccccagt acattaaaaa cgtccgcaat gtgttattaa      8280
gttgtctaag cgtcaatttg tttacaccac aatatatcct gccaccagcc agccaacagc      8340
tccccgaccg gcagctcggc acaaaatcac cactcgatac aggcagccca tcag            8394
```

<210> SEQ ID NO 6
<211> LENGTH: 576
<212> TYPE: PRT
<213> ORGANISM: Escherichia coli

```
<400> SEQUENCE: 6

Met Ser Gly Gly Asp Gly Arg Gly His Asn Ser Gly Ala His Asn Thr
1               5                   10                  15

Gly Gly Asn Ile Asn Gly Gly Pro Thr Gly Leu Gly Gly Asn Gly Gly
            20                  25                  30

Ala Ser Asp Gly Ser Gly Trp Ser Glu Asn Asn Pro Trp Gly Gly
        35                  40                  45

Gly Ser Gly Ser Gly Val His Trp Gly Gly Ser Gly His Gly Asn
    50                  55                  60

Gly Gly Gly Asn Ser Asn Ser Gly Gly Ser Asn Ser Ser Val Ala
65              70                  75                  80

Ala Pro Met Ala Phe Gly Phe Pro Ala Leu Ala Ala Pro Gly Ala Gly
                85                  90                  95

Thr Leu Gly Ile Ser Val Ser Gly Glu Ala Leu Ser Ala Ala Ile Ala
            100                 105                 110

Asp Ile Phe Ala Ala Leu Lys Gly Pro Phe Lys Phe Ser Ala Trp Gly
        115                 120                 125

Ile Ala Leu Tyr Gly Ile Leu Pro Ser Glu Ile Ala Lys Asp Asp Pro
    130                 135                 140

Asn Met Met Ser Lys Ile Val Thr Ser Leu Pro Ala Glu Thr Val Thr
145                 150                 155                 160

Asn Val Gln Val Ser Thr Leu Pro Leu Asp Gln Ala Thr Val Ser Val
                165                 170                 175

Thr Lys Arg Val Thr Asp Val Val Lys Asp Thr Arg Gln His Ile Ala
            180                 185                 190

Val Val Ala Gly Val Pro Met Ser Val Pro Val Val Asn Ala Lys Pro
        195                 200                 205

Thr Arg Thr Pro Gly Val Phe His Ala Ser Phe Pro Gly Val Pro Ser
    210                 215                 220

Leu Thr Val Ser Thr Val Lys Gly Leu Pro Val Ser Thr Thr Leu Pro
225                 230                 235                 240

Arg Gly Ile Thr Glu Asp Lys Gly Arg Thr Ala Val Pro Ala Gly Phe
                245                 250                 255

Thr Phe Gly Gly Gly Ser His Glu Ala Val Ile Arg Phe Pro Lys Glu
            260                 265                 270

Ser Gly Gln Lys Pro Val Tyr Val Ser Val Thr Asp Val Leu Thr Pro
        275                 280                 285

Ala Gln Val Lys Gln Arg Gln Asp Glu Glu Lys Arg Leu Gln Gln Glu
    290                 295                 300

Trp Asn Asp Ala His Pro Val Glu Val Ala Glu Arg Asn Tyr Glu Gln
305                 310                 315                 320

Ala Arg Ala Glu Leu Asn Gln Ala Asn Lys Asp Val Ala Arg Asn Gln
                325                 330                 335

Glu Arg Gln Ala Lys Ala Val Gln Val Tyr Asn Ser Arg Lys Ser Glu
            340                 345                 350

Leu Asp Ala Ala Asn Lys Thr Leu Ala Asp Ala Lys Ala Glu Ile Lys
        355                 360                 365

Gln Phe Glu Arg Phe Ala Arg Glu Pro Met Ala Ala Gly His Arg Met
    370                 375                 380

Trp Gln Met Ala Gly Leu Lys Ala Gln Arg Ala Gln Thr Asp Val Asn
385                 390                 395                 400

Asn Lys Lys Ala Ala Phe Asp Ala Ala Lys Glu Lys Ser Asp Ala
                405                 410                 415
```

```
Asp Val Ala Leu Ser Ser Ala Leu Glu Arg Arg Lys Gln Lys Glu Asn
            420                 425                 430

Lys Glu Lys Asp Ala Lys Ala Lys Leu Asp Lys Glu Ser Lys Arg Asn
        435                 440                 445

Lys Pro Gly Lys Ala Thr Gly Lys Gly Lys Pro Val Asn Asn Lys Trp
    450                 455                 460

Leu Asn Asn Ala Gly Lys Asp Leu Gly Ser Pro Val Pro Asp Arg Ile
465                 470                 475                 480

Ala Asn Lys Leu Arg Asp Lys Glu Phe Lys Ser Phe Asp Asp Phe Arg
                485                 490                 495

Lys Lys Phe Trp Glu Glu Val Ser Lys Asp Pro Glu Leu Ser Lys Gln
            500                 505                 510

Phe Ser Arg Asn Asn Asn Asp Arg Met Lys Val Gly Lys Ala Pro Lys
        515                 520                 525

Thr Arg Thr Gln Asp Val Ser Gly Lys Arg Thr Ser Phe Glu Leu His
    530                 535                 540

His Glu Lys Pro Ile Ser Gln Asn Gly Gly Val Tyr Asp Met Asp Asn
545                 550                 555                 560

Ile Ser Val Val Thr Pro Lys Arg His Ile Asp Ile His Arg Gly Lys
                565                 570                 575

<210> SEQ ID NO 7
<211> LENGTH: 626
<212> TYPE: PRT
<213> ORGANISM: Escherichia coli

<400> SEQUENCE: 7

Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Leu Arg Glu Tyr
    130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
            180                 185                 190

Ala Gln Asn Ala Asp Lys Lys Ala Ala Asp Met Leu Ala Glu Tyr Glu
        195                 200                 205

Arg Arg Lys Gly Ile Leu Asp Thr Arg Leu Ser Glu Leu Glu Lys Asn
    210                 215                 220
```

```
Gly Gly Ala Ala Leu Ala Val Leu Asp Ala Gln Ala Arg Leu Leu
225                 230                 235                 240

Gly Gln Gln Thr Arg Asn Asp Arg Ala Ile Ser Glu Ala Arg Asn Lys
                245                 250                 255

Leu Ser Ser Val Thr Glu Ser Leu Asn Thr Ala Arg Asn Ala Leu Thr
                260                 265                 270

Arg Ala Glu Gln Gln Leu Thr Gln Gln Lys Asn Thr Pro Asp Gly Lys
            275                 280                 285

Thr Ile Val Ser Pro Glu Lys Phe Pro Gly Arg Ser Ser Thr Asn His
290                 295                 300

Ser Ile Val Val Ser Gly Asp Pro Arg Phe Ala Gly Thr Ile Lys Ile
305                 310                 315                 320

Thr Thr Ser Ala Val Ile Asp Asn Arg Ala Asn Leu Asn Tyr Leu Leu
                325                 330                 335

Ser His Ser Gly Leu Asp Tyr Lys Arg Asn Ile Leu Asn Asp Arg Asn
                340                 345                 350

Pro Val Val Thr Glu Asp Val Glu Gly Asp Lys Lys Ile Tyr Asn Ala
            355                 360                 365

Glu Val Ala Glu Trp Asp Lys Leu Arg Gln Arg Leu Leu Asp Ala Arg
370                 375                 380

Asn Lys Ile Thr Ser Ala Glu Ser Ala Val Asn Ser Ala Arg Asn Asn
385                 390                 395                 400

Leu Ser Ala Arg Thr Asn Glu Gln Lys His Ala Asn Asp Ala Leu Asn
                405                 410                 415

Ala Leu Leu Lys Glu Lys Glu Asn Ile Arg Asn Gln Leu Ser Gly Ile
                420                 425                 430

Asn Gln Lys Ile Ala Glu Glu Lys Arg Lys Gln Asp Glu Leu Lys Ala
            435                 440                 445

Thr Lys Asp Ala Ile Asn Phe Thr Thr Glu Phe Leu Lys Ser Val Ser
450                 455                 460

Glu Lys Tyr Gly Ala Lys Ala Glu Gln Leu Ala Arg Glu Met Ala Gly
465                 470                 475                 480

Gln Ala Lys Gly Lys Lys Ile Arg Asn Val Glu Glu Ala Leu Lys Thr
                485                 490                 495

Tyr Glu Lys Tyr Arg Ala Asp Ile Asn Lys Lys Ile Asn Ala Lys Asp
            500                 505                 510

Arg Ala Ala Ile Ala Ala Leu Glu Ser Val Lys Leu Ser Asp Ile
                515                 520                 525

Ser Ser Asn Leu Asn Arg Phe Ser Arg Gly Leu Gly Tyr Ala Gly Lys
530                 535                 540

Phe Thr Ser Leu Ala Asp Trp Ile Thr Glu Phe Gly Lys Ala Val Arg
545                 550                 555                 560

Thr Glu Asn Trp Arg Pro Leu Phe Val Lys Thr Glu Thr Ile Ile Ala
                565                 570                 575

Gly Asn Ala Ala Thr Ala Leu Val Ala Leu Val Phe Ser Ile Leu Thr
                580                 585                 590

Gly Ser Ala Leu Gly Ile Ile Gly Tyr Gly Leu Leu Met Ala Val Thr
            595                 600                 605

Gly Ala Leu Ile Asp Glu Ser Leu Val Glu Lys Ala Asn Lys Phe Trp
610                 615                 620

Gly Ile
625
```

```
<210> SEQ ID NO 8
<211> LENGTH: 626
<212> TYPE: PRT
<213> ORGANISM: Escherichia coli

<400> SEQUENCE: 8

Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Pro Ala Trp Ser Ser
        35                  40                  45

Phe Gly Asn Lys Thr Ile Trp Gly Gly Asn Glu Trp Val Asp Asp Ser
50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
            180                 185                 190

Ala Gln Asn Ala Asp Lys Lys Ala Ala Asp Met Leu Ala Glu Tyr Glu
        195                 200                 205

Arg Arg Lys Gly Ile Leu Asp Thr Arg Leu Ser Glu Leu Glu Lys Asn
210                 215                 220

Gly Gly Ala Ala Leu Ala Val Leu Asp Ala Gln Gln Ala Arg Leu Leu
225                 230                 235                 240

Gly Gln Gln Thr Arg Asn Asp Arg Ala Ile Ser Glu Ala Arg Asn Lys
                245                 250                 255

Leu Ser Ser Val Thr Glu Ser Leu Lys Thr Ala Arg Asn Ala Leu Thr
            260                 265                 270

Arg Ala Glu Gln Gln Leu Thr Gln Gln Lys Asn Thr Pro Asp Gly Lys
        275                 280                 285

Thr Ile Val Ser Pro Glu Lys Phe Pro Gly Arg Ser Ser Thr Asn His
290                 295                 300

Ser Ile Val Val Ser Gly Asp Pro Arg Phe Ala Gly Thr Ile Lys Ile
305                 310                 315                 320

Thr Thr Ser Ala Val Ile Asp Asn Arg Ala Asn Leu Asn Tyr Leu Leu
                325                 330                 335

Thr His Ser Gly Leu Asp Tyr Lys Arg Asn Ile Leu Asn Asp Arg Asn
            340                 345                 350

Pro Val Val Thr Glu Asp Val Glu Gly Asp Lys Lys Ile Tyr Asn Ala
        355                 360                 365

Glu Val Ala Glu Trp Asp Lys Leu Arg Gln Arg Leu Leu Asp Ala Arg
370                 375                 380
```

-continued

```
Asn Lys Ile Thr Ser Ala Glu Ser Ala Ile Asn Ser Ala Arg Asn Asn
385                 390                 395                 400

Val Ser Ala Arg Thr Asn Glu Gln Lys His Ala Asn Asp Ala Leu Asn
                405                 410                 415

Ala Leu Leu Lys Glu Lys Glu Asn Ile Arg Ser Gln Leu Ala Asp Ile
            420                 425                 430

Asn Gln Lys Ile Ala Glu Glu Lys Arg Lys Arg Asp Glu Ile Asn Met
        435                 440                 445

Val Lys Asp Ala Ile Lys Leu Thr Ser Asp Phe Tyr Arg Thr Ile Tyr
    450                 455                 460

Asp Glu Phe Gly Lys Gln Ala Ser Glu Leu Ala Lys Glu Leu Ala Ser
465                 470                 475                 480

Val Ser Gln Gly Lys Gln Ile Lys Ser Val Asp Asp Ala Leu Asn Ala
            485                 490                 495

Phe Asp Lys Phe Arg Asn Asn Leu Asn Lys Lys Tyr Asn Ile Gln Asp
            500                 505                 510

Arg Met Ala Ile Ser Lys Ala Leu Glu Ala Ile Asn Gln Val His Met
            515                 520                 525

Ala Glu Asn Phe Lys Leu Phe Ser Lys Ala Phe Gly Phe Thr Gly Lys
530                 535                 540

Val Ile Glu Arg Tyr Asp Val Ala Val Glu Leu Gln Lys Ala Val Lys
545                 550                 555                 560

Thr Asp Asn Trp Arg Pro Phe Phe Val Lys Leu Glu Ser Leu Ala Ala
                565                 570                 575

Gly Arg Ala Ala Ser Ala Val Thr Ala Trp Ala Phe Ser Val Met Leu
            580                 585                 590

Gly Thr Pro Val Gly Ile Leu Gly Phe Ala Ile Ile Met Ala Ala Val
            595                 600                 605

Ser Ala Leu Val Asn Asp Lys Phe Ile Glu Gln Val Asn Lys Leu Ile
        610                 615                 620

Gly Ile
625
```

COLICINS FOR THE CONTROL OF EHEC

This patent application claims the priority of U.S. provisional patent application No. 62/166,379 filed on May 26, 2015 and of European patent application No. 15 181 133.8 filed on Aug. 14, 2015.

FIELD OF THE INVENTION

The invention provides a method of preventing or reducing contamination of food or other objects with enteropathogenic *E. coli* (EPEC) and/or enterohaemorrhagic *E. coli* (EHEC) and a use of colicin M or a derivative thereof for preventing or reducing contamination of food and other objects with EHEC. Further provided is colicin M or a derivative thereof for use in a method of treating or preventing infection with EHEC.

BACKGROUND OF THE INVENTION

*Escherichia coli* is a normal inhabitant of human gastrointestinal (GI) tract, however, some *E. coli* strains are pathogenic. Enterohaemorrhagic *E. coli* (EHEC) target the small and large bowels and can cause haemorrhagic colitis and HUS (haemolytic uraemic syndrome). STEC is an abbreviation for Shiga-toxin producing *E. coli*. EHEC strains are STEC strains. Shiga-toxin (Stx) acts on the lining of the blood vessels and the vascular endothelium. The toxin penetrates into endothelial cells. When inside the cell, Stx inactivate protein synthesis leading to the death of the cell. The vascular endothelium has to continually renew itself, so this killing of cells leads to a breakdown of the lining and to hemorrhage. The first response is commonly a bloody diarrhea.

The toxin is effective against small blood vessels, such as found in the digestive tract, the kidney, and lungs, but not against large vessels such as the arteries or major veins. A specific target for the toxin appears to be the vascular endothelium of the glomerulus in the kidneys. Destroying these structures leads to kidney failure and the development of the often deadly and frequently debilitating HUS. Food poisoning with Shiga toxin often also has effects on the lungs and the nervous system.

A large number of serotypes of STEC isolated from humans is known. From studies in the USA and Canada examining human STEC infections, 50-80% were identified as being caused by *E. coli* O157:H7. 30 to 50% are caused by non-O157 STEC. Although *E. coli* O157:H7 has been most commonly identified as the cause of STEC infection, isolation of non-O157 STEC strains from clinical cases, outbreaks and environmental sources has been increasing (Posse et al., FEMS Microbiol Lett. 2008; 282(1):124-31; Possé et al., J. Appl. Microbiol. 2008; 105(1):227-35). A study at the Center for Disease Control and Prevention showed that from 1983-2002 approximately 70% of non-O157 STEC infections in the United States were caused by strains from one of six major serogroups, namely O26, O45, O103, O111, O121 and O145 (Brooks et al., 2005). Virulence factors for non-O157 STEC include, but are not limited to, production of the shiga-like toxins 1 and/or 2 (Stx1, Stx2) and intimin (eae). USDA-FSIS (United States Department of Agriculture (USDA) and Food Safety and Inspection Service (FSIS)) defined the so-called "Big 7" STEC panel: O26, O45, O103, O111, O121 and O145 serotypes. These are considered as most dangerous STEC serotypes ("adulterants"). EHEC serotypes are generally classified using the O antigen which is a part of the lipopolysaccharide layer, and the H antigen that is flagellin.

Prevention of EHEC or reducing contamination of food with EHEC requires, according to the WHO, control measures at all stages of the food chain, from agricultural production on the farm to processing, manufacturing and preparation of foods in both commercial establishments and household kitchens. As to industry, the WHO recommends that the number of cases of disease might be reduced by various mitigation strategies for ground beef (for example, screening the animals pre-slaughter to reduce the introduction of large numbers of pathogens in the slaughtering environment). Good hygienic slaughtering practices reduce contamination of carcasses by faeces, but do not guarantee the absence of EHEC from products. Education in hygienic handling of foods for workers at farms, abattoirs and those involved in the food production is essential to keep microbiological contamination to a minimum. So far, the only effective method of eliminating EHEC from foods is to introduce a bactericidal treatment, such as heating (e.g. cooking, pasteurization) or irradiation (see: http://www.who.int/mediacentre/factsheets/fs125/en/).

Treatment of EHEC infections in humans is difficult. A multitargeted approach is generally recommended including general supportive measures, anti-platelet and thrombolytic agents and thrombin inhibitor, selective use of antimicrobials, probiotics, toxin neutralizers and antibodies against key pathogenic pathway elements (Goldwater et al., BMC Medicine 2012, 10:12).

Most of the above mentioned methods of preventing EHEC or reducing contamination with EHEC are methods that are essentially independent from a particular pathogenic bacterium or from a particular serotype of EHEC. This has the advantage that little prior knowledge of the specific EHEC serotype in question is necessary before countermeasures are taken. However, the above mentioned methods of preventing EHEC or reducing contamination with EHEC such as heating or irradiation are not always applicable or change the treated good or food in undesirable ways. Other methods may have turned out non-effective with a particular patient. There is therefore a need for further methods of preventing or treating EHEC infections or methods for reducing or preventing contamination of objects with EHEC.

It is an object of the invention to provide methods for preventing or treating EHEC infections such as food-borne EHEC infections. It is another object to provide methods for preventing or reducing contamination of objects, notably, food with EHEC. It is a further object to provide methods for preventing or treating EHEC infections and/or methods for reducing contamination of objects with EHEC, that are effective against a wide range of EHEC serogroups such as the Big 7 or Big 6 groups of serotypes.

SUMMARY OF THE INVENTION

This problem has been solved by the following:
(1) A method of preventing or reducing contamination of an object such as food with EPEC or enterohaemorrhagic *E. coli* (EHEC), comprising contacting said object with colicin M or a derivative thereof.
(2) The method according to item 1, wherein contamination of an object such as food with EHEC serotype O157:H7 is prevented or reduced.
(3) The method according to item 1, wherein contamination of an object such as food with any one or all of the following *E. coli* serotypes is prevented or reduced: serotype O26:H11, serotype O45:H2, serotype O103:H11, serotype O111:H8, serotype O157:H7, and serotype O104:H4.

(4) The method according to item 1, wherein contamination of an object such as food with any one or all of the following *E. coli* serotypes is prevented or reduced: serotype O26:H11, serotype O45:H2, serotype O103:H11, serotype O111:H8, serotype O145:NM, serotype O157:H7, and serotype O104:H4.

(5) The method according to item 1, wherein said object is contacted with an aqueous solution of colicin M or its derivative by spraying with said aqueous solution or by dipping said object into said aqueous solution.

(6) The method according to item 1, wherein said food is immersed for at least 10 seconds, preferably for at least 1 minute, preferably for at least 5 minutes into an aqueous solution containing colicin M or its derivative.

(7) The method according to any one of items 1 to 6, wherein said colicin M or its derivative is produced by expression in a plant or in plant cells, followed by removing undesired components from said plant or said plant cells.

(8) The method according to any one of items 1 to 7, wherein said food is meat, raw fruit or raw vegetable.

(9) The method according to any one of items 1 to 8, wherein said colicin M has the amino acid sequence of SEQ ID NO: 1.

(10) The method according to any one of items 1 to 8, wherein the toxicity of the derivative of colicin M is such that the derivative and the colicin M of SEQ ID NO: 1 produce spots free of viable bacteria of sensitive *E. coli* strain DH10B of the same diameter 12 hours after spotting 5 microliters of a solution of said derivative of colicin M and the colicin M of SEQ ID NO: 1 onto a lawn of the sensitive *E. coli* strain on an agar plate and subsequent incubation of the agar plate at 37° C., wherein the concentration of the derivative of colicin M is at most 5 times that of the comparative solution of the colicin M of SEQ ID NO: 1.

(11) The method according to any one of items 1 to 10, wherein said derivative of colicin M comprises the C-terminal activity domain of residues 141 to 271 of colicin M or an activity domain having from 1 to 30, preferably from 1 to 20, amino acid substitutions, insertions and/or deletions compared to residues 141 to 271 of SEQ ID NO: 1.

(12) The method according to any one of items 1 to 11, wherein said derivative of colicin M comprises the central receptor-binding domain of residues 36 to 140 of colicin M or an activity domain having from 1 to 10 amino acid substitutions, insertions and/or deletions compared to residues 36 to 140 of SEQ ID NO: 1.

(13) The method according to any one of items 1 to 12, wherein said derivative of colicin M has amino acid residues 1 to 35 of SEQ ID NO: 1 or has from 1 to 8, preferably from 1 to 4, amino acid substitutions, insertions and/or deletions compared to residues 1 to 35 of SEQ ID NO: 1.

(14) The method according to any one of items 1 to 13, wherein said colicin M or its derivative is used in combination with one, several or all colicins selected from the group consisting of colE7, colB, colIa, colU, colK, and col5, or derivatives thereof; or said colicin M or its derivative is used in combination with colicin Ib.

(15) The method according to any one of items 1 to 13, wherein contamination with any one, several or all of the following *E. coli* serotypes is prevented or reduced: O26:H11, O45:H2, O103:H11, O111:H8, O145:NM, O157:H7, O104:H4, and O121:H19.

(16) A method of preventing or reducing contamination of an object such as food with EPEC or enterohaemorrhagic *E. coli* (EHEC), comprising contacting said object with colicin Ia or colicin Ib or a derivative thereof; preferably contamination of an object with EHEC O121:H19 is prevented or reduced.

(17) An object such as food treated with colicin M or a derivative thereof or treated with colicin Ia or colicin Ib or a derivative thereof.

(18) Use of colicin M or a derivative thereof or colicin Ib or a derivative thereof for the manufacture of a medicament for treating or preventing infection with EHEC.

(19) A composition such as an aqueous solution comprising colicin M or a derivative thereof.

(20) A composition such as an aqueous solution comprising colicin Ia or colicin Ib or derivatives thereof.

(21) The composition according to item 19 or 20, further comprising one or more further colicin selected from the group consisting of colM, colE7, colB, colIa, colU, colK, and col5, or a derivative of any of the before-mentioned colicins, preferably colM or colE7 or a derivative thereof.

(22) The composition according to item 19 or 21, further comprising one or more further colicin selected from the group consisting of colicin E5, colicin E8, colicin E9, colicin A, colicin S4, colicin 10, colicin R, colicin 28b, colicin Y, colicin Ia, colicin Ib, and cloacin DF13, or a derivative of colicin E5, colicin E8, colicin E9, colicin A, colicin S4, colicin 10, colicin R, colicin 28b, colicin Y, colicin Ib, and cloacin DF13; preferably cloacin DF13, colicin R or colicin Ib or derivatives thereof, more preferably colicin Ib or a derivative thereof.

(23) A composition such as an aqueous solution comprising any one or more colicin selected from colicin M, colicin E7, colicin B, colicin Ia, colicin U, colicin K, colicin 5, colicin E5, colicin E8, colicin E9, colicin A, colicin S4, colicin 10, colicin R, colicin 28b, colicin Y, colicin Ib, and cloacin DF13, or a derivative of colicin M, colicin E7, colicin B, colicin Ia, colicin U, colicin K, colicin 5, colicin E5, colicin E8, colicin E9, colicin A, colicin S4, colicin 10, colicin R, colicin 28b, colicin Y, colicin Ib, and cloacin DF13.

(24) A process of producing a purified colicin or a colicin-containing preparation, comprising:
(i) expressing said colicin in a plant from a nucleic acid construct encoding said colicin;
(ii) homogenizing the plant containing expressed colicin to produce a homogenate, optionally followed by removing solid or insoluble material;
(iii) acidifying the homogenate or a clarified fraction thereof to a pH of below pH5, followed by removal of insoluble material, to obtain a colicin-containing solution;
(iv) neutralizing the clarified colicin-containing solution, followed by removal of insoluble material;
(v) optionally concentrating the colicin-containing solution obtained in the previous step;
(vi) optionally freeze-drying the solutions obtained in step (iv) or (v) to obtain a freeze-dried preparation of said colicin.

(25) The process according to item 24, wherein said plant is an edible plant, such as beet, spinach, chicory or lettuce.

(26) The process according to item 24, further comprising purifying, subsequent to step (iv) or (v), said colicin by column chromatography, preferably by cation exchange chromatography.

(27) The process according to any one of items 24 to 26, wherein said colicin is colM, colE7, colB, colIa, colU, colK, col5, cloacin DF13, colicin R, colicin Ia, or colicin Ib or derivatives thereof; preferably colM, colE7, colicin Ia, or colicin Ib, or a derivative thereof, more preferably said colicin is colicin M or a derivative thereof.

(28) A method of preventing infection of a mammal with enterohaemorrhagic *E. coli*, comprising treating the mammal with colicin or a combination of colicins as described above.

(29) A use of a colicin or a combination of colicins as described above for the preparation of a medicament for preventing infection of a mammal with enterohaemorrhagic *E. coli*.

(30) A method for reducing the load of EHEC in ruminants such as cattle or sheep, comprising treating the ruminants with colicin or a combination of colicins as described above.

(31) A use of a colicin or a combination of colicins as described above for reducing the load of EHEC in ruminants such as cattle or sheep, comprising treating the ruminants with colicin or a combination of colicins as described above.

The invention also provides the use of colicin M or a derivative thereof (as defined herein) for reducing contamination of an object such as food with EHEC. The invention also provides the use of colicin Ia and/or Ib or a derivative thereof for reducing contamination of an object such as food with EHEC, notably EHEC strain O121:H19.

The inventors have surprisingly found a colicin having at the same time high activity against several EHEC serotypes and an exceptionally low specificity for particular EHEC strains or serotypes, i.e. a wide activity or toxicity against several EHEC strains. Thus, the invention allows preventing or reducing contamination of food and other objects with EHEC, generally without prior knowledge of the specific EHEC serotype having contaminated or that may contaminate the object. Further, the invention allows preventing an infection with EHEC in a patient.

BRIEF DESCRIPTION OF THE DRAWINGS

FIG. 1A shows colicin expression vectors pNMD15511, pNMD15521 and pNMD16121 for the expression of colicins E2, E3 and E6, respectively.

FIG. 1B shows colicin expression vectors pNMD8802, pNMD10221, pNMD3680, pNMD15252 and pNMD15291 for the expression of colicins E7, M, N, K and B, respectively.

FIG. 1C shows colicin expression vectors pNNMD15271, pNMD15311, pNMD19141 and pNMD19162 for the expression of colicins U, 5, Ia and D, respectively.

In FIGS. 1A-1C, RB and LB stand for the right and left borders of T-DNA of binary vectors. Pact2: promoter of *Arabidopsis* actin2 gene; o: 5' end from TVCV (turnip vein clearing virus); RdRp: RNA-dependent RNA polymerase open reading frame (ORF) from cr-TMV (crucifer-infecting tobamovirus); MP: movement protein ORF from cr-TMV; ColE2: colicin E2 coding sequence; ColE3: colicin E3 coding sequence; ColE6: colicin E6 coding sequence; ColM: colicin M coding sequence; ColN: colicin N coding sequence; ColK: colicin K coding sequence; ColB: colicin B coding sequence; ColU: colicin U coding sequence; Co15: colicin 5 coding sequence; ColIa: colicin Ia coding sequence; ColD: colicin D coding sequence; N: 3'-non-translated region from cr-TMV; T: *Agrobacterium* nopaline synthase terminator; white segments interrupting grey segments in the RdRp and MP ORFs indicate introns inserted into these ORFs for increasing the likelihood of RNA replicon formation in the cytoplasm of plant cells, which is described in detail in WO2005049839. An intron was also inserted into ColE2, ColE3, ColE6, ColE7, ColM and ColD ORFs for preventing the cytotoxic effect of these proteins on *E. coli* cells used for plasmid cloning.

Figure 10:
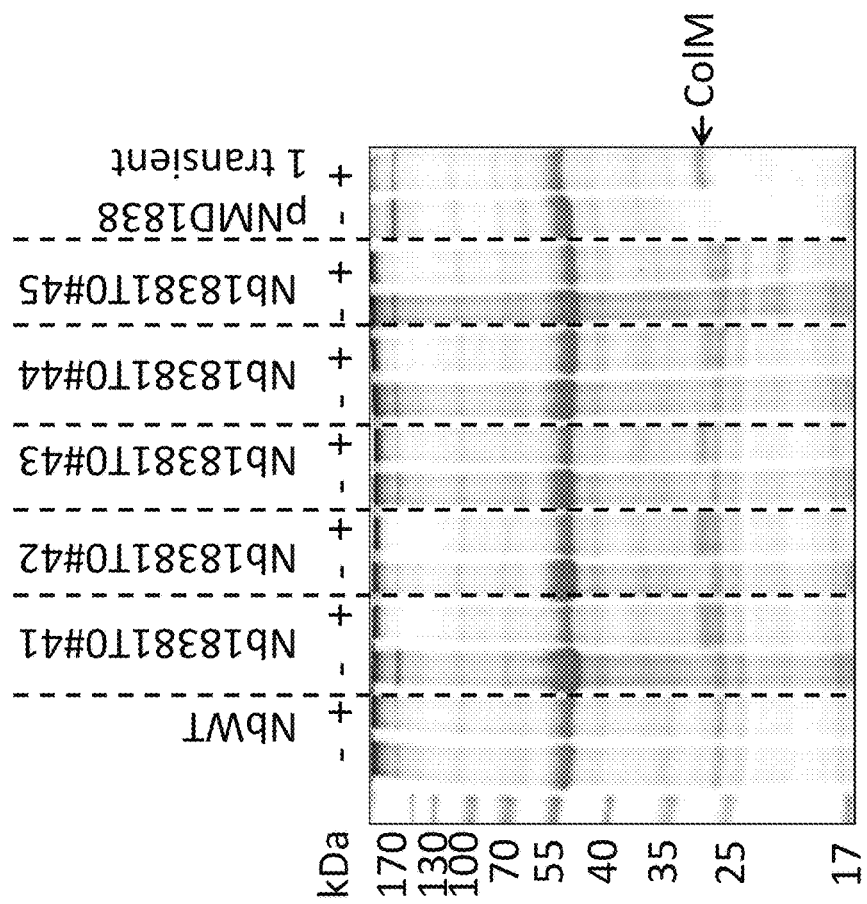

PVX-based vectors for the expression of immunity proteins include pNMD15231 and pNMD16141 for the expression of colicin E2 and colicin E6 immunity proteins, respectively (FIG. 1A), pNMD9060 for the expression of colicin E7 immunity protein (FIG. 1B), and pNMD15371 for the expression of colicin D immunity protein (FIG. 10). P35S: cauliflower mosaic virus 35S promoter; PVX-pot: RNA-dependent RNA polymerase from PVX; CP: coat protein ORF; 25K, 12K and 8 together indicate the 25KDA, 12 kDa and 8 kDa triple gene block modules from PVX; N: 3'-untranslated region from PVX. ImmE2, ImmE6, ImmE7 and ImmD stand for coding sequences of colicins E2, E6, E7 and D immunity proteins, respectively.

Figure 2:
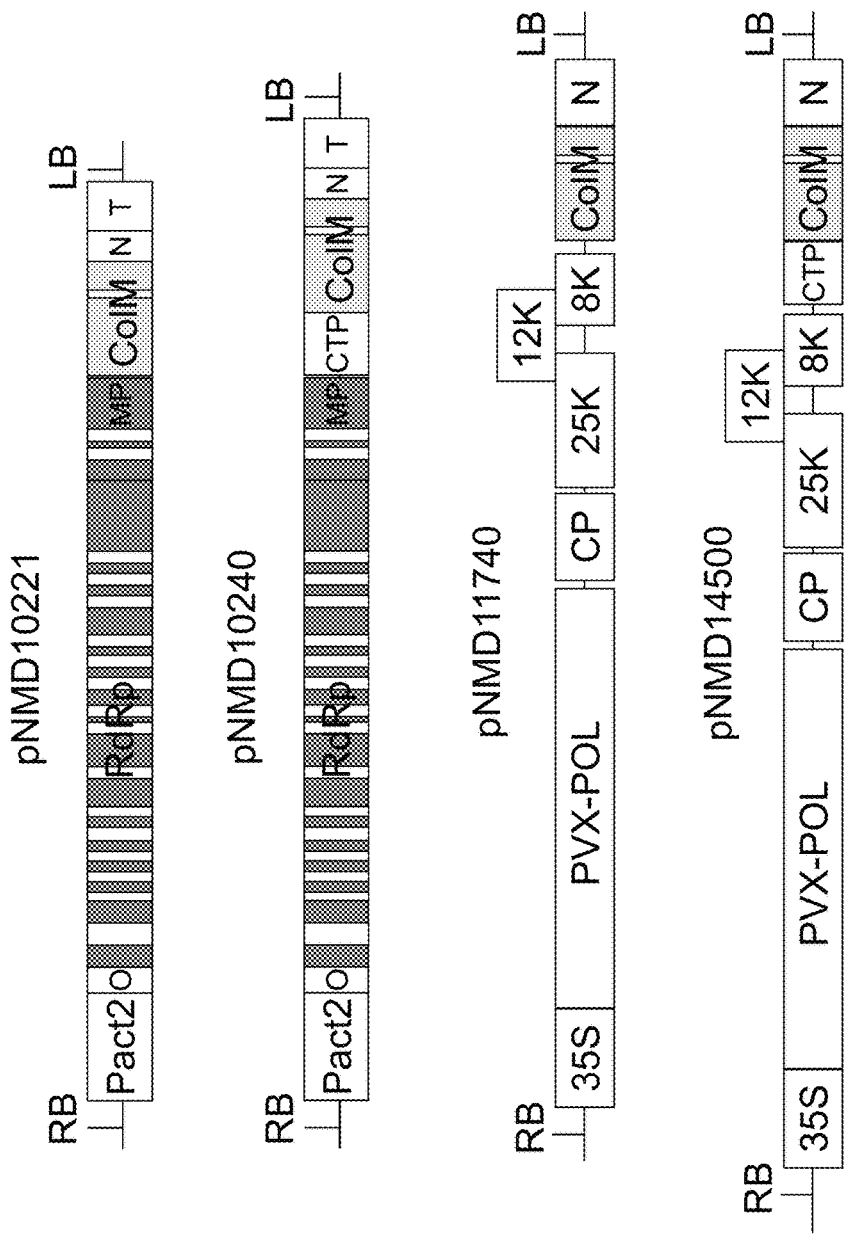

FIG. 2 shows schematically viral vectors for Colicin M expression used in the Examples. pNMD10221 and pNMD10240 constructs are based on Tobacco mosaic virus (TMV); pNMD11740 and pNMD14500 vectors are Potato virus X (PVX)-based. ColM: Colicin M coding sequence with codon usage optimized for *Nicotiana benthamiana*; CTP: chloroplast targeting peptide.

Figure 3:
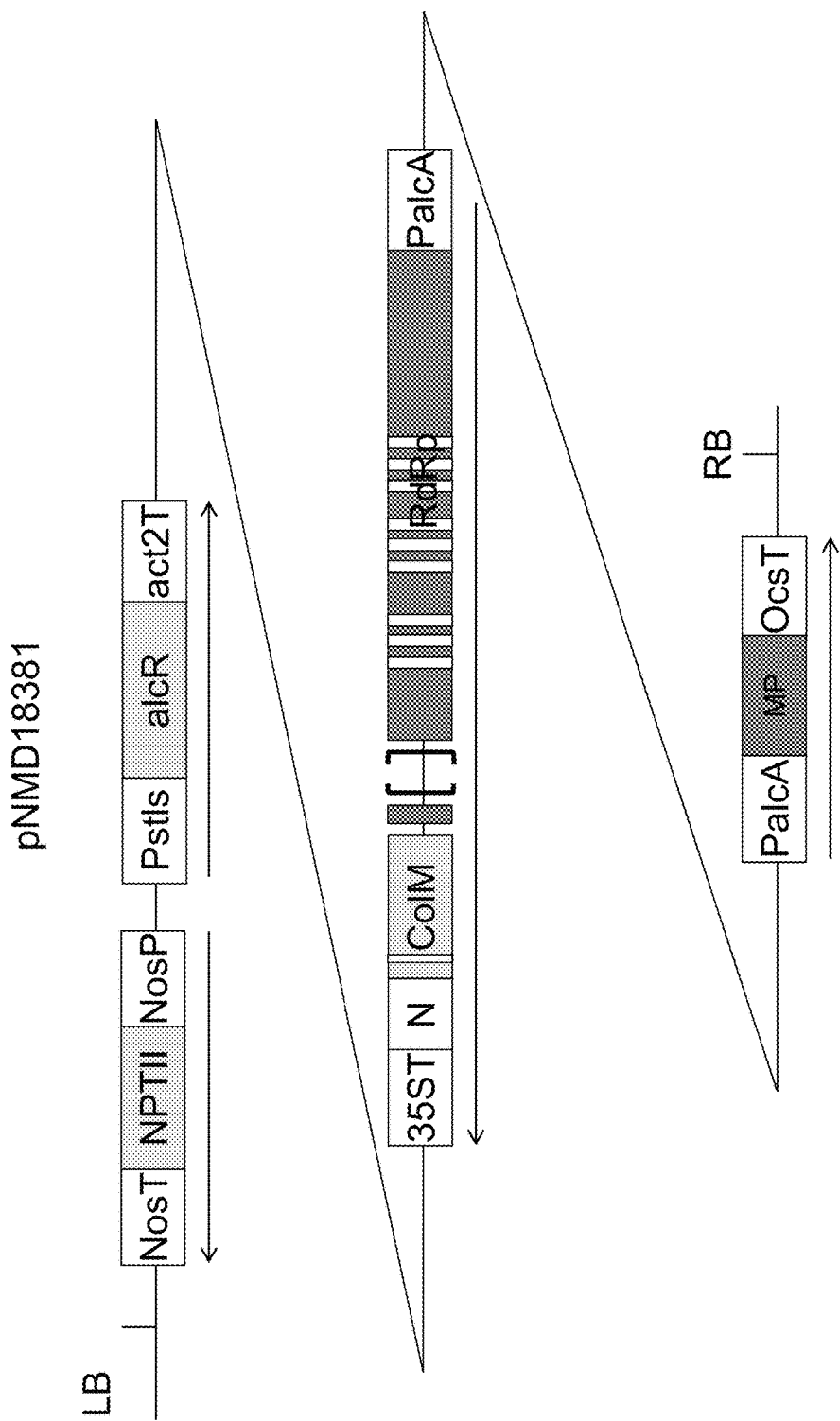

FIG. 3 depicts the double-inducible viral vector pNMD18381 for ethanol-induced Colicin M expression used for stable transformation of *Nicotiana benthamiana* plants. The T-DNA region of the plasmid contains four expression cassettes: 1) neomycin phosphotransferase II coding sequence cloned under the control of nopalin synthase promoter from *Agrobacterium;* 2) coding sequence of the ethanol-sensing transcriptional activator AlcR from *Aspergillus nidulans* (GeneBank: XM_677155.1) cloned under the control of potato ST-LS1 gene promoter (GenBank: X04753.1); 3) cr-TMV replicon (with deletion, indicated by the bracket, of a movement protein coding sequence fragment and insertion of colicin M ORF) cloned under the control of the ethanol-inducible alcohol dehydrogenase (a/cA) promoter from *Aspergillus nidulans* fused with minimal 35S promoter sequence (Werner at al. 2011); and 4) cr-TMV movement protein coding sequence cloned under the control of a/cA promoter.

NosT stands for nopaline synthase terminator; NPTII: neomycin phosphotransferase II for selection of transgenic plants; NosP: nopaline synthase promoter; Pstls: potato ST-LS1 gene promoter; alcR: AlcR coding sequence from *Aspergillus nidulans*; act2T: terminator of *Arabidopsis* actin2 gene; PalcA: ethanol-inducible a/cA promoter from *Aspergillus nidulans* fused with minimal 35S promoter sequence; 35ST: cauliflower mosaic virus 35S terminator; N: 3'-non-translated region from cr-TMV; A: the lambda insulator (999 bp long fragment between nucleotide position 31748 to 32746 of *Enterobacteria* phage lambda genome (GenBank: J02459.1); MP: movement protein ORF from cr-TMV; OcsT: terminator of octopine synthase gene from *Agrobacterium*. The position of MP deletion in TMV viral replicon is shown with brackets. Arrows indicate the direction of transcription.

FIGS. 4A-4B show comparative SDS-PAGE analysis of expression for colicins after the infiltration of *Nicotiana benthamiana* plants with *agrobacteria* carrying viral vectors. Plant leaf material was extracted with 5 volumes of the buffer containing 50 mM HEPES (pH7.0), 10 mM potassium acetate, 5 mM magnesium acetate, 10% (v/v) glycerol, 0.05% (v/v) Tween-20 and 300 mM NaCl. Protein extracts were resolved in 12% polyacrylamide gels. Before loading on the gel, aliquots of protein extracts were mixed with Laemmli buffer in the proportion 1:1 and incubated at 95° C. for 5 min. Numerals above gel lanes stand for protein extracts from plant tissues expressing the following recombinant proteins: 1—colicin E2; 2—colicin E3; 3—colicin E6; 4—colicin E7; 5—colicin D; 6—colicin N; 7—colicin K; 8—colicin 5; 9—colicin U; 10—colicin B; 11—colicin Ia; 12—colicin M. Numeral 13 corresponds to the extract from uninfected leaf tissue used as a negative control. L—PageRuler™ Prestained Protein Ladder (Fermentas, #SM0671). Arrows indicate specific protein bands corresponding to expressed recombinant colicins.

FIG. 4A. For gel loading, aliquots containing either 8 μg of total soluble protein (TSP).

FIG. 4B. For gel loading, the extract volumes corresponding to 1.5 mg fresh weight of plant tissue were used.

Figure 5:
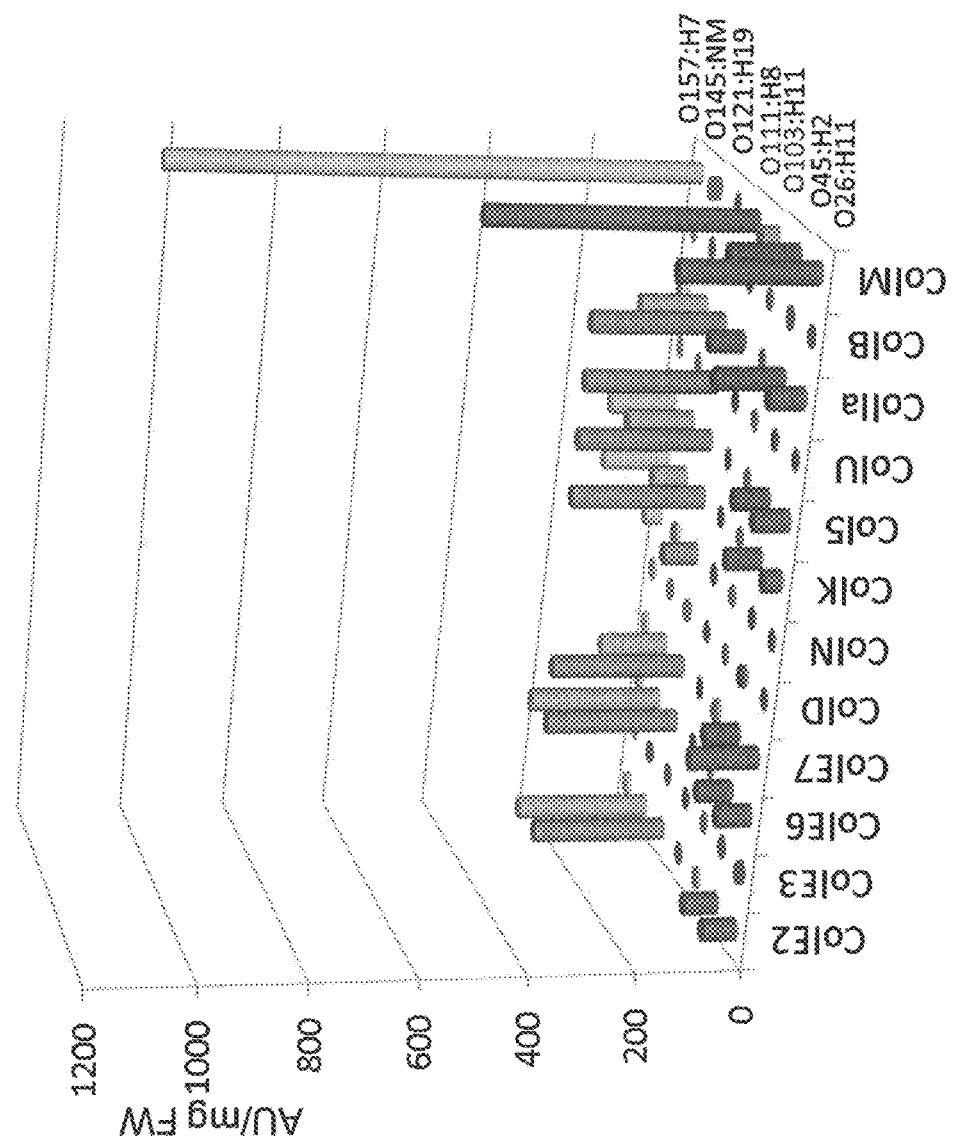

FIG. 5 shows the semi-quantitative evaluation of specific antimicrobial activity of colicin-containing plant extracts against Big 7 EHEC strains. The antimicrobial activity was tested using radial diffusion assay via a spot-on-lawn method and calculated in arbitrary units (AU) per mg fresh weight of plant biomass expressing recombinant colicins. Thereby, it reflects the yield of specific active agent per unit of biomass; i. e. the specific production capacity of the host is being evaluated. Arbitrary units are calculated as a dilution factor for the highest dilution of protein extract causing the detectable clearing effect in the radial diffusion assay. Tested recombinant colicins and EHEC strains are indicated.

Figure 6:
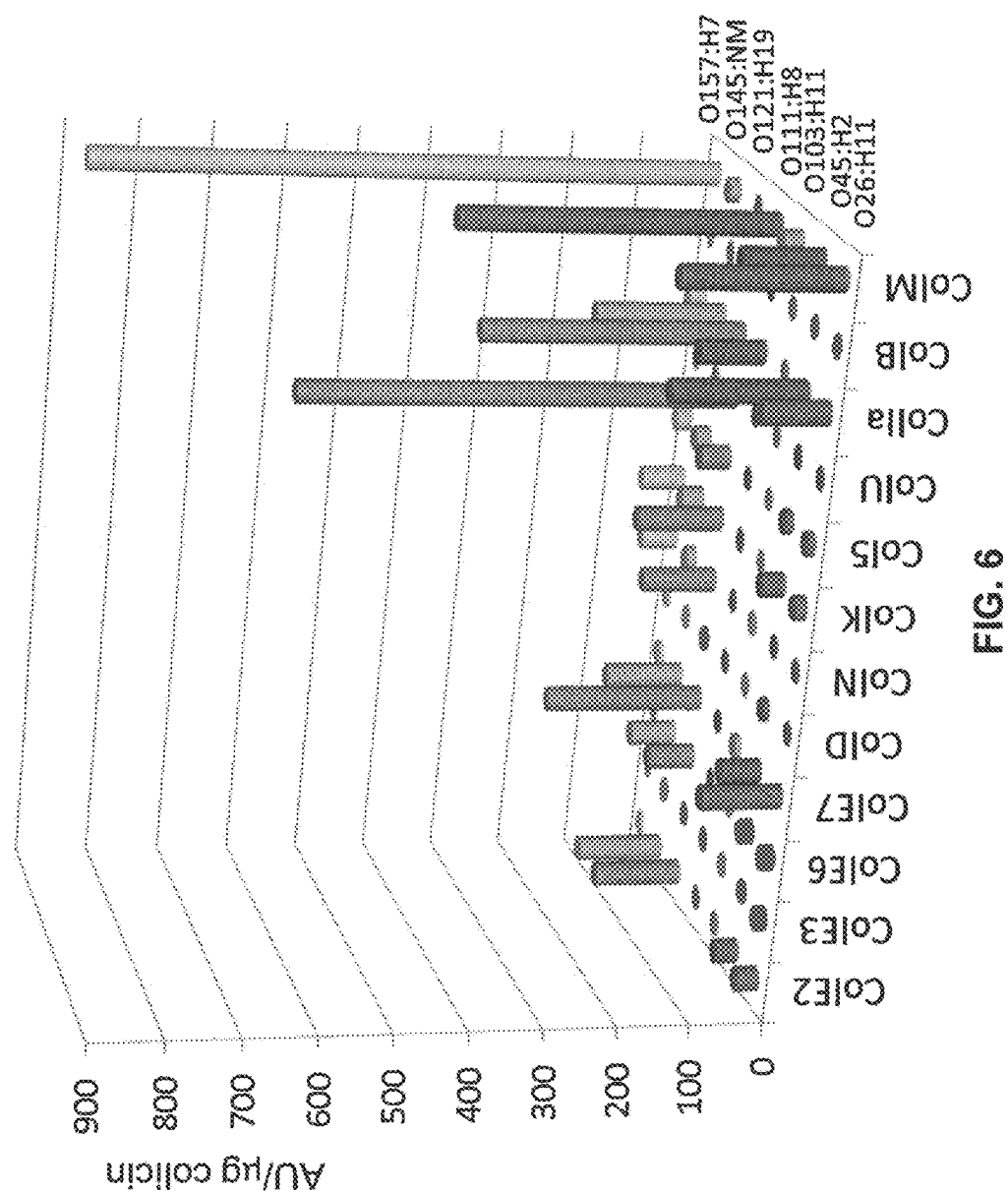

FIG. 6 shows the semi-quantitative evaluation of specific antimicrobial activity of colicin-containing plant extracts against Big 7 EHEC strains. The antimicrobial activity was tested using radial diffusion assay via spot-on-lawn-method and calculated in arbitrary units (AU) per μg of recombinant colicin, which reflects the specific activity of colicins against particular strains; i. e. the specific antimicrobial potency of colicins is being evaluated. Tested colicins and EHEC strains are indicated.

FIGS. 7A-7B shows the semi-quantitative evaluation of specific antimicrobial activity of plant extracts containing recombinant colicins against O104:H4 strain of EHEC.

FIG. 7A. The antimicrobial activity is expressed in arbitrary units (AU) per mg fresh weight of plant biomass.

FIG. 7B. The antimicrobial activity is expressed in arbitrary units (AU) per μg of colicin.

Figure 8:
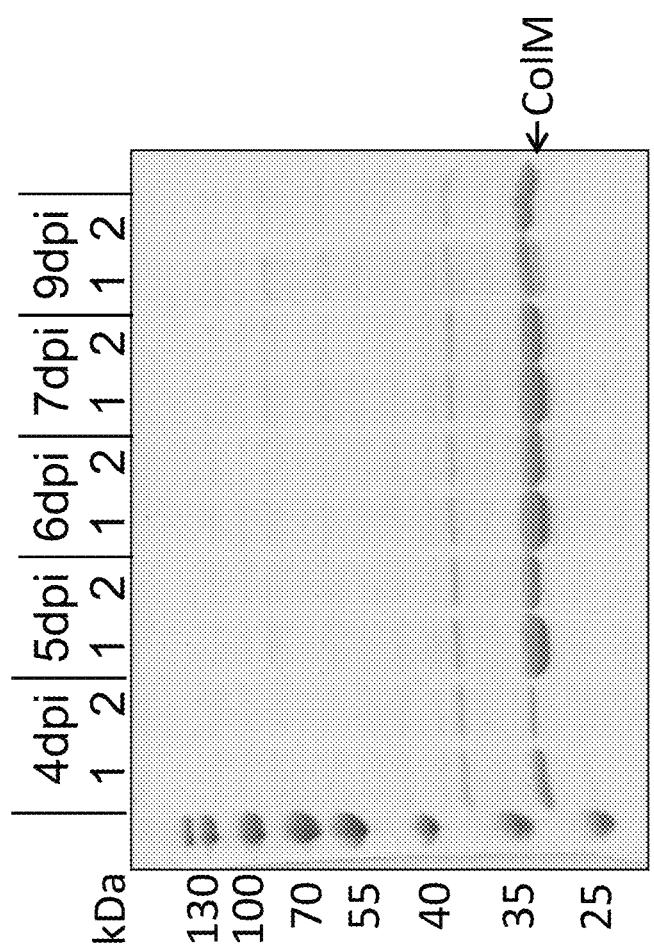

FIG. 8 shows SDS-PAGE analysis of Colicin M expression after the infiltration of *N. benthamiana* plants with *agrobacteria* carrying TMV and PVX viral vectors. 15 μl aliquots of total soluble extracts at different harvesting time points were resolved in 12% polyacrylamide gels. *Nicotiana benthamiana* plants were inoculated with GV3101 strain of *Agrobacterium tumefaciens* carrying either TMV-based vector pNMD10220 (lane 1) or PVX-based vector pNMD11740 (lane 2).

Figures 9A, 9B:
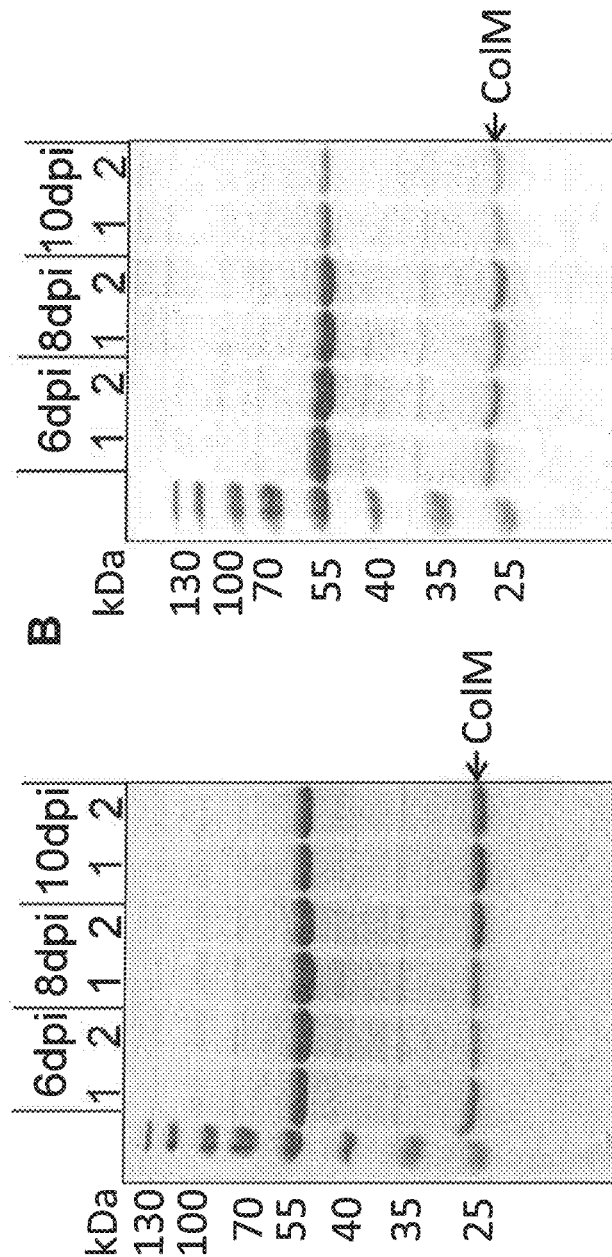

FIGS. 9A-9B show SDS-PAGE analysis of Colicin M expression in edible plants infiltrated with suspension of *Agrobacteria* carrying TMV-based viral vector pNMD10220. 15 μl aliquots of total soluble extracts at different harvesting time points were resolved in 12% polyacrylamide gels. Gels were stained with Coomassie blue. Plants were inoculated with either ICF320 (lane 1) or GV3101 (lane 2) strains of *Agrobacterium tumefaciens*.

FIG. 9A shows SDS-PAGE analysis of Colicin M expression in spinach *Spinacea oleracea*.

FIG. 9B shows SDS-PAGE analysis of Colicin M expression in sea beets *Beta vulgaris* ssp maritima.

FIG. 10 shows the analysis of stable transgenic *Nicotiana benthamiana* plants for ethanol-inducible Colicin M expression. 7.5 μl aliquots of Laemmli buffer extracts of non-induced and induced (4 days post induction) plant material were analyzed by SDS-PAGE (12% gel) with Coomassie staining. NbWT: non-transgenic wild type *Nicotiana benthamiana* plants; Nb18381T0#41, Nb18381T0#42, Nb18381T0#43, Nb18381T0#44 and Nb18381T0#45: independent lines of primary transformants (T0 generation) obtained using pNMD18381 construct; pNMD18381 transient: transient delivery of pNMD18381 construct using agroinfiltration; "−": no induction; "+": with ethanol induction.

Figure 11:
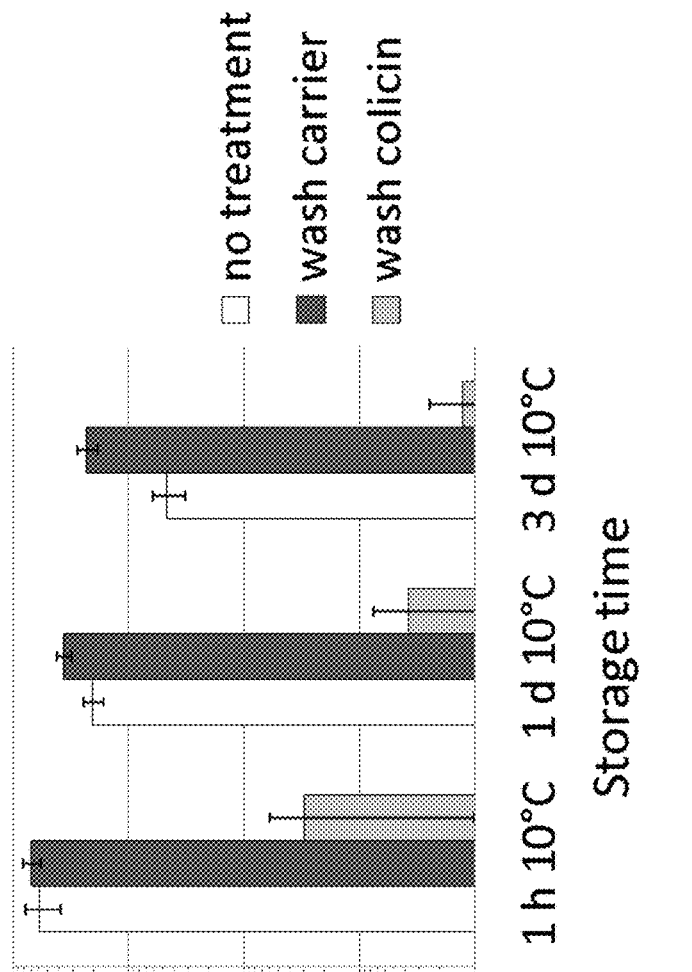

FIG. 11 shows the reduction of *E. coli* O157:H7 (DSM19206) cell population in contaminated steak meat pieces by treatment with two-component colicin mixture comprising colicin M and colicin E7.

FIG. 12 shows the reduction of *E. coli* 157:H7 (DSM19206) cell population in contaminated fresh-cut RTE cantaloupe melon pieces by treatment with two-component colicin mixture comprising colicin M and colicin E7.

FIG. 13 shows the reduction of *E. coli* O157:H7 (DSM19206) cell population on contaminated fresh-cut RTE apple pieces by treatment with a two-component colicin mixture containing colicin M and colicin E7 and with a five-component colicin mixture comprising colicins M, E7, K, B and 5.

Figure 14:
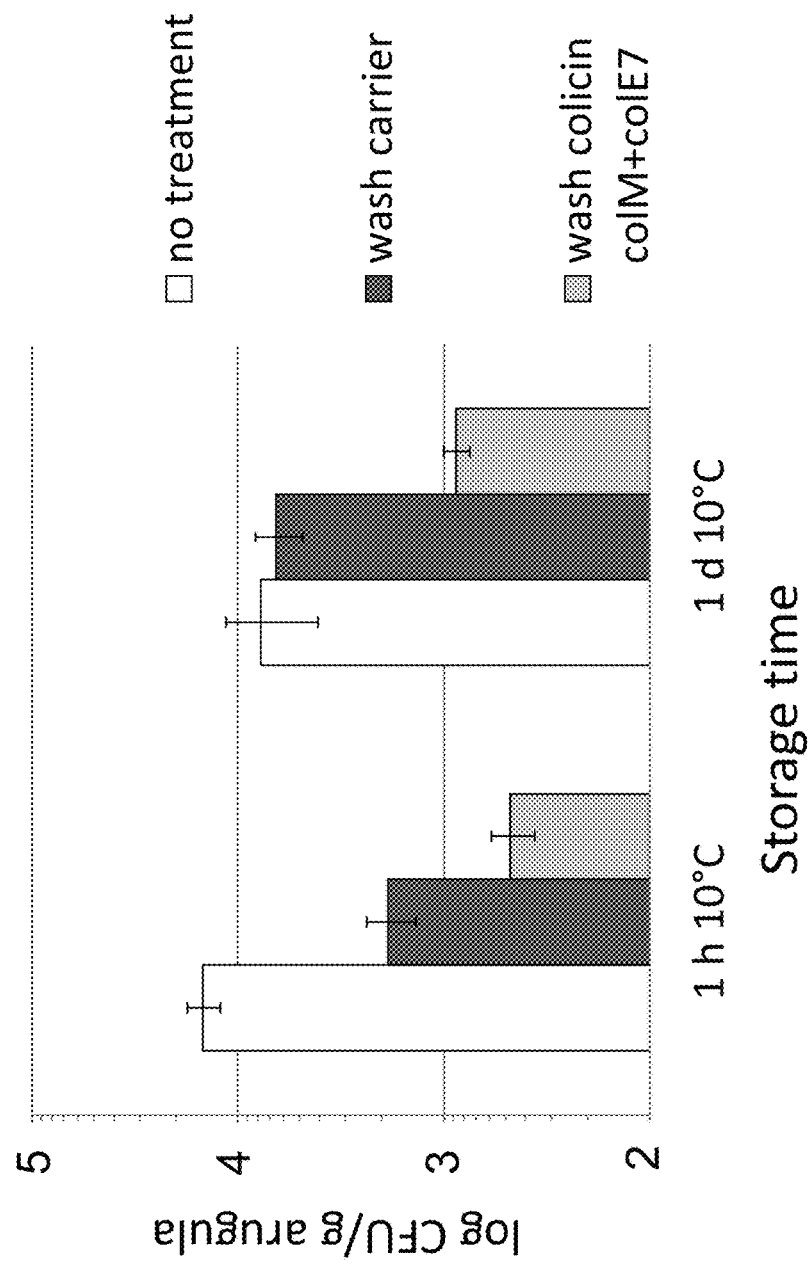

FIG. 14 shows the reduction of *E. coli* O157:H7 (DSM19206) cell population on contaminated fresh arugula leaves by treatment with a two-component colicin mixture containing colicin M and colicin E7.

Figure 15:
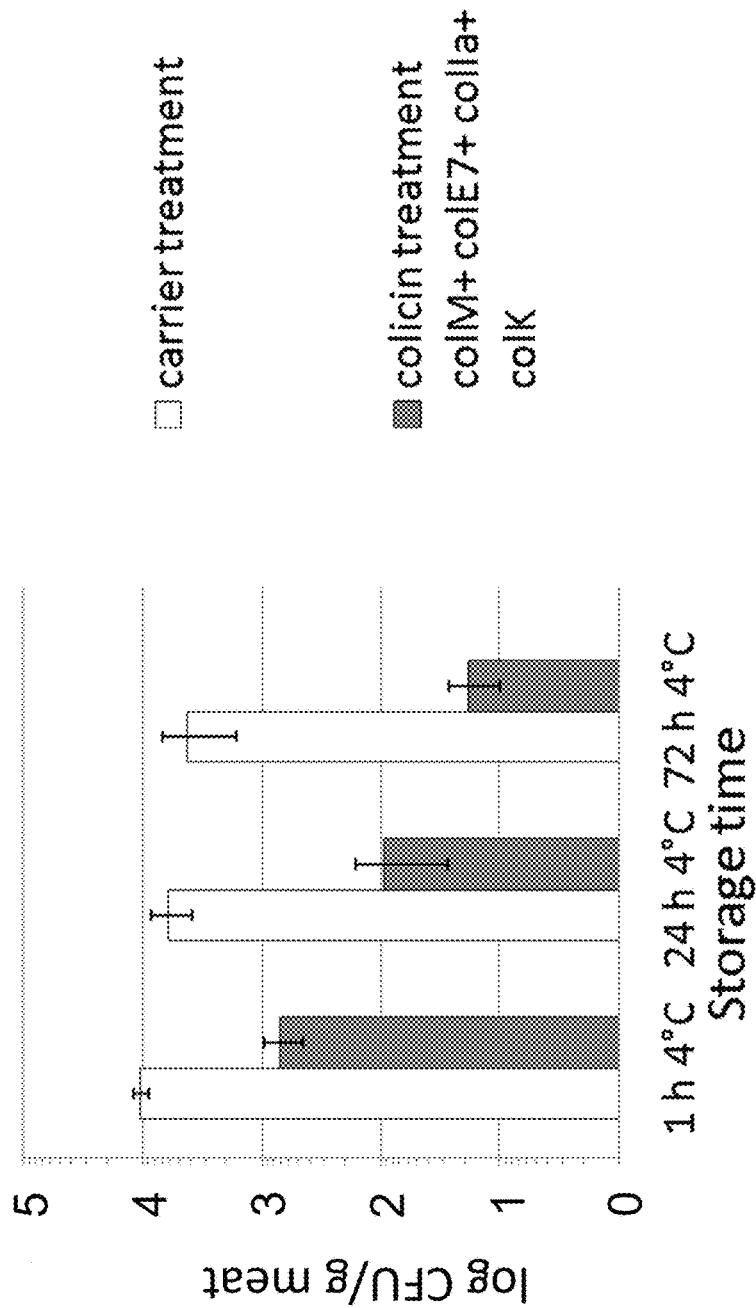

FIG. 15 shows the reduction of *E. coli* O157:H7 (DSM19206) cell population on contaminated beef steak meat by treatment with a four-component colicin mixture containing colicin M, E7, Ia and K.

Figure 16:
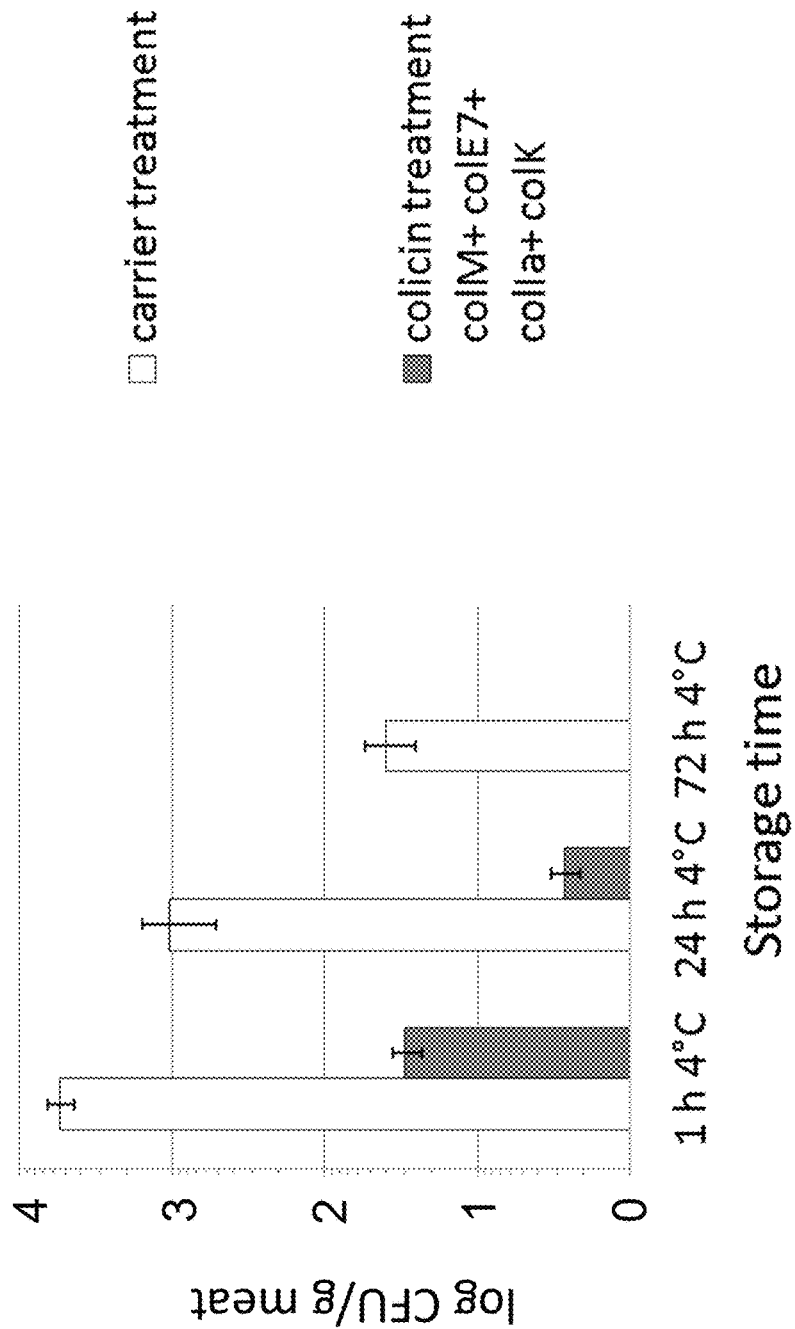

FIG. 16 shows the reduction of *E. coli* O157:H7 (DSM19206) cell population in ground beef meat by treatment with a four-component colicin mixture containing colicin M, E7, Ia and K.

FIG. 17 Summarized process (flow) diagram for colicin M production in plants.

Figure 18:
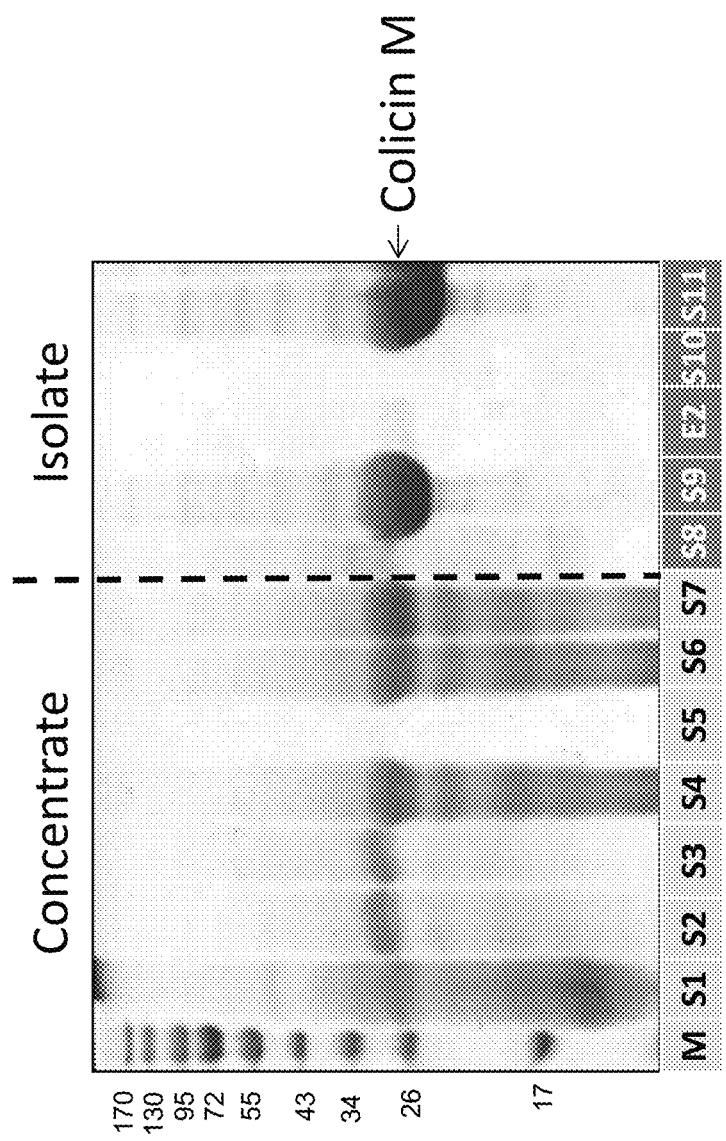

FIG. 18 Summary of purification of colicin M from *N. benthamiana* plants. The SDS-PAGE gel shows molecular weight marker in lane M. The initial green homogenate is shown in lane S1; the clarified acidic extract is shown in lane S2 and the neutralized, filtered extract in lane S3; lane S4 shows the UF concentrate; lane S5 and S6 show the retentate and permeate of diafiltration. S7 is the clarified Fractogel SO3-load, S8 corresponds to column flow through, S9 is the column eluate and E2 corresponds to the tailing part of elution peak. Lane S10 and S11 are permeate and retentate of the final formulation in 10 mM Citrate, 137 mM NaCl pH 7.3. The final retentate final retentate (S11) corresponds to colicin isolate.

Figure 19A:
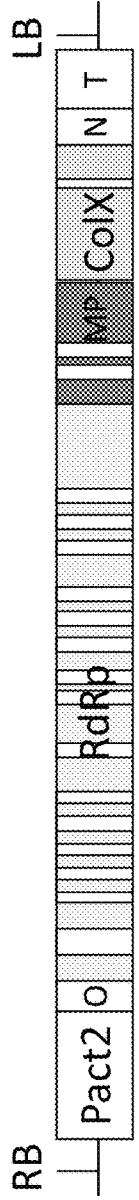
Figure 19B:
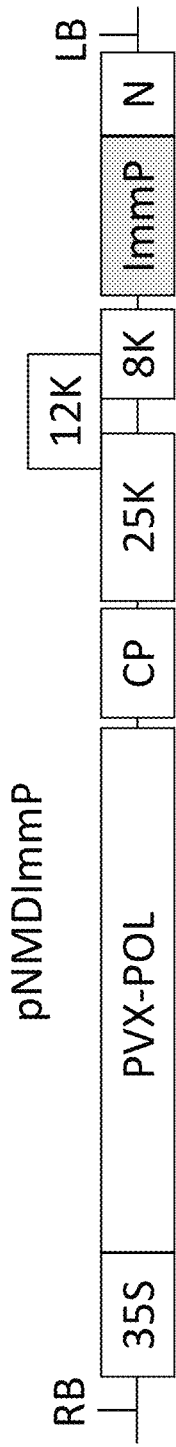

FIGS. 19A-19B show schematically viral vectors for the expression of colicins E5, E8, E9, A, S4, 10, R, 28b, Y, Ib, and cloacin DF13, and immunity proteins for colicins E5, E8, E9, and cloacin DF13 used in the examples. Constructs for the expression of colicins are based on Tobacco mosaic virus (TMV), whereas constructs for the expression of immunity proteins are based on Potato virus X (PVX).

FIG. 19A shows constructs for the expression of colicins. ColX stands for colicin coding sequence. All other designations as described in the legend to FIGS. 1A-1C. Coding sequences of colicins E5, E8, E9, Y, and cloacin DF13 contain the intron, which was inserted to prevent the cytotoxic effect of these proteins on *E. coli* cells used for plasmid cloning. The positions of intron insertion are represented in the table.

FIG. 19B shows constructs for the expression of colicin immunity proteins. ImmP stands for the coding sequence of colicin immunity protein. All other designations as described in the legend to FIGS. 1A-1C.

FIGS. 20A-20B show comparative SDS-PAGE analysis of expression for colicins E5, E8, E9, A, S4, 10, R, 28b, Y, Ib, and cloacin DF13 after the infiltration of *N. benthamiana* plants with *agrobacteria* carrying viral vectors. Protein extracts were resolved in 12% polyacrylamide gels. For gel loading, aliquots containing extract volumes corresponding to 1.5 mg fresh weight of plant tissue were used. Plant extracts were loaded in the next order: 1—colicin E8; 2—colicin E8+Immunity Protein E8; 3—colicin E9; 4—colicin E9+Immunity Protein E9; 5—colicin A; 6—colicin S4; 7—colicin 10; 8—colicin R; 9—colicin 28b; 10—colicin Y; 11—colicin Ib; and 12—uninfected leaf tissue used as a negative control. L—Protein Mass Ladder. Arrows show specific protein bands corresponding to expressed recombinant colicins. Expected protein molecular masses are: colicin E8—61 kDa, colicin E9—62 kDa, colicin A—63 kDa; colicin S4—54 kDa; colicin 10—53 kDa; colicin R—68 kDa; colicin 28b—48 kDa; colicin Y—67 kDa; colicin Ib—70 kDa.

FIG. 20A. Plant leaf material was extracted with 5 volumes of 2×Laemmli buffer containing 125 mM Tris-HCl (pH6.8), 4% SDS, 20% (v/v) glycerol, 10% 2-mercaptoethanol, and 0.002% bromophenol blue.

FIG. 20B. Plant leaf material was extracted with 5 volumes of the buffer containing 50 mM HEPES (pH7.0), 10 mM potassium acetate, 5 mM magnesium acetate, 10% (v/v) glycerol, 0.05% (v/v) Tween-20 and 300 mM NaCl.

FIG. 21 shows the semi-quantitative evaluation of specific antimicrobial activity of colicin-containing plant extracts against Big 7 EHEC strains. The antimicrobial activity for colicins E5, E8, E9, A, S4, 10, R, 28b, Y, Ib, and cloacin DF13 was tested using radial diffusion assay via spot-on-lawn-method and calculated in arbitrary units (AU) per mg fresh weight of plant biomass expressing recombinant colicins. Arbitrary units are calculated as a dilution factor for the highest dilution of protein extract causing the detectable clearing effect in the radial diffusion assay. Tested recombinant colicins and EHEC strains are indicated.

Figure 22:
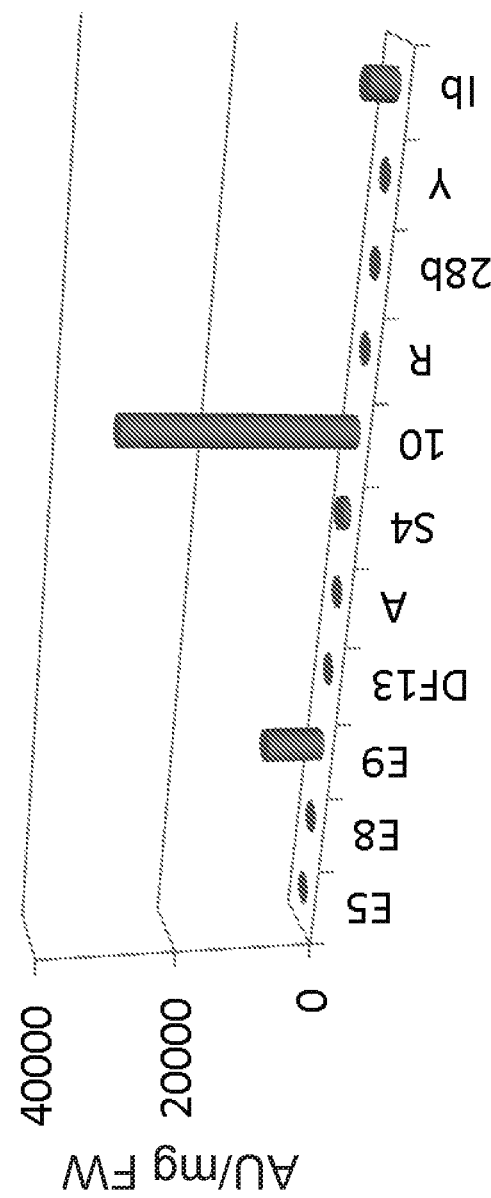

FIG. 22 shows the semi-quantitative evaluation of specific antimicrobial activity of plant extracts containing recombinant colicins E5, E8, E9, A, S4, 10, R, 28b, Y, Ib, and cloacin DF13 against O104:H4 strain of EHEC. The antimicrobial activity is expressed in arbitrary units (AU) per mg fresh weight of plant biomass.

DETAILED DESCRIPTION OF THE INVENTION

Colicins are plasmid-encoded cytotoxins synthesized by *Escherichia coli*, which are secreted into the medium and kill sensitive strains of *E. coli*. A colicin is sometimes abbreviated "Col" herein. Four cytotoxic classes of colicin have thus far been identified according to the mechanism by which they kill sensitive strains of *E. coli:*

- pore-forming colicins such as ColA, ColE1, ColN, ColK, ColIa, ColIb, and ColD, which kill cells by causing membrane depolarization
- RNase colicins, such as ColE3, ColE4, ColE6, and cloacin DF13, which specifically cleave 16S ribosomal, or ColD and ColE5, which cleave the anticodon loops of distinct tRNA
- DNase colicins such as ColE2, ColE7, ColE8, and ColE9, which are nonspecific endonucleases
- inhibitors of cell wall synthesis such as ColM.

Colicins from the above-mentioned groups have been characterized to some extent, and suggestions for practical applications of some colicins have been made. However, colicins are generally highly specific for their target *E. coli* strain or serotype, which is presumably due to the fact that colicins need specific receptor binding for entering the compartment of the target cells where they can exert their function. Thus, even where their mode of action would, in principle, allow broad antibacterial activity, the mechanism of internalization into target cells or compartments thereof generally prevents activity against diverse strains or serotypes of potential target *E. coli* cells. Thus, for practical application in antibacterial measures, prior knowledge of the target EHEC serotype would be necessary for selecting an appropriate colicin, which is time-consuming, laborious and requires specially trained personnel. This is probably a reason as to why colicins have, apparently, not been used in practice for antibacterial treatment so far.

The inventors have found that, among many colicins, colicin M has a surprisingly broad (or low) target cell specificity. Consequently, colicin M and derivatives thereof can be used, even without prior determination of an EHEC serotype to be attacked, for reducing the contamination with EHEC or for reducing viable EHEC cell density on objects such as food. For analogous reasons, colicin M can be used for preventing EHEC infection in patients. Moreover, colicin M may be used for reducing the load of EHEC in the digestive tract of farm animals such as cattle, sheep, and goats.

Colicin M is a naturally occurring *E. coli*-produced protein (CAS 39386-24-8; Swiss-Prot Entry PO5820; SID 135305941, deposit date 2012-03-21). Colicin M has a molecular weight of about 29.45 kDa and consists of a single polypeptide chain of 271 amino acid residues. The amino acid sequence was filed with the GenBank database (AAA23589.1; Köck 1987) and is also shown in SEQ ID N0:1.

Colicin M is a peptidoglycanase that specifically cleaves the bond between the lipid moiety and the pyrophosphoryl group of the peptidoglycan lipid I and lipid II intermediates, located at the periplasmic side of the inner membrane (Gross and Braun, Mol. Gen. Genet. 251 (1996) 388-396; Barreteau et al., Microbial Drug Resistance 18 (2012), 222-229). The released C55-polyisoprenol no longer translocates MurNAc-pentapeptide-GlcNAc across the cytoplasmic membrane. Although the major part of colicin M produced remains inside cells and is not released into the culture medium, it does not kill the producer cells. Instead, it kills sensitive strains after it has been taken up across the outer membrane into the periplasm. Colicinogenic strains are protected against the toxin they produce by co-expression of a specific immunity protein.

The mode of action of colicin M involves the steps of adsorption to the FhuA outer membrane receptor, energy-dependent translocation through the outer cell membrane into the periplasm by the TonB import machinery (TonB, ExbB and ExbD), and catalytic action of its substrate. Each of these steps is performed by a specific protein domain. Accordingly, colicins share a three-domain structural organization and a narrow antibacterial spectrum. Barreteau et al., Microbial Drug Resistance 18 (2012) 222-229 reviews recent knowledge on the biology of colicin M. The three domains of colicin M are referred to as translocation domain, receptor-binding domain, and activity domain from the N- to the C-terminus. The amino acid sequence stretch of the N-terminal translocation domain is usually defined as ranging from amino acid position 1 to (and including) position 35 in SEQ ID NO: 1. The amino acid sequence stretch of the central receptor-binding domain is usually defined as ranging from amino acid position 36 to (and including) position 140 in SEQ ID NO: 1. The amino acid sequence stretch of the C-terminal activity domain is generally defined as ranging from position 141 to 271 in SEQ ID NO: 1.

In the methods of the invention, colicin M of SEQ ID NO:1 may be used or a derivative thereof. Colicin M and its derivative as defined in the following are also referred to herein collectively as "protein of interest". The derivative preferably has a peptidoglycanase activity of at least 20% of the peptidoglycanase activity of colicin M of SEQ ID NO:1 in the standard assay with lipid I as substrate for colicin M activity described by El Ghachi cited below.

With regard to the activity domain, the amino acid sequence is not particularly limited provided the derivative has at least 20% of the peptidoglycanase activity of colicin M of SEQ ID NO:1. In preferred embodiments, the peptidoglycanase activity is at least 40%, more preferably at least 60%, and most preferably at least 80%, of the peptidoglycanase activity of colicin M of SEQ ID NO:1. The activity is determined according to the standard assay for colicin M activity described by El Ghachi et al., J. Biol. Chem. 281 (2006) 22761-22772 using lipid I as the substrate.

The activity domain may, alternatively or additionally, have from 1 to 30, preferably from 1 to 20, more preferably from 1 to 15, even more preferably from 1 to 10, and most preferably from 1 to 5, amino acid residue substitutions, insertions, additions and/or deletions compared to amino acid residues 141 to 271 of SEQ ID NO: 1. The activity domain may preferably have from 1 to 30, preferably from 1 to 20, more preferably from 1 to 15, even more preferably from 1 to 10, and most preferably from 1 to 5, amino acid residue substitutions and/or terminal deletions compared to amino acid residues 141 to 271 of SEQ ID NO: 1. Herein, substitutions, insertions, additions and deletions may be combined; the number of substitutions, insertions, additions and/or (terminal) deletions given herein refers to the sum of substitutions, insertions, additions and deletions made compared to the applicable sequence stretch of SEQ ID NO: 1.

In another embodiment, the activity domain has an amino acid sequence identity of at least 80%, preferably of at least 85%, more preferably of at least 90%, even more preferably at least 95%, and most preferably of at most 97%, to the activity domain of SEQ ID NO: 1. Alternatively, the activity domain of the derivative has an amino acid sequence similarity of at least 90%, preferably at least 95%, to the activity domain SEQ ID NO: 1. The conditions above based on peptidoglycanase activity and structural similarity to the activity domain of SEQ ID NO: 1 may be combined. Thus, the derivative of colicin M may have a peptidoglycanase activity as listed above and may have from 1 to 30, preferably from 1 to 20, more preferably from 1 to 15, more preferably from 1 to 10, and most preferably from 1 to 5 insertions and/or additions and/or deletions and/or substitutions compared to residues 141 to 271 of SEQ ID NO: 1. In another embodiment, the derivative of colicin M may have a peptidoglycanase activity as listed above and may have an amino acid sequence identity of at least 80%, preferably of at least 85%, more preferably of at least 90%, more preferably at least 95% and most preferably of at most 97%, to the activity domain of SEQ ID NO: 1.

In the derivatives of the activity domain, one or more of the following amino acid residues influence the catalytic activity and are therefore preferably those of SEQ ID NO: 1, i.e. are not altered in the derivative: P176, D226, Y228, D229, H235 and R236, preferably all of these amino acid residues are those of SEQ ID NO: 1. More preferably, any one or all of the following amino acid residues are those of SEQ ID NO: 1: P176, D226, Y228, D229, H235, R236, R222, N231, E241 and T244.

In a preferred embodiment, the activity domain of the derivative has from 1 to 20, more preferably from 1 to 15, more preferably from 1 to 10, and most preferably from 1 to 5 insertions and/or additions and/or deletions and/or substitutions (preferably substitutions and/or terminal deletions) compared to residues 141 to 271 of SEQ ID NO: 1 and all of the following amino acid residues are those of SEQ ID NO: 1: P176, D226, Y228, D229, H235, R236, R222, N231, E241 and T244.

The protein of interest has a central receptor-binding domain of residues 36 to 140 of colicin M or a receptor-binding domain having from 1 to 15, preferably from 1 to 10, more preferably from 1 to 6, and most preferably from 1 to 3 amino acid substitutions, insertions, additions, and/or deletions compared to amino acid residues 36 to 140 of SEQ ID NO: 1. The protein of interest may have a central receptor-binding domain of residues 36 to 140 of colicin M or a receptor-binding domain having from 1 to 15, preferably from 1 to 10, more preferably from 1 to 6, and most preferably from 1 to 3 amino acid substitutions and/or terminal deletions compared to amino acid residues 36 to 140 of SEQ ID NO: 1. In another embodiment, the receptor-binding domain has an amino acid sequence identity of at least 90%, preferably of at least 95%, and most preferably of at most 97%, to the receptor-binding domain of SEQ ID NO: 1. Alternatively, the receptor-binding domain of the derivative has an amino acid sequence similarity of at least 95%, preferably at least 97%, to the receptor-binding domain SEQ ID NO: 1. In addition to the amino acid residues given above from the activity domain that are preferably not changed compared to SEQ ID NO: 1, P107 and P129 from the central domain are, in one embodiment, present in the colicin M derivative.

The protein of interest has an N-terminal translocation domain of amino acid residues 1 to 35 of colicin M or an N-terminal translocation domain having from 1 to 8, preferably from 1 to 4, more preferably from 1 to 2, more preferably of one amino acid substitutions, insertions, additions, and/or deletions (preferably substitutions and/or terminal deletions) compared to residues 1 to 35 of SEQ ID NO: 1. The term "terminal deletions" refers to deletions at the termini of the sequence referred to, such as SEQ ID NO: 1. In another embodiment, the N-terminal translocation domain has an amino acid sequence identity of at least 90%, preferably of at least 95%, and most preferably of at most 97% to the N-terminal translocation domain of SEQ ID NO: 1. Alternatively, the N-terminal translocation domain of the derivative has an amino acid sequence similarity of at least 95%, preferably at least 97%, to the N-terminal translocation domain SEQ ID NO: 1. In one embodiment, the derivative as defined above comprises, in the N-terminal translocation domain, the TonB box of residues 2 to 7 of SEQ ID NO: 1. In the same or another embodiment, the derivative has no N-terminal amino acid residue addition compared to SEQ ID NO: 1.

A derivative of colicin M may comprise an additional C-terminal amino acid sequence stretch such as purification tags, e.g. as a His-tag of 6 or more contiguous histidine residues; the derivative has, preferably, no N-terminal amino acid residue addition.

For the purpose of determining similarity between amino acid sequences in the present invention, the amino acid residues belonging to each of the following groups are considered similar (in the standard one-letter code):

F, Y, W
V, I, L
R, K, H
D, E
N, Q
A, T, S

The derivative of colicin M has minimum toxicity against a colicin M-sensitive *E. coli* strain compared to colicin M of SEQ ID NO:1. The toxicity of the derivative of colicin M should be such that the derivative and the colicin M of SEQ ID NO: 1 produce spots free of viable bacteria of the sensitive *E. coli* strain of the same diameter 12 hours after spotting 5 microliters of a solution of said derivative of colicin M and the colicin M of SEQ ID NO: 1 onto a lawn of the sensitive *E. coli* strain on agar plates and subsequent incubation of the agar plates at 37° C., wherein the concentration of the derivative of colicin M is at most 5 times that of the comparative solution of the colicin M of SEQ ID NO: 1. Preferably, the concentration of the derivative of colicin M is at most 3 times, preferably at most twice that of the comparative solution of the colicin M of SEQ ID NO: 1. The colicin M-sensitive *E. coli* strain may be any sensitive *E. coli* strain. For convenience, *E. coli* strain DH10B may be used for testing the toxicity of colicin M or its derivative. Otherwise, the assay described in Example 3 may be employed. Thus, the radial diffusion assays via spot-on-lawn-method may be used.

The agar plates for the assay may be overlaid with soft agar containing cells of tested *E. coli* strain. 10×10 cm quadratic petri dishes may be poured with 15-20 ml LB agar medium (1.5% w/v agar). LB soft agar medium (0.8% (w/v) agar) is melted, 20 ml aliquots are transferred into 50 ml plastic tubes and their temperature is adapted to 50-55° C. *E. coli* overnight cultures of the test bacteria adjusted to OD600=1.0 with LB medium are added to the soft agar medium in a ratio of 200 µl bacterial culture per 20 ml medium resulting in the final OD600=0.01 or approximately 1×10$^7$ cells/ml. Raw colicin preparations such as plant leaf material containing expressed colicin M or its derivative may be extracted as described in Example 2. A 1:1 dilution series of plant extracts starting with undiluted samples by using extraction buffer may be prepared. 5 µl aliquots of total soluble protein (TSP) dilution series may be applied to the agar plates that are then incubated at 37° C. overnight. Antimicrobial activity (toxicity) of the colicin M or its derivative can be evaluated visually based on clearing zones and the diameter of spots may be measured.

The above definitions of the colicin M and its derivatives of the three domains of colicin M may be combined. An embodiment of the protein of interest is as follows:

a colicin M or a derivative of colicin M comprising:

an N-terminal translocation domain having up to 4 amino acid residue substitutions, insertions, additions, and/or deletions compared to residues 1 to 35 of SEQ ID NO: 1, comprises residues 2 to 7 of SEQ ID NO: 1 and has no N-terminal addition compared to SEQ ID NO: 1;

a central receptor-binding domain having up to 10, preferably up to 6, and most preferably up to 3 amino acid residue substitutions, insertions, additions, and/or deletions compared to the amino acid sequence segment of residues 36 to 140 of SEQ ID NO: 1 and comprises P107 and P129 of SEQ ID NO: 1; and an activity domain having up to 20, preferably up to 10 amino acid residue substitutions, insertions, additions and/or deletions compared to residues 141 to 271 of SEQ ID NO: 1 and having amino acid residues P176, D226, Y228, D229, H235 and R236 of SEQ ID NO: 1, preferably amino acid residues P176, D226, Y228, D229, H235, R236, R222, N231, E241 and T244 of SEQ ID NO: 1.

The colicin M or its derivatives to be used according to the invention may be produced by known methods of protein expression in a standard expression system. For producing the colicin M or its derivative, a nucleotide sequence encoding the colicin M or its derivative may be expressed in a suitable host organism. Methods for producing and purifying colicin M have been described in the prior art and any such methods may be used. An expression method employing an *E. coli* expression system was described by Zeth et al., J. Biol. Chem. 283 (2008) 25324-25331. If eukaryotic expression systems are used, one or more introns may be inserted in the coding sequence of the colicin for preventing toxic effects on bacteria used for cloning.

Particularly efficient expression methods are plant expression systems that are known in the prior art. Plant expression systems for expressing colicin M or a derivative thereof and for expressing other colicins or derivatives thereof are described in the Examples. A possible way of achieving expression of a nucleotide sequence of interest in plants is the use of self-replicating (viral) replicons containing the nucleotide sequence encoding the colicin M or its derivative, or encoding another colicin or its derivative. Plant viral expression systems have been described in many publications, such as in WO2008028661, WO2006003018, WO2005071090, WO2005049839, WO2006012906, WO02101006, WO2007137788 or WO02068664 and many more publications are cited in these documents. Various methods for introducing a nucleic acid molecule, such as a DNA molecule, into a plant or plant part for transient expression are known. *Agrobacteria* may be used for transfecting plants with the nucleic acid molecule (vector) or nucleic acid construct e.g. by agroinfiltration or spraying with agrobacterial suspensions. For references see WO 2012/019660, WO 2014/187571, or WO 2013/149726.

In embodiments wherein strong expression of the protein of interest (or other colicin) is desired, a nucleic acid construct containing the nucleotide sequence encoding the colicin M or its derivative (or encoding another colicin) may encode a viral vector that can replicate in plant cells to form replicons of the viral vector. In order to be replicating, the viral vector and the replicons contain an origin of replication that can be recognized by a nucleic acid polymerase present in plant cells, such as by the viral polymerase expressed from the replicon. In case of RNA viral vectors (referred to as "RNA replicons"), the replicons may be formed by transcription under the control of a promoter active in plant cells, from the DNA construct after the latter has been introduced into plant cell nuclei. In case of DNA replicons, the replicons may be formed by recombination between two recombination sites flanking the sequence encoding the viral replicon in the DNA construct, e.g. as described in WO00/17365 and WO 99/22003. If the replicon is encoded by the DNA construct, RNA replicons are preferred. Use of DNA and RNA viral vectors (DNA or RNA replicons) has been extensively described in the literature over the years. Some examples are the following patent publications: WO2008028661, WO2007137788, WO 2006003018, WO2005071090, WO2005049839, WO02097080, WO02088369, WO02068664. An example of DNA viral vectors are those based on geminiviruses. For the present invention, viral vectors or replicons based on plant RNA viruses, notably those based on plus-sense single-stranded RNA viruses may be used. Accordingly, the viral replicon may be a plus-sense single-stranded RNA replicon. Examples of such viral vectors are those based on tobacco mosaic virus (TMV) and potexvirus X (PVX). "Based on" means that the viral vector uses the replication system such as the replicase and/or other proteins involved in replication of these viruses. Potexvirus-based viral vectors and expression systems are described in EP2061890 or WO2008/028661.

The colicin such as colicin M or its derivative may be expressed in a multi-cellular plant or a part thereof, notably a higher plant or parts thereof. Both monocot and dicot (crop) plants can be used. Common plants usable for expressing the protein of interest include *Nicotiana benthamiana, Nicotiana tabacum*, spinach, *Brassica campestris, B. juncea*, beets (*Beta vulgaris*), cress, arugula, mustard, Strawberry, *Chenopodium capitatum*, lettuce, sunflower, cucumber, Chinese cabbage, cabbage, carrot, green onion, onion, radish, lettuce, field peas, cauliflower, broccoli, burdock, turnip, tomato, eggplant, squash, watermelon, prince melon, and melon. Expression in edible plants may be used for preventing contamination of the plants or food made therefrom with EHEC. Expression in edible plants may also be used for preparing a colicin-containing composition that may, in turn, be used for contacting an object such as food for preventing or reducing contamination of the object with EHEC. Any remaining components in the composition from the edible plant will not be harmful for consumers if the composition is used for treating food. Examples of edible plants are those listed above, except *Nicotiana benthamiana* and *Nicotiana tabacum*. In another embodiment, plants are used that do not normally enter the food chain such as *Nicotiana* species such as *N. tabacum* and *N. benthamiana* may be used.

Generally, the protein of interest (or other colicin) is expressed in the cytosol of cells of the plants or plant parts. In this case, no signal peptide directing the protein of interest into a particular compartment is added to the enzyme. Alternatively, the protein of interest can be expressed in or targeted into chloroplasts of the plants; in the latter case, an N-terminal pre-sequence, generally referred to as plastid transit peptide or chloroplast targeting peptide, is added to the N-terminal or C-terminal end, preferably the C-terminal end, of the protein of interest.

Expressed colicin such as colicin M or its derivative may be purified from the cells or plants having expressed it. The method of Zeth et al., J. Biol. Chem. 283 (2008) 25324-25331 employing affinity purification via a His-tag at the N-terminus of colicin M may be employed. If the colicin or its derivative such as colicin M or the derivative thereof is expressed in plants, the plants or tissue thereof having expressed protein may be harvested, the tissue may be homogenized, and insoluble material may be removed by centrifugation or filtration. If relatively pure colicin (such as colicin M or its derivative) is desired, the solution that may have been further purified by acid extraction and subsequent neutralization and removal of insoluble material, may be subjected to cation-exchange chromatography which can remove other host-cell proteins and plant metabolites such as polyphenols. Purified colicin solutions such as colicin M solutions may be concentrated and/or freeze-dried.

Accordingly, the invention provides processes of producing a colicin such as colicin M or a derivative thereof, or a colicin-containing preparation. In a first general process, the invention provides a process of producing a colicin such as colicin M or a derivative thereof, or a colicin-containing preparation, comprising:

(i) expressing said colicin in a plant from a nucleic acid construct encoding said colicin;
(ii) harvesting the plant and homogenizing the plant or material of the plant containing expressed colicin to produce a homogenate, optionally followed by removing solid or insoluble material;
(iii) acidifying the homogenate or a clarified fraction thereof to a pH of below pH5, followed by removal of insoluble material, to obtain a colicin-containing solution;
(iv) neutralizing the clarified colicin-containing solution, followed by removal of insoluble material;
(v) optionally concentrating the colicin-containing solution obtained in the previous step; and
(vi) optionally freeze-drying the solutions obtained in step (iv) or (v) to obtain a freeze-dried preparation of said colicin.

If the colicin is expressed in edible plants, crude protein extracts from the edible plants or semi-purified concentrates may be used for preventing or reducing contamination of an object such as food with EHEC. Therefore, in the first general process, the plant in which the colicin (or its derivative) is expressed is preferably an edible plant. It is understood that, in the context of the production processes, references to the colicins includes the derivatives of the colicins.

In a second general process, the invention provides a process of producing a colicin such as colicin M or a derivative thereof, or a colicin-containing preparation, comprising:

(i) expressing said colicin in a plant from a nucleic acid construct encoding said colicin;
(ii) harvesting the plant and homogenizing the plant or material of the plant containing expressed colicin to produce a homogenate, optionally followed by removing solid or insoluble material;
(iii) acidifying the homogenate or a clarified fraction thereof to a pH of below pH5, followed by removal of insoluble material, to obtain a colicin-containing solution;
(iv) neutralizing the clarified colicin-containing solution, followed by removal of insoluble material;
(v) optionally concentrating the colicin-containing solution obtained in the previous step;
(vi) purifying said colicin by column chromatography, preferably by cation exchange chromatography; and
(vii) optionally freeze-drying the solutions obtained in step (iv) or (v) to obtain a freeze-dried preparation of said colicin.

The second general process leads to high purity colicin. Preferably, the plant in the second general process is *N. tabacum* or *N. benthamiana.*

In the above production processes, the colicin may be colicin M, colicin E7, colicin B, colicin Ia, colicin U, colicin K, colicin 5, colicin E5, colicin E8, colicin E9, colicin A, colicin S4, colicin 10, colicin R, colicin 28b, colicin Y, colicin Ia, colicin Ib, or cloacin DF13, or a derivative of any of these colicins. A preferred colicin is colicin M or its derivative.

Colicin M or its derivative may be used in the invention for preventing or reducing contamination of an object such as food with EHEC. Contamination of an object with EHEC means adhesion of viable EHEC cells to the object. Reducing contamination with EHEC means reducing the number of viable EHEC cells adhering to the object. Determining contamination of objects with EHEC is part of the general knowledge. For example, dilution plating of solutions or dispersions of homogenized food as done in Examples 8 and 9 or dilution plating of rinsing solution of other objects may be used, followed by counting bacterial cells.

Colicins generally have a very narrow toxicity range against EHEC serotypes. The inventors have found that colicin M not only has toxicity against an exceptionally broad range of target EHEC, but also higher toxicity against several EHEC serotypes including *E. coli* O157:H7, O111:H8 and O26:H11 than many other colicins. Thus, the invention can be used for preventing or reducing contamination of an object such as food with any one or all of *E. coli* O157:H7, O111:H8 and O26:H11, preferably serotype O157:H7. The invention can further be used for preventing or reducing contamination of an object such as food with any one or all of the following *E. coli* serotypes: O26:H11, O45:H2, O103:H11, O111:H8, O157:H7, and O104:H4. The invention can further be used for preventing or reducing contamination of an object such as food with any one or all of the following *E. coli* serotypes: O26:H11, O45:H2, O103:H11, O111:H8, O145:NM, O157:H7, and O104:H4. Colicin M or a derivative thereof can further be used in a method of preventing infection of a mammal with enterohaemorrhagic *E. coli*.

For preventing or reducing contamination of an object with EPEC or EHEC, the surface of the object may be wetted with a composition such as a solution containing colicin M or its derivative. For example, the object such as food may be dipped into or sprayed with a solution of the colicin M or its derivative. The solution is preferably aqueous and may contain a buffer. The buffer may be an inorganic or organic acid or salts thereof. An example of an inorganic acid is phosphoric acid or salts thereof. Examples of the organic acid are HEPES, acetic acid, succinic acid, tartaric acid, malic acid, benzoic acid, cinnamic acid, glycolic acid, lactic acid, citric acid, and ascorbic acid. Preferred organic acids are malic acid, lactic acid, citric acid, and ascorbic acid. The pH of the solution may be from 4 to 8, preferably from 5 to 8, more preferably from 6 to 7.5. Further, the solution may contain isotonic agents such as glycerol or sodium chloride. The concentration of the colicin M or its derivative in the solution may be from 1 to 100 000 μg/l, preferably from 10 to 50 000 μg/l, more preferably from 100 to 10 000 μg/l, and even more preferably from 500 to 5 000 μg/l.

For broadening the range of target cells to be treated, colicin M or its derivative may be used in combination with any one or more other colicins such as with colE7, colB, colIa, colIb, colU, colK, col5, or derivatives thereof. A preferred colicin to be combined with colicin M or its derivative is colE7 or a derivative thereof. Other preferred colicins to be combined with colicin M or its derivative are colicin Ia (colIa) or colicin Ib (colIb) or a derivative thereof. Thus, the composition or solution containing colicin M or its derivative may contain any one or more of these further colicins or their derivatives. For each of the other colicin to be combined with colicin M or its derivative, the same concentrations as given above for colicin M or its derivative may be used. Alternatively, the total concentration of all colicins combined (including any colicin derivatives) may be as those given above for colicin M.

When colicin M or its derivative is used in combination with one or more other colicins, the spectrum of EHEC serotypes, contamination with which can be reduced or prevented, increases. In one embodiment, colicin M or its derivative is combined with any one or more or all of colE7, colB, colIa, colIb, colU, colK, col5 (or derivatives thereof), and contamination with any one or all of the following *E. coli* serotypes is prevented or reduced: serotypes O26:H11, O45:H2, O103:H11, O111:H8, O145:NM, O157:H7, O104:H4, and O121:H19. In a preferred embodiment, colicin M or its derivative is combined with colicin E7 or a derivative thereof for preventing or reducing contamination of an object such as food with any one or all O26:H11, O45:H2, O103:H11, O111:H8, O145:NM, O157:H7, O104:H4, and O121:H19.

After wetting, the wetted object may be further processed or may be left to dry. In the case of food, the wetted food may be further processed such as by slicing or grinding and/or may be packed for shipping to customers or prepared for consumption.

In other embodiments, colicin M or its derivative may be used in combination with any one or more other colicins selected from the group consisting of colicin E5, colicin E8, colicin E9, colicin A, colicin S4, colicin 10, colicin R, colicin 28b, colicin Y, colicin Ia, colicin Ib, and cloacin DF13 or a derivative of E5, colicin E8, colicin E9, colicin A, colicin S4, colicin 10, colicin R, colicin 28b, colicin Y, colicin Ia, colicin Ib, and cloacin DF13.

The invention also provides a composition containing a colicin or its derivative. The colicin may be selected from colicin M, colicin E7, colicin B, colicin Ia, colicin U, colicin K, colicin 5, colicin E5, colicin E8, colicin E9, colicin A, colicin S4, colicin 10, colicin R, colicin 28b, colicin Y, colicin Ib, and cloacin DF13, or a derivative of colicin M, colicin E7, colicin B, colicin Ia, colicin U, colicin K, colicin 5, colicin E5, colicin E8, colicin E9, colicin A, colicin S4, colicin 10, colicin R, colicin 28b, colicin Y, colicin Ib, and cloacin DF13. Colicin M or its derivative is preferred. Alternatively, the colicin may be any one or a combination of two or more of these colicins or derivatives of these colicins. In a preferred embodiment, the composition contains colicin M or its derivative and one or more further colicin selected from the group of colE7, colB, colIa, colU, colK, and/or col5, or a derivative of any of these colicins. More preferred embodiments are as follows:

- a composition containing colicin M or its derivative and colicin E7 or a derivative thereof;
- a composition containing colicin M or its derivative and colicin Ia or a derivative thereof;
- a composition containing colicin M or its derivative and colicin Ib or a derivative thereof;
- a composition containing colicin M or its derivative, colicin E7 or its derivative, colicin Ia or its derivative, and colicin K or its derivative;
- a composition containing colicin M or its derivative, colicin E7 or its derivative, colicin K or its derivative, colicin B or its derivative, and colicin 5 or its derivative.

If the composition contains more than one colicin or its derivative, the multiple colicins or their derivatives may be separately expressed in plants and purified to the desired degree. Thereafter, the colicins or their derivatives, or preparations containing the colicins may be combined. Binary colicin compositions, i.e. compositions containing two different colicins (or derivatives thereof) may be mixed from 1:10 to 10:1 by weight, preferably from 1:5 to 5:1 by weight. Further colicins (or their derivatives) may be added in comparable amounts. In the case of a combination of colicin M (or its derivative) and colicin E7 (or its derivative), they may be mixed in a weight ratio of from 1:3 to 5:1, preferably from 1:1 to 4:1. Where the composition is a solution, the total concentration of all colicins and any derivatives thereof in the solution may be from 1 to 100 000 µg/l, preferably from 10 to 50 000 µg/l, more preferably from 100 to 10 000 µg/l, and even more preferably from 500 to 5 000 µg/l.

The composition of the invention may further contain a solvent that dissolves the colicin(s) or its/their derivatives. The solvent is preferably water. Thus, the composition may be an aqueous solution of the colicins. For storage, such compositions may be cooled or frozen. In another embodiment, the composition is a freeze-dried solid obtained by lyophilization of an aqueous solution of the colicin(s) or its derivatives. The composition may further contain additives such as one or more preservatives, buffers, stabilizers and the like. As preservatives or stabilizers, those generally known to be compatible with food such as benzoic acid, glycerol, ascorbic acid, ethanol and the like may be mentioned. As buffers, substances mentioned above in the context of preventing or reducing contamination of an object with EPEC or EHEC may be mentioned.

Any of the above-mentioned colicins other than colicin M may be produced in plants as described above for colicin M. Introns may be inserted in the coding sequences to be expressed for ease of cloning. Further, coding sequences of the colicins may be codon optimized for expression in plants or in a particular plant. Accession numbers such as from the Uniprot database of the colicins are given in the Examples. In the following, the colicin amino acid sequences given in the database entries are referred to herein as "parent colicin" as opposed to the derivatives of the colicins.

The derivative of the colicins mentioned above may be a protein
  (A) comprising the known amino acid sequence of the parent colicin, and may have additional N- and/or C-terminal amino acid sequence stretches, such a purification tags;
  (B) comprising an amino acid sequence having an amino acid sequence identity of at least 80%, preferably of at least 85%, more preferably of at least 90%, even more preferably at least 95%, and most preferably of at least 97%, to the amino acid sequence of the parent colicin;
  (C) comprising an amino acid sequence similarity of at least 90%, preferably at least 95%, to the amino acid sequence of the parent colicin; similar amino acid residues are as defined above; and/or
  (D) comprising an amino acid sequence having from 1 to 30, preferably from 1 to 20, more preferably from 1 to 15, even more preferably from 1 to 10, and most preferably from 1 to 5, amino acid residue substitutions, insertions, additions and/or deletions compared to the amino acid sequence of the parent colicin; these number refer to the total of substitutions, insertions, additions and deletions;
  (E) comprising an amino acid sequence having from 1 to 30, preferably from 1 to 20, more preferably from 1 to 15, even more preferably from 1 to 10, and most preferably from 1 to 5, amino acid residue substitutions and/or terminal deletions compared to the amino acid sequence of the parent colicin. These numbers refer to the total of substitutions and terminal deletions.

The (parent) amino acid sequences of colicin E7 is given in SEQ ID NO: 6. The (parent) amino acid sequences of colicin Ia is given in SEQ ID NO: 7. The (parent) amino acid sequences of colicin Ib is given in SEQ ID NO: 8.

The derivatives of the above colicins (other than of colicin M), preferably have a minimum toxicity against an E. coli strain sensitive to the parent colicin compared to the parent colicin. The toxicity of the derivative of the colicin should be such that the derivative and the parent colicin produce spots free of viable bacteria of the sensitive E. coli strain of the same diameter 12 hours after spotting 5 microliters of a solution of said derivative of the colicin and the parent colicin onto a lawn of the sensitive E. coli strain on agar plates and subsequent incubation of the agar plates at 37° C., wherein the concentration of the derivative of the colicin is at most 5 times that of the comparative solution of the parent colicin. Preferably, the concentration of the derivative is at most 3 times, preferably at most twice that of the comparative solution of the parent colicin, and more preferably the same as that of the parent colicin. The colicin-sensitive E. coli strain may be any sensitive E. coli strain. For convenience, E. coli strain DH10B may be used for testing the toxicity of the colicin and its derivative. Otherwise, the assay described in Example 3 may be employed analogously. Thus, the radial diffusion assays via spot-on-lawn-method may be used. Similarly as decribed above for colicin M, the agar plates for the assay may be overlaid with soft agar containing cells of tested E. coli strain. 10×10 cm quadratic petri dishes may be poured with 15-20 ml LB agar medium (1.5% w/v agar). LB soft agar medium (0.8% (w/v) agar) is melted, 20 ml aliquots are transferred into 50 ml plastic tubes and their temperature is adapted to 50-55° C. E. coli overnight cultures of the test bacteria adjusted to OD600=1.0 with LB medium are added to the soft agar medium in a ratio of 200 µl bacterial culture per 20 ml medium resulting in the final OD600=0.01 or approximately 1×10$^7$ cells/ml. Raw colicin preparations such as plant leaf material containing expressed colicin or its derivative may be extracted as described in Example 2. A 1:1 dilution series of plant extracts starting with undiluted samples by using extraction buffer may be prepared. 5 µl aliquots of total soluble protein (TSP) dilution series may be applied to the agar plates that are then incubated at 37° C. overnight. Antimicrobial activity (toxicity) of the colicin or its derivative can be evaluated visually based on clearing zones and the diameter of spots may be measured.

If a colicin as described above such as colicin M or a derivative thereof is used for preventing infection of a mammal with enterohaemorrhagic E. coli, the colicin may be administered to the mammal. The mammal is preferably a human. Further, colicin M or a derivative thereof, or combinations of colicin M or its derivative with other colicins (or their derivatives) as described above may be used for reducing the load of EHEC in ruminants such as cattle (e.g. cows) or sheep. Generally, a liquid or solid pharmaceutical composition containing the colicin such as the colicin M or a derivative thereof, or combinations with other colicins or their derivatives, is prepared for administration to the mammal. Liquid compositions may be aqueous solutions. Solid compositions may be tablets containing the colicin such as the colicin M or its derivative, or combinations of colicin M or its derivative with other colicins (or their derivatives), e.g. in freeze-dried form. Administration may be oral. In this case, the pharmaceutical preparation is one that allows passage through the stomach without being attacked by the acid medium in the stomach. The colicins or their derivatives should then be released from the pharmaceutical preparation in the intestine. Such pharmaceutical preparations are known in the art. Examples are tablets and capsules resistant to the acid medium in the stomach. It is further possible to administer orally a biological material such as E. coli or plant material containing expressed colicin such as colicin M or a derivative thereof to a patient. The colicin such as the colicin M or its derivative may be administered to an adult in amounts of 1 mg to 1000 mg per day, preferably of from 10 mg to 250 mg per day to a human patient.

Similarly as described above for the method of reducing or preventing contamination with EHEC, or the method or reducing the load of EHEC in ruminants, colicin M or its derivative can be combined with any one or more other colicins such as with colE7, colB, colIa, colU, colK, col5, col Ia or col Ib for preventing infection of a patient with EHEC such as any one or all of the following *E. coli* serotypes: O26:H11, O45:H2, O103:H11, O111:H8, O145: NM, O157:H7, O104:H4, and O121:H19.

In a probiotic approach, a patient may be treated by administering to the patient a genetically-modified microorganism expressing a colicin such as colicin M or its derivative. The genetically-modified microorganism may be a genetically-modified non-pathogenic *E. coli* or a lactic acid-producing microorganism as commonly employed in fermentation of milk products. Examples of lactic acid-producing microorganism are bacteria from the genera *Lactobacillus* such *Lactobacillus lactis* and *Bifidobacterium* such as *Bifidobacterium bifidium* or *Bifidobacterium breve*.

Another route of administration is by injection into the blood stream of a patient for preventing infection with EHEC or EPEC. For this purpose the colicin such as the colicin M or a derivative, or combinations of colicin M or its derivative with other colicins (or their derivatives), may be dissolved in a physiological saline and the solution be sterilized.

EXAMPLES

Example 1: Plasmid Constructs

Twelve colicins representing all four activity groups and various receptor specificities were selected (Table 1).

TABLE 1

List of colicins used in Examples

| No. | Colicin | Receptor | Activity | Accession No. |
|---|---|---|---|---|
| 1 | colE2 | BtuB | DNase | AAA23068.1 |
| 2 | colE3 | BtuB | RNase | AAA88416.1 |
| 3 | colE6 | BtuB | RNase | AAA23080.1 |
| 4 | colE7 | BtuB | DNase | AAA98054.1 |
| 5 | colD | FepA | tRNase | P17998.1 |
| 6 | colN | OmpF, LPS | pore-forming | P08083.1 |
| 7 | colK | Tsx | pore-forming | Q47502.1 |
| 8 | col5 | Tsx | pore-forming | CAA61102.1 |
| 9 | colU | OmpA | pore-forming | CAA72509.1 |
| 10 | colB | FepA | pore-forming | P05819.3 |
| 11 | colIa | Cir | pore-forming | WP_001283344.1 |
| 12 | colM | FhuA | inhibition of cell wall synthesis | AAA23589.1 |

The list comprises colicins E2, E3, E6, E7, D, N, K, 5, U, B, Ia and M. Respective amino acid sequences were retrieved from GenBank; corresponding nucleotide sequences with codon usage optimized for *Nicotiana benthamiana* were synthesized by Life Technologies GmbH (Darmstadt, Germany). In case of colicins E2, E3, E6, E7 and M, the coding sequence was interrupted by insertion of the cat 1 intron (the first intron from *Ricinus communis* cat1 gene for catalase CAT1 (GenBank: D21161.1, nucleotide positions between 679 and 867)) to prevent the cytotoxicity in *Escherichia coli* cells used for cloning. Colicin coding sequences were inserted into TMV-based assembled viral vector pNMD035 (described in detail in WO2012/019660) resulting in plasmid constructs depicted in FIGS. 1A-1C.

In preliminary expression studies, it was found that colicins with nuclease (RNase and DNase) activities are usually highly toxic for plant tissues where they are expressed. Their expression resulted in tissue necrosis and poor accumulation of recombinant protein. However, co-expression with appropriate immunity proteins reduced the toxic effect and increased the accumulation of these colicins dramatically. Colicin immunity proteins used in our studies are listed in the Table 2.

TABLE 2

List of immunity proteins used in examples

| No. | Immunity protein | Specificity | Accession No. |
|---|---|---|---|
| 1 | ImmE2 | colE2 (DNase) | AAA23069.1 |
| 3 | ImmE6 | colE6 (RNase) | AAA23081.1 |
| 4 | ImmE7 | colE7 (DNase) | AAA23071.1 |
| 5 | ImmD | colD (tRNase) | P11899.2 |

Figure 1A:
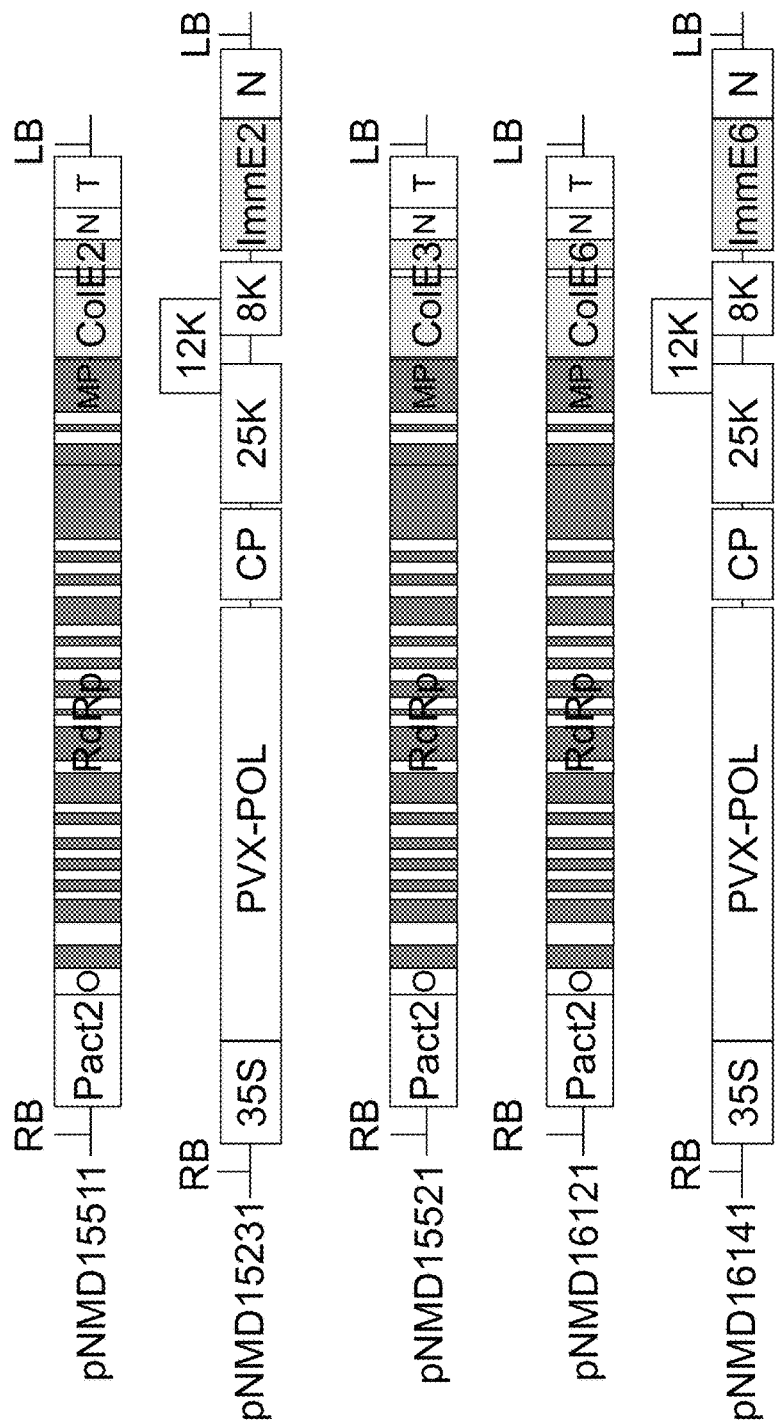
FIGS. 1A-1C show schematically viral vectors for the expression of colicins and corresponding immunity proteins used in the Examples. Constructs for the expression of colicins are based on Tobacco mosaic virus (TMV), whereas constructs for the expression of immunity proteins are based on Potato virus X (PVX).
Figure 1B:
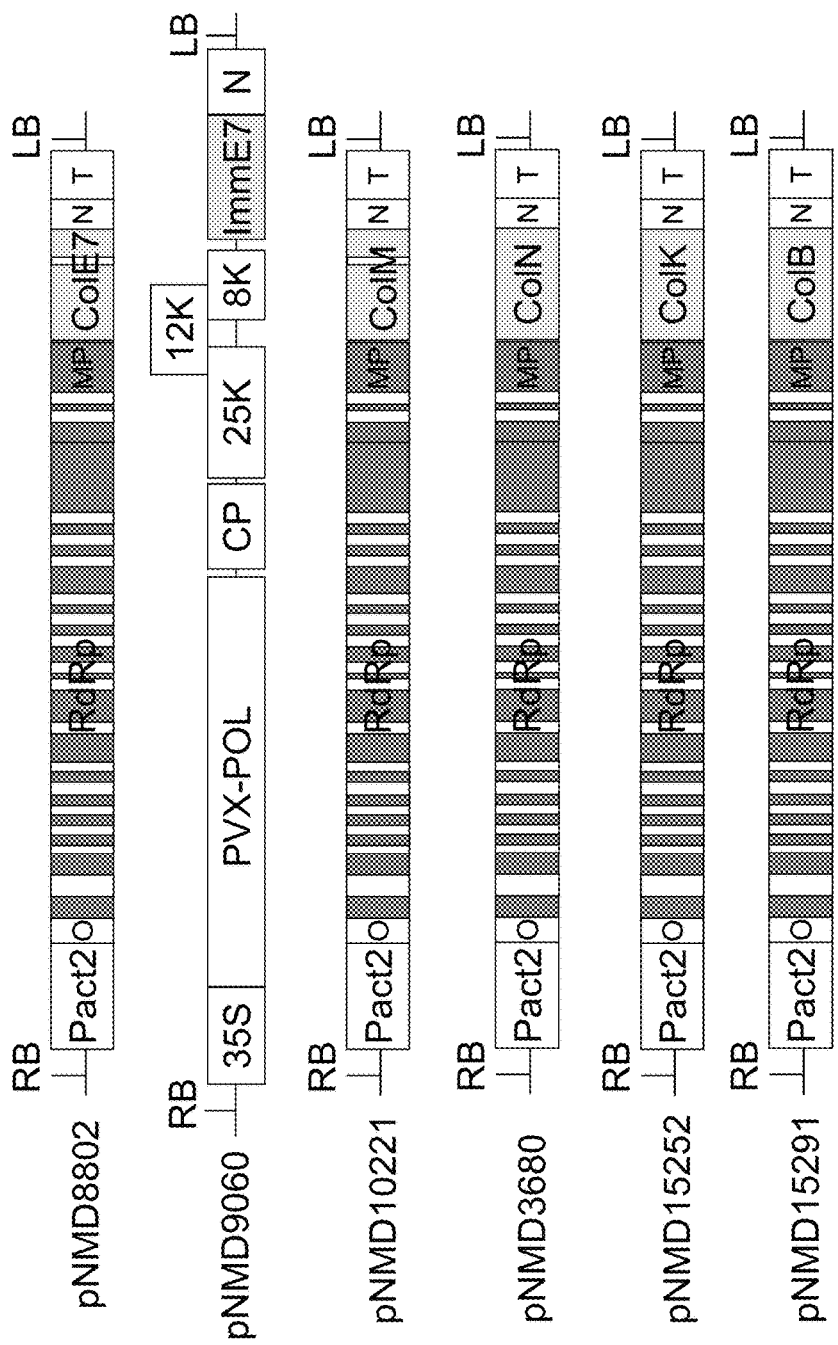
Figure 1C:
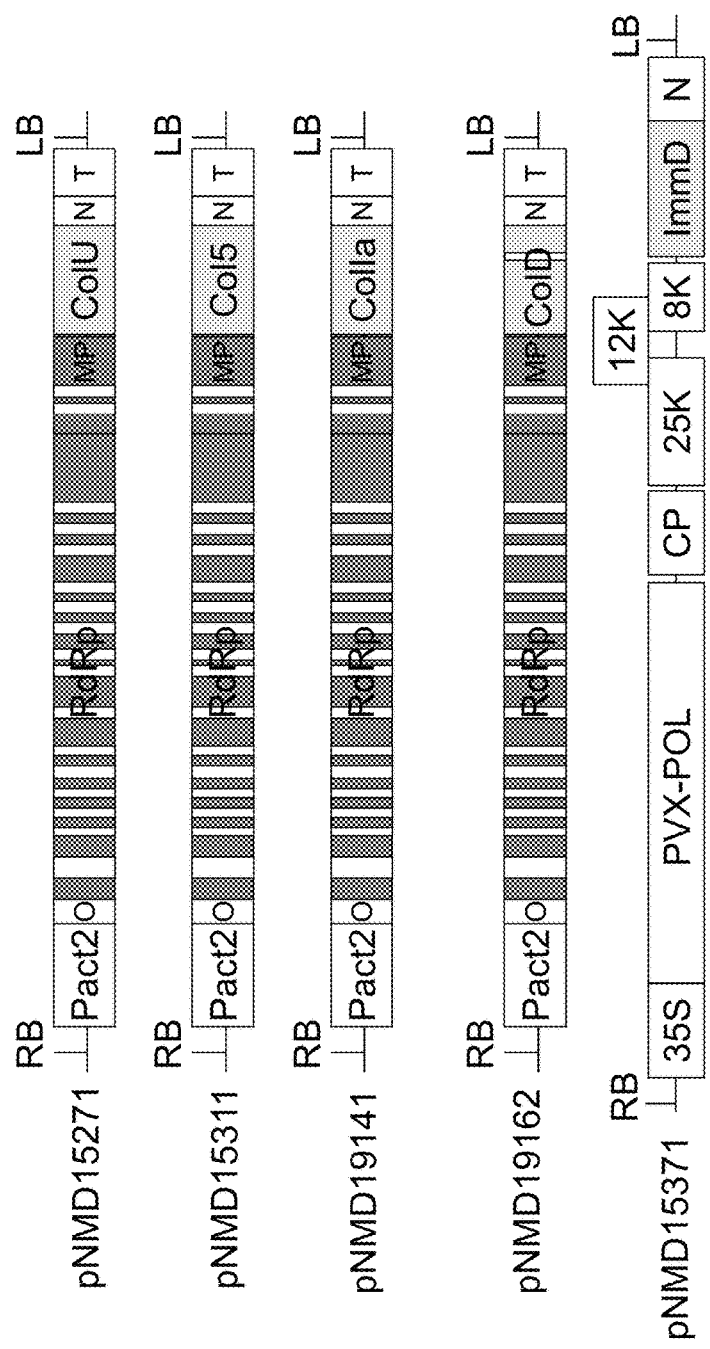

Immunity proteins ImmE2, ImmE6, ImmE7 and ImmD are specific for colicins E2, E6, E7 and D, respectively. Amino acid sequences of immunity proteins were retrieved from GenBank; corresponding nucleotide sequences with codon usage optimized for *Nicotiana benthamiana* were synthesized by Life Technologies and subcloned into PVX-based assembled viral vector pNMD670 as described in WO2012/019660. Resulting plasmid constructs are shown in FIGS. 1A-1C.

For colicin M, several other constructs were created. They include TMV-based vector pMD10240 for chloroplast targeting of colicin M protein expressed as a translational fusion with chloroplast targeting pre-sequence (Marillonnet et al. 2004). Two other constructs are PVX-based viral vectors for cytosolic accumulation (pNMD11740) and chloroplast targeting (pNMD14500) of colicin M.

pNMD18381, the double-inducible viral vector for ethanol-induced Colicin M expression was created using the Golden Gate Modular Cloning approach (Engler et al. 2009; Weber et al. 2011; WO 2011/154147). This vector was further used for stable transformation of *Nicotiana benthamiana* plants.

Basically, level 0 vectors were generated by PCR amplification of modules with flanking BsaI endonuclease restriction sites bearing specific nucleotide sequences in sticky end regions and cloning of BsaI-restricted PCR fragments into BpiI-restricted level 1 entry cloning vectors with matching sticky end regions. Five different types of modules were used: 1) promoter module (P; BsaI 5'GGAG/BsaI 3'TACT); 2) 5'NTR module (5'non-translated region; BsaI 5' TACT/BsaI 3AATG), 3) ORF module (open reading frame; BsaI 5'AATG/BsaI 3'GCTT), 4) 3'NTR module (3'non-translated region; BsaI 5' GCTT/BsaI 3'GGTA) and 5) terminator module (T; BsaI 5'GCTT or Bsa 5'GGTA/BsaI 3'CGCT). Nucleotide sequences were verified by sequencing.

Four different expression cassettes were assembled by single pot BsaI cloning of level 0 modules into BsaI sites of level 1 destination vectors which are flanked by BpiI sites with specific nucleotide sequences in sticky end regions for position and orientation of expression cassettes as: position 1, reverse (BpiI 5'GCC/BpiI 3'GCAA); position 2, forward (BpiI 5'GCAA/BpiI 3'ACTA); position 3, reverse (BpiI 5' ACTA/BpiI 3'TTAC); position 4, forward (BpiI 5'TAC/BpiI 3'CAGA). Generated level 1 expression cassette vectors were: pNMD3420 (position 1, reverse; in pICH41344 (level 1 destination vector); pNMD3320 (level 0 promoter module vector, nos P (*Agrobacterium tumefaciens* nopaline synthase promoter)); pICH41403 (level 0 5'NTR module vector, Ω translational enhancer from TMV); pNMD3410 (level 0 ORF module vector, NPTII (neomycine phosphotransferase II); and pNMD3330 (level 0 terminator module vector, nos T (*Agrobacterium tumefaciens* nopaline synthase terminator)); pNMD13981 (position 2, forward; pICH47742 (level 1 destination vector), pICH41551 (level 0 promoter module vector, pSTLS (potato ST-LS1 gene promoter, GenBank: X04753.1)), pICH41571 (level 0 5'NTR-ORF module vector, alcR (Werner at al. 2011)), pICH53411 (level 0 3'NTR module vector, U1 3'NTR (3'non-translated region of Tobacco mosaic virus U1 isolate)), pICH53461 (level 0 terminator module vector, act2-t (*Arabidopsis actin* 2 terminator)); pNMD14002 (position 3, reverse; pICH47822 (level 1 destination vector), pICH41561 (level 0 promoter module vector, pAlcA (a/cA promoter from *Aspergillus nidulans* fused with minimal 35S promoter sequence (Werner at al. 2011)), pICH52122 (level 0 5"NTR module vector, RdRp TVCV viral RNA-dependant RNA polymerase with 9 introns), pICH58391 (level 0 ORF module vector, LacZ), pICH45567 (level 0 terminator module vector, 3"NTR and 35S-t (TVCV viral 3"-nontranslated region and CaMV 35S terminator)); pNMD4590 (position 4, forward; pICH47761 (level 1 destination vector), pNMD4571 (level 0 promoter module vector, lambda insulator (999 bp long fragment between nucleotide position 31748 to 32746 of *Enterobacteria* phage lambda genome, GenBank: J02459.1) fused to a/cA promoter), pICH41581 (level 0 5"NTR-ORF module vector, MP (viral movement protein) and 5"NTR), pICH53411 (level 0 3"NTR module vector, U1 3"NTR), pICH53444 (level 0 terminator module vector, ocs-t (*Agrobacterium tumefaciens* octopine synthase promoter)). Level 2 binary expression vector with kanamycin resistance selection marker on the vector backbone and a T-DNA consisting of 4 expression cassettes in different orientations flanked by left and right border was generated by single pot Bpil cloning using pICH45066 (level 2 destination vector (Bpil 5'TGCC/Bpil 3'GGGA)), pNMD3420 (level 1 vector, position 1, reverse; kanamycin plant selection marker expression cassette), pNMD13981 (level 1 vector, position 2, forward; a/cR transcriptional regulator expression cassette), pNMD14002 (level 1 vector, position 3, reverse; viral expression cassette for gene of interest containing lacZ for counterselection) pNMD4590 (level 1 vector, position 4, forward; expression cassette for viral MP for cell-to-cell movement), pICH41780 (end-linker to bridge expression cassette 4 and vector backbone).

Colicin M sequence from *E. coli* (AAA23589.1) was codon-optimized for *N. benthamiana*; cat 1 intron was inserted at position corresponding to codon G81 and the corresponding DNA was synthesized by Life Technologies GmbH (Darmstadt, Germany). Level 0 ORF module vector containing PCR-cloned colM, pNMD18371, was used to replace LacZ in position 3 expression cassette of level 2 binary destination vector pNMD14021 by Bsal cloning to generate pNMD18381.

Example 2: Colicin Expression Screening 6 weeks old *Nicotiana benthamiana* plants were infiltrated using needleless syringe with diluted *Agrobacterium tumefaciens* cultures carrying TMV-based assembled vectors for cytosolic colicin expression. In case of colicins E2, E6, E7 and D, *Agrobacterium* cultures carrying TMV-based vector for colicin expression were mixed in equal proportions with other cultures carrying PVX-based vectors for the expression of corresponding immunity proteins. Individual overnight cultures were adjusted to OD600=1.5 and further diluted 1:100 with infiltration buffer containing 10 mM MES, pH 5.5 and 10 mM MgSO4. Plasmid constructs used in this experiment are summarized in Table 3. One week post infiltration, plant material was harvested and used for protein extraction. Total soluble protein (TSP) concentration was determined using the Bradford assay, and TSP extracts were analyzed using SDS-PAGE with Coomasssie staining. In our experiment, all tested colicins were expressed on reasonably high levels varying between 0.4 and 6.3 mg recombinant colicin/g FW or 6 and 50% of TSP (Table 4) as determined by comparison with bovine serum albumin (BSA) protein.

TABLE 3

Summary of colicin expression screen

| No. | Colicin | Construct | Construct (feature) |
|---|---|---|---|
| 1 | colE2/ImmE2 | pNMD15511/pNMD15231 | TMV/PVX |
| 2 | colE3 | pNMD15521 | TMV |
| 3 | colE6/ImmE6 | pNMD16121/pNMD16141 | TMV |
| 4 | colE7/ImmE7 | pNMD8802/pNMD9060 | TMV/PVX |
| 5 | colD/ImmD | pNMD19162/pNMD19183 | TMV/PVX |
| 6 | colN | pNMD3680 | TMV |
| 7 | colK | pNMD15252 | TMV |
| 8 | col5 | pNMD15311 | TMV |
| 9 | colU | pNMD15271 | TMV |
| 10 | colB | pNMD15291 | TMV |
| 11 | colIa | pNMD19141 | TMV |

TABLE 4

Yield of recombinant colicins expressed in *Nicotiana benthamiana* plants. FW stands for fresh weight, TSP for total soluble protein.

| No. | Colicin | Yield (mg/g FW) | Yield (% TSP) |
|---|---|---|---|
| 1 | Colicin E2 | 2.1 | 20 |
| 2 | Colicin E3 | 0.6 | 7 |
| 3 | Colicin E6 | 3.99 | 38 |
| 4 | Colicin E7 | 1.17 | 13 |
| 5 | Colicin D | 1.1 | 10 |
| 6 | Colicin N | 0.63 | 7 |
| 7 | Colicin K | 2.13 | 25 |
| 8 | Colicin 5 | 6.25 | 50 |
| 9 | Colicin U | 0.42 | 6 |
| 10 | Colicin B | 1.8 | 19 |
| 11 | Colicin Ia | 0.7 | 10 |
| 12 | Colicin M | 1.17 | 13 |

Example 3: Colicin Activity Screen

We analyzed the antimicrobial activity of plant-made recombinant colicins against the Big 7 STEC strains and against emerging O104:H4 EHEC strain. Details of standard quality control strains of Big 7 (#5219, Microbiologics Inc., St. Cloud, Minn., USA) and O104:H4 (#01104, Microbiologics Inc.) used in our experiments are given in Table 5.

TABLE 5

EHEC strains used for antimicrobial activity screen

| No. | Strain | Characteristics |
|---|---|---|
| 1 | *E. coli*, serotype O26:H11 (CDC03-3014) | Big 7 STEC QC Set (#5219, Microbiologics) |
| 2 | *E. coli*, serotype O45:H2 (CDC00-3039) | (positive for presence of virulence genes stx1 |

TABLE 5-continued

EHEC strains used for antimicrobial activity screen

| No. | Strain | Characteristics |
|---|---|---|
| 3 | E. coli, serotype O103:H11 (CDC06-3008) | and/or stx2 and eae) |
| 4 | E. coli, serotype O111:H8 (CDC2010C-3114) | |
| 5 | E. coli, serotype O121:H19 (CDC02-3211) | |
| 6 | E. coli, serotype O145:NM (CDC99-3311) | |
| 7 | E. coli, serotype O157:H7 (ATCC 35150) | |
| 8 | E. coli, serotype O104:H4 (ATCC BAA-2326) | QC control strain (#01104, Microbiologics) emerging EHEC |

Antimicrobial activity of recombinant colicin-containing plant extracts was tested in radial diffusion assays via spot-on-lawn-method. For this purpose, we prepared agar plates overlaid with soft agar containing cells of tested E. coli strains. 10×10 cm quadratic petri dishes were poured with 15-20 ml LB agar medium (1.5% w/v agar). LB soft agar medium (0.8% (w/v) agar) was melted, 20 ml aliquots were transferred into 50 ml plastic tubes and their temperature was adapted to 50-55° C. E. coli overnight cultures adjusted to OD600=1.0 with LB medium were added to the soft agar medium with a ratio of 200 µl bacterial culture per 20 ml medium resulting in the final OD600=0.01 or approximately $1 \times 10^7$ cells/ml. Plates for each strain were prepared in duplicate.

Plant leaf material was extracted as described in Example 2. We prepared 1:1 dilution series of plant extracts starting with undiluted samples by using same extraction buffer. 5 µl aliquots of TSP dilution series were applied to agar plates; plates were incubated at 37° C. overnight. Antimicrobial activity was evaluated based on clearing zones. Colicins significantly differed in their specificity and potency of antimicrobial activity against different EHEC strains. The majority of tested colicins demonstrated rather narrow strain specificity with reasonably high activity against 1-3 strains. Surprisingly, the broadest specificity combined with relatively high potency against different strains was found for colicin M.

For semi-quantitative comparison, we represented relative antimicrobial activity of recombinant colicins in arbitrary units (AU), calculated as a dilution factor for the highest dilution of protein extract causing the detectable clearing effect in the radial diffusion assay. Colicin antimicrobial activity against Big 7 STEC strains calculated in AU per mg FW of the plant tissue is shown in FIG. 5. FIG. 6 demonstrates the same activity calculated in AU per µg of colicin protein. Both figures show the superiority of colicin M over other colicins concerning the spectrum of antimicrobial activity (FIG. 6) and the yield of active antimicrobial agent in plant tissue (FIG. 5). FIGS. 7A-7B shows the activity of tested recombinant colicin proteins against O104: H4 strain represented in either AU/mg FW (FIG. 7A) or AU/µg colicin (FIG. 7B). This strain is quite sensitive to the majority of tested colicins, however, colicins E2, E6, E7 and M are most active against this strain.

To summarize, colicin M shows the broadest antimicrobial activity against tested EHEC strains. Thus, it can be used as a main ingredient of colicin cocktails for the control of EHEC.

Example 4: Transient Expression of Colicin M in Nicotiana benthamiana with Different Viral Vectors 6 weeks old Nicotiana benthamiana plants were infiltrated using needleless syringe with diluted suspension of Agrobacterium tumefaciens GV3101 cells carrying TMV-based assembled vector pNMD10221 or PVX-based assembled vector pNMD11740 (FIG. 2). For infiltration, OD600 of overnight cultures was adjusted to 1.5 and further diluted 1:100 with infiltration buffer containing 10 mM MES (pH 5.5) and 10 mM MgSO4. Plant phenotype was analyzed and leaf samples were harvested after 4, 5, 6, 7 and 9 days post infiltration (dpi). Total soluble extracts were prepared at different harvesting time points by grinding the plant tissue in liquid nitrogen and adding of 5 volumes of extraction buffer followed by incubation for 30 min on ice. The extraction buffer contained 20 mM acetate; 250 mM sodium chloride; 15 mM sodium ascorbate, 10 mM sodium metabisulfite (pH 4.0).

The analysis of the plant phenotype revealed no necrosis till 9 dpi when plants were infiltrated with the PVX based construct, whereas some necrosis at 9 dpi appeared when leaves were infiltrated with the TMV based construct. SDS-PAGE analysis revealed a high expression of ColM after the inoculation with both vectors (FIG. 8). The TMV based expression, however, resulted in higher accumulation of the protein of interest. The optimal harvesting time found for both vectors was 6 or 7 days post infiltration.

Example 5: Expression of Colicin M in Edible Plants

We successfully expressed Colicin M in the spinach and the beet plants.

7.5 weeks old plants of spinach Spinacea oleracea were infiltrated using syringe without needle with diluted suspension of Agrobacterium tumefaciens cells (ICF320 or GV3101 strains) carrying TMV-based assembled vector pNMD10220. Plant phenotypes were analyzed and plant material was harvested at 6, 8 and 10 dpi. For infiltration, OD600 of overnight cultures was adjusted to 1.5 and further diluted 1:100 with infiltration buffer containing 10 mM MES (pH 5.5) and 10 mM MgSO4. No necrotic phenotype was observed until last harvesting time point of 10 dpi. SDS-PAGE analysis of TSP extracts revealed abundant protein bands in Coomassie-stained gels without significant difference between the two Agrobacterium strains (FIG. 9A).

Beta vulgaris ssp. maritima (the sea beet) plants were infiltrated by syringe with 1:100 dilutions of Agrobacterium cultures of ICF320 and GV3101 strains for expression of cytosolic Colicin M using an assembled TMV based vector pNMD10220. Plant phenotypes were analyzed and plant material was harvested at 6, 8 and 10 dpi. Some necrosis was observed in the infiltrated areas at 10 dpi which seemed to be stronger for GV3101 strain compared to ICF320. SDS-PAGE analysis revealed detectable protein bands in Coomassie stained gels with a peak of recombinant protein accumulation at 8 dpi (FIG. 9B). The decrease of Colicin M level observed at 10 dpi correlated with leaf necrosis.

Example 6: Ethanol-Inducible Expression of Colicin M in Stable Transgenic Nicotiana benthamiana Plants For ethanol-inducible Colicin M expression, we generated stable transgenic Nicotiana benthamiana plants containing the genomic insertion of a double-inducible TMV-based viral vector (the approach is described in Werner et al. 2011).

The pNMD18381 construct (FIG. 3) created for this purpose was first tested in transient assay. Leaves of 5.5 weeks old *Nicotiana benthamiana* plants were infiltrated with a suspension of *Agrobacterium tumefaciens* cells of OD600=1.3 diluted 1:100 with a buffer for infiltration (10 mM MES, pH5.5; 10 mM MgSO4) using the syringe without needle. 2 days post infiltration, plants were sprayed with 4% (v/v) ethanol and drenched each plant with 40 ml of 4% (v/v) ethanol, incubated under plastic box with 500 ml of 4% (v/v) ethanol for 24 h (for 4 plants). Leaf material was harvested 4 days post induction. For SDS-PAGE analysis, leaf samples were extracted with 5 volumes of Laemmli buffer, resolved in 12% polyacrylamide gel and stained with Coomassie. SDS-PAGE analysis detected the specific protein bands in ethanol-induced tissue (FIG. 10).

Construct pNMD18381 was transformed into *Nicotiana benthamiana* with *Agrobacterium*-mediated leaf disc transformation and selection on kanamycin-containing medium using a slightly modified standard protocol (Horsch et al. 1985; Werner et al. 2011). Regenerated plants were transferred to the greenhouse and tested for Colicin M expression upon ethanol induction.

Ethanol-inducible transgene expression was tested in detached leaves. Each leaf (one per plant) was incubated in 12.5 cm petri dish containing one layer of Whatman filter paper (10 cm in diameter) moisturized with 5 ml of 4% (v/v) ethanol and one layer of glass fibre mesh (10 cm in diameter) (Fiberglasgewebe für Licht- and Kellerschachte, Schellenberg, Germany). After 2 days incubation (fluorescent light, 22° C.), leaves were transferred into new petri dishes as described above but moisturized with water (15 ml in total) and incubated 3 additional days at same conditions. 4 days post induction 100 mg samples of plant material were harvested and frozen in liquid nitrogen.

SDS-PAGE analysis was performed as described above for the transient assay. The accumulation of Colicin M protein upon ethanol induction was shown for the majority of selected transgenic lines (FIG. 10).

Example 7: Colicin M Inhibition of 'Big Seven' STEC and EAHEC O104:H4 Strains in Broth Culture

*E. coli* cultures were grown overnight in liquid LB medium, diluted with a fresh LB medium to $OD_{600}=0.05$ and further grown to $OD_{600}=0.3$. After that, we prepared 100 ml cultures via dilution with fresh LB medium to approx. $1\times10^4$ cfu/ml (predilution to $OD_{600}=0.3$, dilute 1:3000). Each culture was aliquoted into 6 flasks (each containing 14 ml). Aliquot of the culture was taken for dilution plating (T=0 min). After addition of 1 ml of analyzed plant TSP extract with known colicin concentration, cultures were incubated at 37° C. with 150 rpm agitation. Aliquots for dilution plating were taken at 30, 60 and 90 min of incubation. 100 μl aliquots of bacterial cultures were plated on LB agar medium; plates were incubated at 37° C. overnight and used for colony counting next day. The plating was done in triplicate; bacterial population in the tested liquid cultures was evaluated as a number of cfu (colony forming units) per ml.

Table 6 shows the reduction of bacterial population after the application of colicin M (colicin containing plant extract was compared with the extract from uninfected *Nicotiana benthamiana* plants). Significant reduction of bacterial population was demonstrated for individual strains as well as for the mixture of all Big 7 strains.

Table 7 shows the result of application of colicin M mixed with colicin E7. These two colicins demonstrated synergistic effect for certain EHEC strains. Using a mixture of two or more colicins may be used for decreasing the amount of applied proteins.

TABLE 6

Antibacterial activity of colicin M applied individually to STEC strains

| *E. coli* strain | Colicin M (mg/l) | *E. coli* cells (cfu/ml) | |
|---|---|---|---|
| | | Reduction log | Initial cell number |
| O103:H11 | 7.5 | 2.6 | $0.9 \times 10^4$ |
| O45:H2 | 7.5 | 2.7 | $1.3 \times 10^4$ |
| O111:H8 | 3.75 | 4.1 | $1.5 \times 10^4$ |
| O26:H11 | 3.75 | 5.0 | $1.1 \times 10^4$ |
| O157:H7 | 1 | 3.5 | $1.2 \times 10^5$ |
| Mix of Big 7 strains | 1 | 0.8 | $1.0 \times 10^4$ |
| O104:H4 | 1 | 5.0 | $1.0 \times 10^4$ |

TABLE 7

Antibacterial activity of colicin M and colicin E7 applied as mixtures to STEC strains

| *E. coli* strain | Colicin M + colicin E7 (mg/l) | *E. coli* cells (cfu/ml) | |
|---|---|---|---|
| | | Reduction log | Initial cell number |
| O121:H19 | 1 + 1 | 2.8 | $0.7 \times 10^4$ |
| O145:NM | 1 + 1 | 0.8 | $2.3 \times 10^4$ |
| O103:H11 | 1 + 1 | 0.9 | $1.8 \times 10^4$ |
| O45:H2 | 1 + 1 | 0.9 | $1.3 \times 10^4$ |
| O111:H8 | 0.5 + 0.5 | 5.2 | $0.8 \times 10^4$ |
| O26:H11 | 0.5 + 0.5 | 4.4 | $0.7 \times 10^4$ |
| O157:H7 | 0.25 + 0.25 | 3.6 | $1.1 \times 10^5$ |
| Mix of Big 7 strains | 1 + 1 | 0.9 | $1.4 \times 10^4$ |
| O104:H4 | 0.1 + 0.1 | >6.1 | $1.4 \times 10^4$ |

Example 8: Treatment of *E. coli* Contaminated Steak Meat Pieces with Two-Component Colicin Mixture Consisting of Colicin M And Colicin E7

Plant-produced colicins were tested for antibacterial activity on samples of meat steak contaminated with pathogenic *E. coli*.

Pork fillet steaks were purchased in the local supermarket. Steaks were trimmed to a final weight of each 85 g using a sterile scalpel and put into 12×12 cm sterile petri dishes. *E. coli* O157:H7 inoculum, strain DSM19206, was prepared by dilution of a saturated LB overnight culture to $OD_{600}=0.05$ and a freshly grown LB culture at end of exponential phase ($OD_{600}\approx0.3$) was diluted to $OD_{600}=0.005$ (approx. $5\times10^5$ cfu/ml) by dilution with LB medium. Each steak was inoculated with *E. coli* by dipping from both sides into 12 ml of this bacterial solution in 12×12 cm sterile petri dishes. Upon inoculation, steaks were dried for 30 min at room temperature and turned around upon 15 min. The solutions for carrier or colicin treatment were prepared by extraction of *N. benthamiana* leaf material expressing colicin M or colicin E7 or *N. benthamiana* uninfected wild type leaf material stored at −80° C. and ground to fine powder in liquid nitrogen with 5 volumes prechilled buffer (50 mM HEPES (pH7.0), 10 mM potassium acetate, 5 mM magnesium acetate, 10% (v/v) glycerol, 0.05% (v/v) Tween®20 (Sigma-Aldrich, St. Louis, Mo., USA) and 300 mM sodium chloride), respectively. Steaks inoculated with E. coli were treated with carrier solution or colicin solution (3 mg colM+1 mg colE7/kg meat) by spraying in total 1.6 ml on both sides of a 85 g steak, non-treated (E. coli inoculation only) steaks served as control. Steaks were dried again at room temperature for 45 min and turned around upon 20 min. Afterwards, aliquots of steaks of about 20 g were packed for microbial analysis and storage into lateral filter bags BagFilterOP (Interscience, St Nom Ia Bretêche, France). After a total incubation time of 1.5 hours at room temperature upon colicin treatment, samples were incubated for 1 hour, 1 day or 3 days at 10° C. before microbial analysis. Samples were inspected in quadruplicates for microbes by homogenization of steaks with 5 volumes of peptone water for 30 s using BagMixer®400CC (Interscience, St Nom Ia Bretêche, France) and analysis of homogenized material from filtered part of the bag by dilution plating on sorbitol-MacConkey medium supplemented with 0.05 μg/ml cefixime and 100 μg/ml X-Gluc for O157:H7 cfu numbers.

The results of bacteria count is shown in FIG. 11. Most significant reduction of bacterial population (2.3 logs) occurred already after 1 hour storage. More prolonged storage resulted in further decrease of bacterial population.

Example 9: Treatment of E. coli Contaminated Fresh-Cut RTE Pieces of Melon with Two-Component Colicin Mixture Consisting of Colicin M and Colicin E7

Ready-to-eat (RTE) cut segments of melon were infected with E. coli O157:H7 as an indicator pathogen and then sprayed with a two-component (colicins M+E7 formulations) and the results were compared to washing alone and spraying a control carrier solution containing plant extract without colicins.

Cantaloupe melon was purchased in the local supermarket and surface-sterilized by incubation of one fruit in 2 liters of 200 ppm sodium hypochlorite solution prepared with sterile tap water for 5 min with subsequent washing in 2 liters sterile tap water. Fruit pieces were prepared by cutting melon into flat pieces (thickness of approx. 1 cm) of suitable size using knifes and chopping board cleaned with Bacillol, only fruit pulp after removal of kernels and rind was used. 10 pieces corresponding to approx. 65 g were aliquoted into 12×12 cm sterile petri dishes.

E. coli O157:H7 inoculum, strain DSM19206, was prepared by dilution of a saturated LB overnight culture to $OD_{600}$=0.05 and a freshly grown LB culture at the end of exponential phase ($OD_{600}$≈0.3) was diluted to $OD_{600}$=0.001 (approx. 1×10$^5$ cfu/ml) by dilution with sterile tap water. Each 10 fruit pieces were inoculated with E. coli by dipping from both sides into 12 ml of this bacterial solution in 12×12 cm sterile petri dishes. Upon inoculation, fruit pieces were dried for 30 min at room temperature and turned around upon 15 min. The solution for carrier or colicin treatment were prepared by extraction of N. benthamiana leaf material expressing colicin M or colicin E7 or N. benthamiana wild type leaf material stored at −80° C. and ground to fine powder in liquid nitrogen with 5 volumes prechilled buffer (50 mM HEPES (pH7.0), 10 mM potassium acetate, 5 mM magnesium acetate, 10% (v/v) glycerol, 0.05% (v/v) Tween®20, 300 mM sodium chloride), respectively. Melon pieces inoculated with E. coli were treated with carrier solution or colicin solution (3 mg colM+1 mg colE7/kg fruit) by spraying in total 1.8 ml on both sides of 65 g fruit pieces. Non-treated fruit pieces (E. coli inoculation only) served as control. Fruit pieces were dried again at RT for 30 min and turned around upon 15 min. Afterwards, aliquots of fruit pieces of about 20 g were packed for microbial analysis and storage into lateral filter bags BagFilter®P. Upon a total incubation time of 1 hour at room temperature upon colicin treatment, samples were incubated for 1 hour, 1 day or 3 days at 4° C. before microbial analysis. Samples were inspected in quadruplicates for microbes by homogenization of fruit pieces with 5 volumes peptone water for 30 s using BagMixer®400CC and analysis of homogenized material from filtered part of the bag by dilution plating on sorbitol-MacConkey medium supplemented with 0.05 μg/ml cefixime and 100 μg/ml X-Gluc for O157:H7 cfu numbers.

Results of colicin spray treatment of RTE melon segments are summarized in FIG. 12. Colicin treatment resulted in approx. 1 log reduction of bacterial population if compared with a treatment with spray carrier only.

Example 10: Treatment of E. coli Contaminated Fresh-Cut RTE Pieces of Apple with Two-Component Colicin Mixture (Colicin M and Colicin E7) and Five-Component Colicin Mixture (Colicin M, Colicin E7, Colicin K, Colicin B, Colicin 5)

A similar exposure study to the one described in Example 9 with RTE melon was performed on Golden Delicious apples. Apple fruits purchased in the local supermarket were surface sterilized in the bleach solution and cut into flat pieces (thickness of ~1 cm). These ready-to-eat (RTE) segments of apple were infected with E. coli O157:H7 as an indicator pathogen and then sprayed with either a two-component (colicins M+E7) or a five-component (colicins M+E7+K+B+5) formulations and the results were compared to spraying a control carrier solution containing plant extract without colicins.

For this series, the density of the O157:H7 (strain DSM19206) inoculum was set to $OD_{600}$=0.005 (about 5×10$^5$ cfu/ml) resulting in a measured actual load of about 1×10$^4$ CFU/g of fruit, and the pooling of 4 apple pieces per sample was done.

Significant differences between control treatment and colicin treatments were observed already upon 1 h storage at 4° C. (FIG. 13). These differences increased further with time. After 3 days storage at 4° C., more than one log reduction of bacterial load was observed for both colicin formulations if compared with colicin-free carrier control.

Example 11: Treatment of E. coli Contaminated Fresh Arugula Leaves with a Two-Component Colicin Mixture (Colicin M and Colicin E7)

Plant-made colicins were tested for antimicrobial activity against E. coli O157:H7 in fresh leaves of arugula (rocket salad, Eruca sativa Mill.). Arugula leaves were contaminated with E. coli O157:H7 as an indicator pathogen and then washed in the two-component colicin solution (colicins M+E7) (wash colicin). The results were compared to E. coli contaminated leaves without any washing (no treatment) and contaminated leaves washed with a carrier solution containing plant extract without colicins (wash carrier).

Arugula leaves have been purchased in the local supermarket. Leaves were inoculated with E. coli O157:H7 (strain DSM19206) by dipping in the sterile water containing bacterial cells. The inoculum was set to $1 \times 10^5$ cfu/ml ($OD_{600}$=0.001) resulting in a measured actual load of ~$1 \times 10^4$ CFU/g of arugula leaves. After 5 minutes incubation, the bacterial solution was decanted, and the excess liquid was removed from leaves using a salad spinner. The leaves were left to dry at room temperature for 30 minutes.

For colicin treatment, the leaves were dipped into 5 volumes of colicin solution and incubated for 10 minutes with an agitation. Because of the high leaf surface to mass ratio, the colicin dosage was increased compared to previous examples. We applied 3 mg colM+1 mg colE7 per liter of wash solution (corresponds to 15 mg colM+5 mg colE7 per kg of food). After removing the liquid, leaves were incubated at 10° C. Leaf samples were analyzed for microbial contamination after 1 hour and 1 day storage.

Interestingly, simple wash with a carrier solution efficiently removed bacterial cells with nearly one log CFU reduction after 1 hour storage compared to untreated samples (difference between colicin washed and untreated samples was 1.5 logs). However, after one day storage, there was practically no difference between untreated and carrier washed samples, and nearly one log CFU reduction for colicin treated samples compared to untreated or carrier washed ones (FIG. 14).

Example 12: Treatment of *E. coli* Contaminated Beef Steak Meat with a Two-Component Colicin Mixture (Colicin M, Colicin E7, Colicin Ia and Colicin K)

A similar exposure study to the one described in Example 8 with pork fillet steaks was performed on beef steak meat. Beef meat pieces of about 1 kg weight purchased in the local supermarket were trimmed to steaks of about 85 g weight and contaminated with *E. coli* O157:H7 (strain DSM19206) by dipping into bacterial solution. *E. coli* contamination resulted in a measured actual load of ~$1 \times 10^4$ CFU/g of meat. After 30 minutes drying at room temperature, steaks were sprayed with the four-component colicin solution (diluted plant extracts containing colicins M+E7+Ia+K). The colicin dosage was 3 mg/kg meat for colicin M and 1 mg/kg meat for each other colicin. Control samples were sprayed with a carrier solution only.

For analysis of efficacy, meat samples were stored at 4° C. for up to 3 days and analyzed for microbial counts at 1 hour, 24 hours, and 72 hours storage. One log CFU reduction of *E. coli* O157:H7 by colicin in comparison to carrier application was detected already at 1 hour post treatment; for two later time points, the CFU reduction was approximately two logs (FIG. 15).

Example 13: Treatment of *E. coli* Contaminated Beef Steak Meat with Four-Component Colicin Mixture (Colicin M, Colicin E7, Colicin Ia and Colicin K) Prior Grinding Beef meat pieces of about 1 kg weight were trimmed to cubes of about 100 g weight and inoculated by addition of 10 ml/kg bacterial suspension of *E. coli* O157:H7 (strain DSM19206) of ~$1 \times 10^6$ cfu/ml. The bacterial culture was equally distributed on beef cubes by tumbling.

Colicin (the blend of 3+1+1+1 mg/kg colM+colE7+colIa+colK) or carrier treatment was carried out by spraying and equal distribution of carrier/colicin solution on meat cubes by tumbling. Upon 30 minutes incubation at room temperature with colicin or carrier solution, meat was ground using a ø 6 mm and a ø 3 mm die subsequently with ProfiCook® PC-FW 1003 meat grinder (ProfiCook-Clatronic International GmbH, Kempen, Germany) and 25 g samples of ground meat were packed in sampling bags and stored at 4° C. In total, meat was incubated for 2 h at room temperature upon colicin application and stored at 4° C. Microbial counts were performed after 1 hour, 24 hours, and 72 hours storage at 4° C.

Nearly two logs reduction of *E. coli* population upon colicin treatment was observed already after 1 hour storage (FIG. 16). The difference was even higher (2.5 logs) after 24 hours. It was not possible to quantify the colicin effect after 72 hours storage, as no *E. coli* bacteria could be detected in colicin treated samples at this time point.

Furthermore, a very high reduction (nearly two logs) of detected O157:H7 CFUs in carrier samples from 1 h to 72 h storage at 4° C. was observed. One possible explanation for this finding could be that grinding of contaminated meat poses the stress to bacteria and reduces their viability.

Example 14: General Scheme of Colicin Production

FIG. 17 shows a flow diagram of steps of two expression and purifcation processes. A flow diagram summarizing key steps in a production process of producing colicin proteins is shown. Key process steps are described in the following (step numbers correspond to the steps indicated in FIG. 18. The induction of gene expression can be accomplished by one of two alternative methods (described below), which share common downstream purification unit operations.

Step 1a. Inoculum Production for *Agrobacterium* Induction Method

The *Agrobacterium tumefaciens* bacterial vector containing a TMV transcript with the gene insert for a colicin of interest is grown in defined medium under aseptic conditions following strict quality SOPs; this bacterial suspension constitutes the inoculum. An *Agrobacterium* strain harboring a colicin expression vector, such as colicin M expression vector pNMD 10220, is grown in medium containing demineralized water, yeast extract, peptones, minerals, kanamycin and rifampicin. The removal of residual antibiotics and fermentation chemicals is achieved by high dilution of the bacterial solution before inoculation of plants and the ultra- and dia-filtration procedures during plant biomass extraction and processing. All raw materials and processing aids are food grade. A multi-vial Master Vector Bank of the vector is prepared and stored at −80° C., from which aliquots are removed as Working Vector Banks of the inoculum for each manufacturing batch.

Each Working Bank of *Agrobacterium* strain pNMD 10220 is handled in a way to reduce the risk of contamination by foreign microorganisms. This includes use of sterile materials for bacterial cultivation, quality control checks to ensure axenic culture, and confirmation of strain identity before plant inoculation. Samples not meeting criteria are rejected and disposed, and new aliquots are drawn from the Master Bank. If a problem is identified at the Master Bank level, a new Master Bank is generated and subjected to quality control procedures before further use.

Step 1b. Ethanol Induction of Transgenic Plants

In this variation of the method, transgenic plants carrying an ethanol-inducible promoter are used. The procedure was developed by Notifier and described by Werner (Werner 2011). The process is based on inducible release of viral RNA replicons from stably integrated DNA pro-replicons. A simple treatment with dilute ethanol releases the replicon leading to RNA amplification and high-level production of the desired colicin protein.

Step 2. Host Plant Preparation

For agroinduction, normal seeds of *Spinacia oleracea* (spinach), *Beta vulgaris* (beet) or other suitable host plants are obtained from qualified seed producers. For ethanol induction, transgenic seeds developed by Notifier are used, which contain the gene insert for the desired colicin driven by an ethanol-inducible promoter. With either method of induction, plants are propagated in trays using a soil based substrate, fertilizer and water. For seeding, plant propagation, target expression and plant harvest, the principles of Good Agriculture and Collection Practices (GACP) are applied. All used materials underlie a quality management system ensuring a predefined quality.

Step 3a. Inoculation of Host Plants with Agrobacterial Vector

The *A. tumefaciens* inoculum carrying the selected colicin replicon is applied to greenhouse-grown and quality tested host plants through the stomata (pores) in the leaves. The plant hence takes the place of a conventional "fermenter" in the production of the product. The *Agrobacterium* inoculum and the host plants are cultured under predefined and controlled conditions. At a specified time point after seeding the plants are treated with a defined concentration of *Agrobacterium* in dilution buffer. Inoculation of plants is accomplished by either vacuum-mediated infiltration after dipping the plant leaves in a suspension of the inoculum, or via a procedure wherein the inoculum is sprayed onto plant leaves mixed with a surfactant (Gleba 2014; Tusé 2014). Via either method, the *agrobacteria* are efficiently internalized into the plant and gain systemic distribution.

The *agrobacteria* infect the plant cells and insert the T-DNA plasmid into the nucleus, which initiates synthesis of colicin-encoding RNA transcripts. Amplification of the transcript and translation of the colicin RNA message into colicin occurs in the cytoplasm of each plant cell.

Step 3b. Ethanol Induction

In this variation of the method, a simple treatment of the transgenic plants carrying the colicin gene with dilute ethanol (2.5% v/v) releases the replicon leading to RNA amplification and high-level colicin production. To achieve tight control of replicon activation and spread in the non-induced state, the viral vector has been deconstructed, and its two components, the replicon and the cell-to-cell movement protein, have each been placed separately under the control of an inducible promoter (Werner 2011). Throughout the induction period, colicin protein accumulates in the tissues of the host plant. The inducer (ethyl alcohol) is diluted during plant growth and any traces remaining are removed during downstream purification.

Step 4. Incubation

After agro-inoculation or ethanol induction, the plants are incubated for 5-10 days under controlled temperature, humidity, and light condition to allow for accumulation of the desired protein. During this incubation period, there is rapid systemic replication of the vector and expression and accumulation of the induced product.

Step 5. Harvest

Plants producing colicin protein are harvested typically 8-9 days post inoculation/induction. Samples of plant biomass are taken for analyses of colicin protein content, general health and other process QC procedures prior to large-scale extraction. Plants in trays are transported to the cutting operation. The plants' aerial biomass (i.e. leaves and part of the stems) are mechanically cut and harvested into bins, which are transported to the extraction room.

Step 6. Homogenization of Plant Tissue

Cut plant biomass is disintegrated by homogenization in a grinder using an extraction buffer; the course plant material and fibers are removed, and the protein-containing soluble stream is further purified through a series of pH-assisted precipitations and filtration steps.

Step 7. Acidic Extraction

The complex stream from Step 6 is subjected to low pH treatment to help precipitate major host cell proteins, resulting in a partially purified stream enriched for the colicin protein.

Step 8. First Clarification

Precipitated proteins and other impurities are removed by centrifugation and/or filtration.

Step 9. Neutralization

After clarification in Step 8, the process stream is pH-adjusted with alkali for further processing.

Step 10. Second Clarification

The solution from Step 9 is further clarified by centrifugation and/or filtration.

Step 11 and Step 12. Ultrafiltration/Diafiltration

Additional impurities are removed by ultrafiltration and diafiltration; typically, impurities that are less than 5-10 kDa in mass are eliminated at this step.

Step 13. Chromatography

At this stage, the product-enriched solution can be subjected to one of two additional purification steps. If a relatively pure colicin product is desired, the solution is subjected to cation-exchange chromatography, which removes additional host-cell proteins and plant metabolites such as polyphenols, resulting in a clarified, enriched product. One or more colicin proteins prepared by this method and to meet this level of purity can be blended into a final solution that will be further processed into COLICIN Isolate. If a less purified bulk product will suffice for certain applications, the chromatography step is eliminated, and this solution (containing one or a blend of colicin proteins) will be further processed into COLICIN Concentrate.

Steps 14—17. Formulation, Fill and Finish

The final COLICIN Concentrate or COLICIN Isolate precursor solution is stabilized and standardized by the addition of water, sodium citrate/citric acid and sodium chloride. Finally, the solution is filter-sterilized through a 0.22 µm membrane filtration unit and filled as a bulk liquid concentrate, or freeze dried to produce a dry, off-white to light tan powdered product. Prior to release, the bulk products are tested to ensure compliance with the respective final product specification for COLICIN Concentrate or COLICIN Isolate.

In-Process Controls and Quality Assurance

Notifier applies rigorous in-process controls to manage the quality of process intermediates and final products throughout the manufacturing process. Materials not meeting pre-determined specifications are rejected. Product release is done after each batch passes rigorous identity and potency tests. A Quality Management system is in place to ensure conformance with industry standards and federal and local regulatory guidelines.

A.1 Possible Specifications

Specifications for each grade of COLICIN produced by this process are shown in Table 8 (COLICIN Concentrate) and Table 9 (COLICIN Isolate).

TABLE 8

Specification for COLICIN Concentrate Product
COLICIN Concentrate

| Parameter | Specification limit | Method |
|---|---|---|
| Appearance | Powder, beige to brownish | Visual |
| Specific Activity | >10,000 AU/g | Serial-dilution based assay |
| pH of a 1% solution | 6.5-8.5 | Potentiometric |
| Heavy metals (sum of Ag, As, Bi, Cd, Cu, Hg, Mo, Pb, Sb, Sn) | ≤30 ppm | USP38<233> |
| Lead | ≤5 ppm | USP38<233> |
| Bioburden | ≤5,000 CFU total per g | USP32<61> |
| *Agrobacterium* per 10 g sample | 0 (absent) | Selective plate-based assay |
| Undesirable microorganisms, including *Escherichia coli*, *Pseudomonas aeruginosa*, *Salmonella* spp. or coagulase-positive *Staphylococcus* spp., per 25 g | 0 (absent) | USP32<1111> |
| Stability (dry concentrate; 0-10° C.) | >6 months | Specific activity by serial dilution-based assay |

TABLE 9

Specification for COLICIN Isolate Product
COLICIN Isolate

| Parameter | Specification limit | Method |
|---|---|---|
| Appearance | Powder, white to beige | Visual |
| Specific Activity | >25,000 AU/g | Serial-dilution based assay |
| pH of a 1% solution | 6.5-8.5 | Potentiometric |
| Heavy metals (sum of Ag, As, Bi, Cd, Cu, Hg, Mo, Pb, Sb, Sn) | ≤30 ppm | USP38<233> |
| Lead | ≤5 ppm | USP38<233> |
| Bioburden | ≤10 CFU total per 25 g sample | USP32<61> |
| *Agrobacterium* per 10 g sample | 0 (absent) | Selective plate-based assay |
| Undesirable microorganisms, including *Escherichia coli*, *Pseudomonas aeruginosa*, *Salmonella* spp. or coagulase-positive *Staphylococcus* spp., per 25 g | 0 (absent) | USP32<1111> |
| Stability (dry concentrate; 0-10° C.) | >6 months | Specific activity by serial dilution-based assay |

Example 15: Colicin Protein Purification

We developed a simple downstream process for colicin-containing plant biomass, which includes homogenization of plant tissue, acidic extraction, clarification and neutralization of the plant extract followed by ultrafiltration and diafiltration steps. The colicin-enriched solution can then be subjected to one of two additional purification steps. If a relatively pure colicin product is desired, such as when using *Nicotiana* as the host plant, the extract is subjected to ion-exchange chromatography to remove additional host-cell proteins and plant metabolites such as alkaloids and polyphenols, resulting in a clarified, enriched product with 90% colicin protein purity (colicin isolate). Such purified product can be used in ready to eat food products or as a package additive. If a less purified bulk product suffices for certain applications such as food sprays or washes, edible plant species can be used without employment of the chromatography step. Typically, this solution (colicin concentrate) contains one or a blend of colicin proteins at 40-50% purity (FIG. 18).

Six days after inoculation, infected leaf enriched material was harvested. Plant biomass was homogenized in the presence of extraction solution (10 mM HCl, 10 mM $Na_2S_2O_5$, 2.5 mM $Na_2$-EDTA) at a buffer/biomass ratio of 1:1 vol/wt. The pH of the plant homogenate was adjusted to 4.0 and clarified by centrifugation at 20.000×g for 20 minutes. The clarified extract was neutralized with 1 M sodium hydroxide and further clarified by centrifugation and depth filtration (Filter sheets: BECO® KDS12-Begerow). The filtrate was 4-fold concentrated by ultrafiltration with a 5 kDa hollow-fiber module. The retentate was diafiltered 5 times against 5 mM citrate, 50 mM NaCl pH 5.0. The resulting concentrate was filter sterilized using a 0.45 μm filter.

For further purification the concentrate was loaded on a Fractogel® EMD $SO_3^-$ (Merck Millipore) column equilibrated with 5 mM Citric acid, 50 mM NaCl pH 5.0. The column was washed with 25 mM sodium phosphate pH 7.3 to reduce weakly bound proteins. The target protein was eluted with 100 mM citrate pH 9.7. The eluate was diafiltered against 10 mM citrate, 137 mM NaCl pH 7.3 resulting in colicin M isolate.

The purity of the colicin concentrate and isolate was determined by using SDS-PAGE (FIG. 18); Coomassie blue-stained protein bands were quantitated using a densitometer. The purity of the colicin M isolate was determined by capillary gel electrophoresis using a Bioanalyzer 1200 series instrument (Agilent Technologies, Böblingen, Germany).

Example 16: Plasmid Constructs for the Expression of Colicins E5, E8, E9, A, S4, 10, R, 28b, Y, Ib, and Cloacin DF13

Aiming to find other potential colicin candidates with desired antimicrobial activity, we selected eleven additional colicin genes for the expression in plants. They represented three activity groups and various receptor specificities (Table 10). Thus, we were able to express 23 colicin genes covering nearly all *E. coli* colicins described up to now.

The second set comprises colicins colicins E5, E8, E9, A, S4, 10, R, 28b, Y, Ib, and cloacin DF13. Respective amino acid sequences were retrieved from GenBank; corresponding nucleotide sequences with codon usage optimized for *Nicotiana benthamiana* were synthesized by Life Technologies GmbH (Darmstadt, Germany). In case of colicins E5, E8, E9, Y and cloacin DF13 the coding sequence was interrupted by by insertion of the cat 1 intron (the first intron from *Ricinus communis* cat1 gene for catalase CAT1 (GenBank: D21161.1, nucleotide positions between 679 and 867)) to prevent the cytotoxicity in *Escherichia coli* cells used for cloning. Colicin coding sequences were inserted into TMV-based assembled viral vector pNMD035 (described in detail in WO2012/019660) resulting plasmid constructs depicted in FIG. 19A.

TABLE 10

List of colicins used in examples (the second set).

| No. | Colicin | Receptor | Activity | Accession No. |
|---|---|---|---|---|
| 1 | colE5 | BtuB | tRNase | AHK10569.1 |
| 2 | colE8 | BtuB | DNase | ACS71682.1 |
| 3 | colE9 | BtuB | DNase | ACM07430.1 |
| 4 | cloacin DF13 | IutA | 16S rRNase | NP_052372.1 |
| 5 | colA | BtuB | pore-forming | P04480.1 |
| 6 | colS4 | OmpF | pore-forming | CAB46008.1 |
| 7 | col10 | Tsx | pore-forming | CAA57998.1 |
| 8 | colR | OmpA | pore-forming | AGV40809.1 |
| 9 | col28b | OmpA | pore-forming | CAA44310.1 |
| 10 | colY | FepA | pore-forming | AAF82683.1 |
| 11 | colIb | Cir | pore-forming | AAA23188.1 |

Colicins with nuclease activities were co-expressed with corresponding immunity proteins to reduce the toxic effect and increase the accumulation of these colicins. Colicin immunity proteins used in this example are listed in the Table 11.

TABLE 11

List of immunity proteins used in examples (the second set).

| No. | Immunity protein | Specificity | Accession No. |
|---|---|---|---|
| 1 | ImmE5 | colE5 (tRNAse) | AHK10570.1 |
| 3 | ImmE8 | colE8 (DNAse) | ACS71683.1 |
| 4 | ImmE9 | colE9 (DNAse) | ACM07431.1 |
| 5 | ImmDF13 | colDF13 (rRNAse) | NP_052371.1 |

Immunity proteins ImmE5, ImmE8, ImmE9 and ImmDF13 are specific for colicins E5, E8, E9 and cloacin DF13, respectively. Amino acid sequences of immunity proteins were retrieved from GenBank; corresponding nucleotide sequences with codon usage optimized for *Nicotiana benthamiana* were synthesized by Life Technologies and subcloned into PVX-based assembled viral vector pNMD670 as described in WO2012/019660. An overview over the resulting plasmid constructs is shown in FIG. 19B.

Example 17: Expression Screen for Colicins E5, E8, E9, A, S4, 10, R, 28b, Y, Ib, and Cloacin DF13

6 weeks old *Nicotiana benthamiana* plants were infiltrated using needleless syringe with diluted *Agrobacterium tumefaciens* cultures carrying TMV-based assembled vectors for colicin expression. In case of colicins E5, E8, E9 and cloacin DF13, *Agrobacterium* cultures carrying TMV-based vector for colicin expression were mixed inn equal proportions with other cultures carrying PVX-based vectors for the expression of corresponding immunity proteins. Overnight cultures were adjusted to OD600=1.5 and further diluted 1:100 with infiltration buffer containing 10 mM MES, pH 5.5 and 10 mM MgSO4. 5-6 days post infiltration, plant material was harvested and used for the protein extraction. Protein were extracted either with Laemmli buffer to recover all protein forms or with HEPES buffer to recover total soluble protein (TSP) fraction only. Total soluble protein concentration was determined using Bradford assay, and protein extracts were analyzed using SDS-PAGE with Coomasssie staining (FIGS. 20A-20B). In our experiment, all tested colicins were expressed on reasonably high levels varying between 6 and 50% of TSP as determined by comparison with Bovine Serum Albumin (BSA) protein.

Example 18: Antimicrobial Activity Screen for Colicins E5, E8, E9, A, S4, 10, R, 28b, Y, Ib, and Cloacin DF13

We analyzed antimicrobial activity of plant-made recombinant colicins against Big 7 STEC strains and against emerging O104:H4 EHEC as described in Example 3. For semi-quantitative comparison, relative antimicrobial activity of recombinant colicins was represented in arbitrary units (AU) per mg of fresh weight of plant tissue. The results of colicin activity screen were represented in FIG. 21.

The majority of tested colicins (7 out of 11) had no or very low activity against tested strains. Four other tested colicins demonstrated rather narrow strain specificity with reasonably high activity against 1-3 strains.

Overview of Nucleic Acid and Amino Acid Sequences

SEQ ID NO: 1
Amino acid sequence of colicin M
METLTVHAPSPSTNLPSYGNGAFSLSAPHVPGAGPLLVQVVYSFFQSPNM

CLQALTQLEDYIKKHGASNPLTLQIISTNI GYFCNADRNL VLHPGISV

YD AYHFAKPAPS QYDYRSMNMKQMSGNVTTPIVALAHYLWGNGAERSV

NIAN IGLKISPMKI NQIKDIIKSG VVGTFPVSTK FTHATGDYNVIT

GAYLGNITLKTEGTLTISANGSWTYNGVVRSYDDKYDFNASTHRGIIGES

LTRLGAMFSGKEYQILLPGEIHIKESGKR

SEQ ID NO: 2
pNMD035: empty TMV-based vector for cloning

SEQ ID NO: 3
pNMD10221: TMV-based vector with ColM insertion

SEQ ID NO: 4
pNMD670: an empty PVX-based vector for cloning

SEQ ID NO: 5
pNMD11740: PVX-based vector with ColM insertion

SEQ ID NO: 6
amino acid sequence of colicin E7
MSGGDGRGHN SGAHNTGGNI NGGPTGLGGN GGASDGSGWS

SENNPWGGGS GSGVHWGGGS GHGNGGGNSN SGGGSNSSVA

APMAFGFPAL AAPGAGTLGI SVSGEALSAA IADIFAALKG

PFKFSAWGIA LYGILPSEIA KDDPNMMSKI VTSLPAETVT

NVQVSTLPLD QATVSVTKRV TDVVKDTRQH IAVVAGVPMS

VPVVNAKPTR TPGVFHASFP GVPSLTVSTV KGLPVSTTLP

RGITEDKGRT AVPAGFTFGG GSHEAVIRFP KESGQKPVYV

SVTDVLTPAQ VKQRQDEEKR LQQEWNDAHP VEVAERNYEQ

ARAELNQANK DVARNQERQA KAVQVYNSRK SELDAANKTL

ADAKAEIKQF ERFAREPMAA GHRMWQMAGL KAQRAQTDVN

NKKAAFDAAA KEKSDADVAL SSALERRKQK ENKEKDAKAK

LDKESKRNKP GKATGKGKPV NNKWLNNAGK DLGSPVPDRI

ANKLRDKEFK SFDDFRKKFW EEVSKDPELS KQFSRNNNDR

MKVGKAPKTR TQDVSGKRTS FELHHEKPIS QNGGVYDMDN

ISVVTPKRHI DIHRGK

SEQ ID NO: 7
amino acid sequence of colicin Ia
MSDPVRITNPGAESLGYDSDGHEIMAVDIYVNPPRVDVFHGTPPAWSSFG
NKTIWGGNEWVDDSPTRSDIEKRDKEITAYKNTLSAQQKENENKRTEAGK
RLSAAIAAREKDENTLKTLRAGNADAADITRQEFRLLQAELREYGFRTEI
AGYDALRLHTESRMLFADADSLRISPREARSLIEQAEKRQKDAQNADKKA
ADMLAEYERRKGILDTRLSELEKNGGAALAVLDAQQARLLGQQTRNDRAI
SEARNKLSSVTESLNTARNALTRAEQQLTQQKNTPDGKTIVSPEKFPGRS
STNHSIVVSGDPRFAGTIKITTSAVIDNRANLNYLLSHSGLDYKRNILND
RNPVVTEDVEGDKKIYNAEVAEWDKLRQRLLDARNKITSAESAVNSARNN
LSARTNEQKHANDALNALLKEKENIRNQLSGINQKIAEEKRKQDELKATK
DAINFTTEFLKSVSEKYGAKAEQLAREMAGQAKGKKIRNVEEALKTYEKY
RADINKKINAKDRAAIAAALESVKLSDISSNLNRFSRGLGYAGKFTSLAD
WITEFGKAVRTENWRPLFVKTETIIAGNAATALVALVFSILTGSALGIIG
YGLLMAVTGALIDESLVEKANKFWGI SEQ ID NO: 8
amino acid sequence of colicin Ib
MSDPVRITNPGAESLGYDSDGHEIMAVDIYVNPPRVDVFHGTPPAWSSFG
NKTIWGGNEWVDDSPTRSDIEKRDKEITAYKNTLSAQQKENENKRTEAGK
RLSAAIAAREKDENTLKTLRAGNADAADITRQEFRLLQAELREYGFRTEI
AGYDALRLHTESRMLFADADSLRISPREARSLIEQAEKRQKDAQNADKKA
ADMLAEYERRKGILDTRLSELEKNGGAALAVLDAQQARLLGQQTRNDRAI
SEARNKLSSVTESLKTARNALTRAEQQLTQQKNTPDGKTIVSPEKFPGRS
STNHSIVVSGDPRFAGTIKITTSAVIDNRANLNYLLTHSGLDYKRNILND
RNPVVTEDVEGDKKIYNAEVAEWDKLRQRLLDARNKITSAESAINSARNN
VSARTNEQKHANDALNALLKEKENIRSQLADINQKIAEEKRKRDEINMVK
DAIKLTSDFYRTIYDEFGKQASELAKELASVSQGKQIKSVDDALNAFDKF
RNNLNKKYNIQDRMAISKALEAINQVHMAENFKLFSKAFGFTGKVIERYD
VAVELQKAVKTDNWRPFFVKLESLAAGRAASAVTAWAFSVMLGTPVGILG
FAIIMAAVSALVNDKFIEQVNKLIGI

REFERENCES

Engler C, Gruetzner R, Kandzia R, Marillonnet S (2009) Golden Gate shuffling: a one-pot DNA shuffling method based on type IIs restriction enzymes. PLoS ONE 4(5): e5553.

Horsch R B, Fraley R T, Rogers S G, Sanders P R, Lloyd A (1985) A simple and general method for transferring genes into plants. Science 227:1229-1231.

Marillonnet S, Giritch A, Gils M, Kandzia R, Klimyuk V, Gleba Y (2004) In planta engineering of viral RNA replicons: efficient assembly by recombination of DNA modules delivered by *Agrobacterium*. Proc Natl Acad Sci USA 101(18): 6852-7.

Weber E, Engler C, Gruetzner R, Werner S, Marillonnet S (2011) A modular cloning system for standardized assembly of multigene constructs. PLoS ONE 6(2): e16765.

Werner S, Breus O, Symonenko Y, Marillonnet S, Gleba Y (2011) High-level recombinant protein expression in transgenic plants by using a double-inducible viral vector. PNAS 108(34): 14061-14066.

The invention claimed is:

1. A method of preventing or reducing contamination of an object with enterohaemorrhagic *E. coli* (EHEC), comprising contacting said object with colicin M or a derivative thereof in combination with one or more colicins selected from the group consisting of colicin Ia and colicin Ib, wherein said colicin M and said derivative have a translocation domain, a receptor binding domain, and an activity domain from the N- to the C-terminus, wherein said derivative of colicin M has a translocation domain of amino acid residues 1 to 35 of SEQ ID NO: 1 or a translocation domain having from 1 to 8 amino acid substitutions, insertions, additions and/or deletions compared to residues 1 to 35 of SEQ ID NO: 1; and said derivative of colicin M comprises a central receptor-binding domain as follows:

the receptor-binding domain has residues 36 to 140 of colicin M of SEQ ID NO: 1 or has a domain having from 1 to 10 amino acid substitutions, insertions, additions and/or deletions compared to residues 36 to 140 of SEQ ID NO: 1, or has an amino acid sequence identity of at least 90% to the receptor-binding domain of SEQ ID NO: 1, or has an amino acid sequence similarity of at least 95% to the receptor-binding domain SEQ ID NO: 1.

2. The method according to claim 1, wherein contamination of an object with EHEC serotype O157:H7 is prevented or reduced.

3. The method according to claim 1, wherein contamination of an object with any one or all of the following *E. coli* serotypes is prevented or reduced: serotype O26:H11, serotype O45:H2, serotype O103:H11, serotype O111:H8, serotype O157:H7, and serotype O104:H4.

4. The method according to claim 1, wherein contamination of an object with any one or all of the following *E. coli* serotypes is prevented or reduced: serotype O26:H11, serotype O45:H2, serotype O103:H11, serotype O111:H8, serotype O145:NM, O157:H7, and O104:H4.

5. The method according to claim 1, wherein said object is contacted with an aqueous solution containing colicin M or its derivative in combination with one or more colicins selected from the group consisting of colicin Ia and colicin Ib by spraying with said aqueous solution or by dipping said object into said aqueous solution.

6. The method according to claim 1, wherein said food is immersed for at least 10 seconds, preferably for at least 1 minute, preferably for at least 5 minutes into an aqueous solution of colicin M or its derivative.

7. The method according to claim 1, wherein said colicin M or its derivative is produced by expression in a plant or in plant cells, followed by removing undesired components from said plant or said plant cells.

8. The method according to claim 1, wherein said object is food selected from meat, raw fruit and raw vegetable.

9. The method according to claim 1, wherein said colicin M has the amino acid sequence of SEQ ID NO: 1.

10. The method according to claim 1, wherein the derivative of colicin M has a toxicity that is such that the derivative and the colicin M of SEQ ID NO: 1 produce spots free of viable bacteria of sensitive *E. coli* strain DH10B of the same diameter 12 hours after spotting 5 microliters of a solution of said derivative of colicin M and the colicin M of SEQ ID NO: 1 onto a lawn of the sensitive *E. coli* strain on an agar plate and subsequent incubation of the agar plate at 37° C., wherein the concentration of the derivative of colicin M is at most 5 times that of the comparative solution of the colicin M of SEQ ID NO: 1.

11. The method according to claim 1, wherein said derivative of colicin M comprises the C-terminal activity domain of residues 141 to 271 of colicin M or an activity domain having from 1 to 30 amino acid substitutions, insertions, additions and/or deletions compared to residues 141 to 271 of SEQ ID NO: 1.

12. The method according to claim 1, wherein said colicin M or its derivative is used in combination with one or more colicins selected from the group consisting of colicin E7, colicin B, colicin Ia, colicin U, colicin K, and colicin 5, or a derivative of colicin E7, colicin B, colicin U, colicin K, and colicin 5; and/or said colicin M or its derivative is used in combination with one or more colicins selected from the group consisting of colicin E5, colicin E8, colicin E9, colicin A, colicin S4, colicin 10, colicin R, colicin 28b, colicin Y, and cloacin DF13, or a derivative of E5, colicin E8, colicin E9, colicin A, colicin S4, colicin 10, colicin R, colicin 28b, colicin Y, colicin Ib, and cloacin DF13.

13. The method according to claim 1, wherein said colicin M or its derivative is used in combination with colicin E7 or a derivative thereof.

14. The method according to claim 13, wherein contamination with any one or all of the following *E. coli* serotypes is prevented or reduced: serotypes O26:H11, O45:H2, O103:H11, O111:H8, O145:NM, O157:H7, O104:H4, and O121:H19.

* * * * *